United States Patent
Lee et al.

(10) Patent No.: US 6,348,596 B1
(45) Date of Patent: *Feb. 19, 2002

(54) NON-FLUORESCENT ASYMMETRIC CYANINE DYE COMPOUNDS USEFUL FOR QUENCHING REPORTER DYES

(75) Inventors: Linda G. Lee, Palo Alto; Ronald J. Graham, Pleasanton; Khairuzzaman B. Mullah, Union City; Francis T. Haxo, San Francisco, all of CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,740

(22) Filed: Jul. 20, 1999

Related U.S. Application Data

(63) Continuation-in-part of application No. 09/012,525, filed on Jan. 23, 1998, now Pat. No. 6,080,868.

(51) Int. Cl.[7] .............................................. C07D 293/00
(52) U.S. Cl. ........................... 546/75; 546/87; 546/165; 546/174; 546/270.1; 546/284.1; 435/6; 536/22.1; 536/25.3
(58) Field of Search ...................... 546/73, 165, 174, 546/284.1, 87, 276.1; 435/6; 536/22.1, 25.3

(56) References Cited

U.S. PATENT DOCUMENTS

| | | | |
|---|---|---|---|
| 2,078,233 A | * 4/1937 | Brooker .................. 546/165 X |
| 2,141,434 A | * 12/1938 | Hamer et al. ........... 546/165 X |
| 2,152,615 A | * 3/1939 | Zeh ......................... 546/165 X |
| 2,269,234 A | 1/1942 | Sprague .................. 546/165 X |
| 4,230,558 A | 10/1980 | Fulwyler ..................... 209/3.1 |
| 4,415,732 A | 11/1983 | Caruther et al. .............. 536/27 |
| 4,439,356 A | 3/1984 | Khanna et al. ........... 549/388 X |
| 4,458,066 A | 7/1984 | Caruthers et al. ........ 536/27 X |
| 4,757,141 A | 7/1988 | Fung et al. ..................... 536/27 |
| 4,811,218 A | 3/1989 | Hunkapiller et al. ... 364/413.01 |
| 4,855,225 A | 8/1989 | Fung et al. ..................... 435/6 |
| 4,883,867 A | 11/1989 | Lee et al. ...................... 536/28 |
| 5,188,934 A | 2/1993 | Menchen et al. ............... 435/6 |
| 5,212,304 A | 5/1993 | Fung et al. ................... 544/157 |
| 5,231,191 A | 7/1993 | Woo et al. ................... 549/220 |
| 5,258,538 A | 11/1993 | Fung et al. ..................... 558/81 |
| 5,321,130 A | 6/1994 | Yue et al. ................... 536/23.1 |
| 5,410,030 A | 4/1995 | Yue et al. ................... 536/23.1 |
| 5,436,134 A | 7/1995 | Haugland et al. .............. 435/34 |
| 5,449,767 A | 9/1995 | Ward et al. .................... 536/24 |
| 5,534,416 A | 7/1996 | Millard et al. ................. 436/34 |
| 5,538,848 A | 7/1996 | Livak et al. ..................... 435/5 |
| 5,582,977 A | 12/1996 | Yue et al. ....................... 435/6 |
| 5,656,449 A | 8/1997 | Yue .............................. 435/34 |
| 5,658,735 A | 8/1997 | Lee ................................ 435/6 |
| 5,658,751 A | 8/1997 | Yue et al. ...................... 435/34 |
| 5,688,648 A | 11/1997 | Mathies et al. ................. 435/6 |
| 5,691,146 A | 11/1997 | Mayrand ........................ 435/6 |
| 5,736,333 A | 4/1998 | Livak et al. ..................... 435/6 |
| 5,770,716 A | 6/1998 | Khan et al. ................. 536/23.1 |
| 5,821,356 A | 10/1998 | Khan et al. ................ 536/26.26 |
| 5,847,162 A | 12/1998 | Lee et al. ..................... 549/327 |
| 5,863,727 A | 1/1999 | Lee et al. ........................ 435/6 |
| 5,863,753 A | 1/1999 | Haugland et al. .............. 435/34 |
| 6,080,868 A | 6/2000 | Lee et al. ..................... 548/100 |

FOREIGN PATENT DOCUMENTS

| | | |
|---|---|---|
| EP | 0 070 685 | 1/1983 |
| EP | 0 232 967 | 8/1987 |
| EP | 0 272 007 | 6/1988 |
| EP | 0 512 334 | 11/1992 |
| EP | 0 601 889 | 6/1994 |
| EP | 0 710 668 | 5/1996 |
| EP | 0 714 986 | 6/1996 |
| JP | 9-288326 | 11/1997 |
| WO | WO 96/04405 | 2/1996 |
| WO | WO 96/15270 | 5/1996 |
| WO | WO 97/45539 | 12/1997 |
| WO | WO 99/37717 | 7/1999 |
| WO | WO 00/75237 | 12/2000 |

OTHER PUBLICATIONS

Benson et al., 1995, "Fluorescence Energy–Transfer Cyanine Heterodimers with High Affinity for Double Stranded DNA", Anal. Biochem. 231:247–255.

Bergstrom et al., 1989, "Palladium–Mediated Coupling between Organic Disulfides and Nucleic Acid Constituent", J. Am. Chem. Soc. 111:374–375.

Brinkley, 1992, "A Brief Survey of Methods for Preparing Protein Conjugates with Dyes, Haptens, and Cross–Linking Reagents", Bioconjugate Chem. 3:2–13.

Brooker et al., 1942, "Color and Constitution. V. The Absorption of Unsymmetrical Cyanines. Resonance as a Basis for a Classification of Dyes", J. Am. Chem. Soc. 64:199–210.

(List continued on next page.)

Primary Examiner—Floyd D. Higel
(74) Attorney, Agent, or Firm—Pennie & Edmonds LLP

(57) ABSTRACT

The invention provides asymmetric cyanine dye compounds having the general formula:

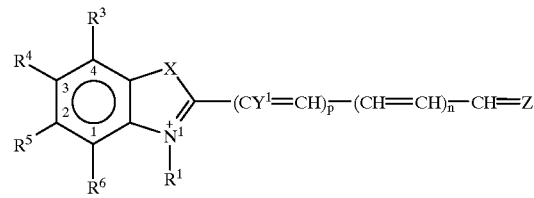

including substituted forms thereof, which are non-fluorescent quencher molecules. The invention further provides reporter-quencher dye pairs, wherein the asymmetric cyanine dyes are the quenchers, polynucleotides incorporating the asymmetric cyanine dyes, and nucleic acid hybridization detection methods utilizing the dye-labeled polynucleotides.

28 Claims, 16 Drawing Sheets

OTHER PUBLICATIONS

Cardullo et al. 1988, "Detection of Nucleic Acid Hybridization by Nonradiative Fluorescence Resonance Energy Transfer", Proc. Natl. Acad. Sci. USA 85:8790–8794.

Caruthers et al., 1982, "New Methods for Synthesizing Deoxyoligonucleotides", Genetic Engineering 4:1–17.

Daskalov et al., 1981, "Synthesis and Propertiesof $O^6$–Substituted Guanosine Derivatives", Bull. Chem. Soc. Japan 54:3076–3083.

Ficken, 1971, "Cyanine Dyes", In *The Chemistry of Synthetic Dyes vol. IV*, Chapter 5, Venkataraman, pp. 211–340.

Gaffney and Jones, 1982, "A New Strategy for the Protection of Deoxyguanosine during Oligonucleotide Synthesis", Tetrahedron Lett. 23:2257–2260.

Gebeyehu et al., 1987, "Novel Biotinylated Nucleotide—Analogs for Labeling and Colorimetric Detection of DNA", Nucl. Acids. Res. 15:4513–4534.

Gibson and Benkovic, 1987, "Synthesis and Application of Derivatizable Oligonucleotides", Nucl. Acids. Res. 15:6455–6467.

Hamer, 1964, "Trimethincyanines with Substituents on the Chain", in *The Cyanine Dyes and Related Compounds*, Chapter VI, John Wiley, NY, pp. 148–199.

Hamer, 1964, "Symmetrical and Unsymmetrical Pentamethincyanines, Including those with Substituents on the Chain", in *The Cyanine Dyes and Related Compounds*, Chapter VII, John Wiley, NY, pp. 200–243.

Hamer, 1964, "Symmetrical and Unsymmetrical Heptamethincyanines, Including those with Substituents on the Chain; Polymethincyanines", in *the Cyanine Dyes and Related Compounds*, Chapter VIII, John Wiley, NY, pp. 244–267.

Haralambidis et al., 1987, "Preparation of Base–Modified Nucleosides Suitable for Non–Radioactive Label Attachment and Their Incorporation into Synthetic Oligodeoxyribonucleotides", Nucl. Acids. Res. 15:4857–4876.

Heller and Morrison, 1985, "Chemiluminescent and Fluorescent Probes for DNA Hybridization Systems", in *Rapid Detection and Identification of Infectious Agents*, Kingsbury and Falkow, ed., Academic Press, Inc., pp. 245–256.

Himmelsbach et al., 1984, "The ρ–Nitrophenylethyl (NPE) Group", Tetrahedron Lett. 40:59–72.

Holland et al., 1991, "Detection of Specific Polymerase Chain Reaction Product by Utilizing the 5'→3' Exonuclease Activity of *Thermus aquaticus* DNA Polymerase", Proc. Natl. Acad. Sci. USA 88:7276–7280.

Hung et al., 1996, "Cyanine Dyes with High Absorption Cross Section as Donor Chromophores in Energy Transfer Primers", Anal. Biochem. 243:15–27.

Inagaki et al., 1998, "Photothermographic Material Containing Cyanine Dye for Low–Fog Images", CA128(4):1162, abstr. No. 41644t.

Jones et al., 1981, "The Protection of Uracil and Guanine Residues in Oligonucleotide Synthesis", Tetrahedron Lett. 22:4755–4758.

Landegren et al., 1998, "Reading Bits of Genetic Information: Methods for Single–Nucleotide Polymorphism Analysis", Genome Res. 8:769–776.

Lee et al., 1997, "New Energy Transfer Dyes for DNA Sequencing", Nucl. Acids Res. 25:2816–2822.

Lee et al., 1993, "Allelic Discrimination by Nick–Translation PCR with Fluorogenic", Nucl. Acids Res. 21:3761–3766.

Lee et al., 1986, "Thiazole Orange: A New Dye for Reticulocyte Analysis", Cytometry 7:508–517.

Livak et al., 1995, "Oligonucleotides with Fluorescent Dyes at Opposite Ends Provide a Quenched Probe System Useful for Detecting PCR Product and Nucleic Acid Hybridization", PCR Methods and Application 4:357–362.

Marshall, 1975, "Rules for the Visible Absorption Spectra of Halogenated Fluorescein Dyes", Histochemical J. 7:299–303.

Meyer, 1994, "Incorporation of Modified Bases into Oligonucleotides", in: *Methods in Molecular Biology vol. 26: Protocols for Oligonucleotide Conjugates*, Chapter 2, Agarwal, ed., Humana Press, Totowa, NJ, pp. 73–91.

Mujumdar et al., 1993, "Cyanine Dye Labeling Reagents: Sulfoindocyanine Succinimidyl Esters", Bioconjugate Chem. 4:105–111.

Mullah et al., 1998, "Efficient Synthesis of Double–Dye Labeled Oligonucleotide Probes and Their Application in a Real Time PCR Assay", Nucl. Acids Res. 26:1026–1031.

Mullah and Andrus, 1997, "Automated Synthesis of Double Dye–Labeled Oligonucleotides using Tetramethylrhodamine (TAMRA) Solid Supports", Tetrahedron Lett. 38:5751–5754.

Nielsen et al., 1991, "Sequence–Selective Recognition of DNA by Strand Displacement with a Thymine–Substituted Polyamide", Science 254:1497–1500.

Sturmer, 1977, "Synthesis and Properties of Cyanine and Related Dyes", in: *The Chemistry of Heterocyclic Compounds*, Weissberger and Taylor, eds., pp. 441–601.

Taylor et al., 1997, "Optimization of the Performance of the Polymerase Chain Reaction in Silicon–Based Microstructures", Nucl. Acids Res.25:3164–3168.

Trichtinger et al., 1983, "Synthesis of $O^{6''}$–ρ–Nitrophenylethyl Guanosine and 2'–Deoxyguanosine Derivatives, Tetrahedron Lett. 24:711–714.

Tyagi and Kramer, 1996, "Molecular Beacons: Probes that Fluoresce upon Hybridization", Nature Biotechnol. 14:303–308.

* cited by examiner

5

20

21

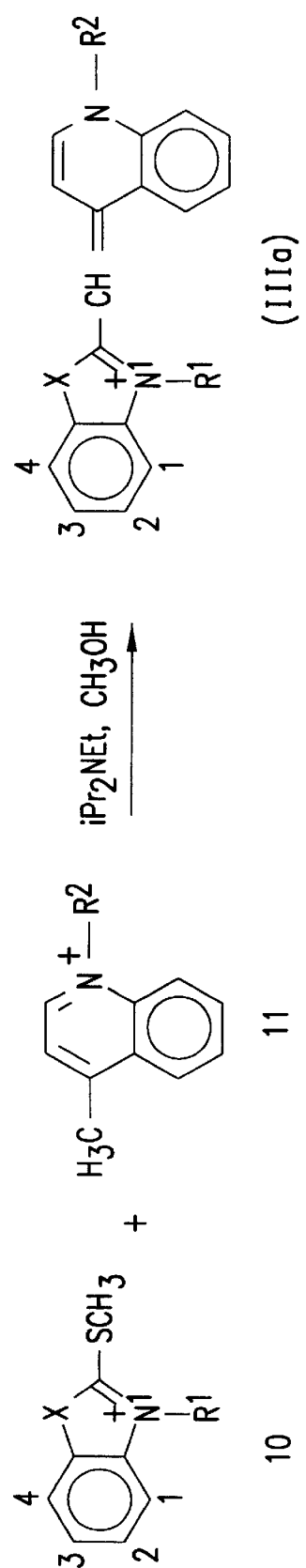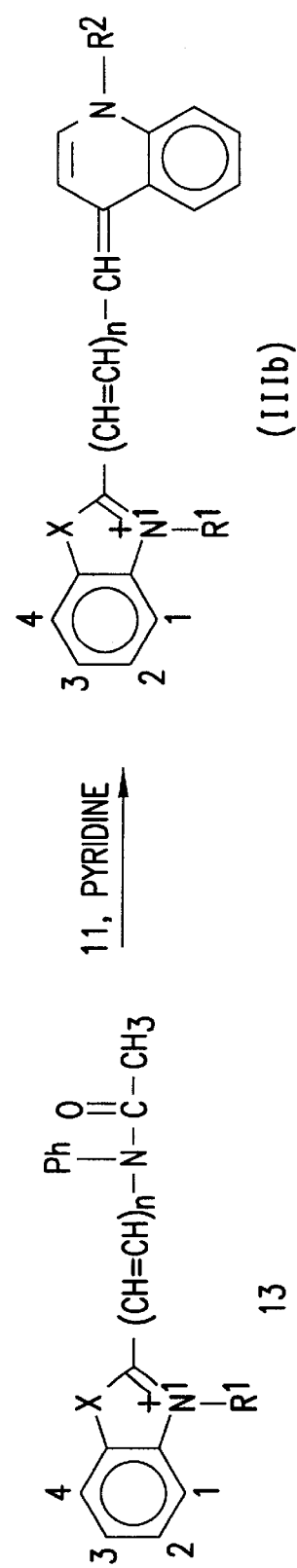
FIG.2A
FIG.2B

NON-FLUORESCENT ASYMMETRIC CYANINE DYE COMPOUNDS USEFUL FOR QUENCHING REPORTER DYES

This is a continuation-in-part of application Ser. No. 09/012,525, filed Jan. 23, 1998, now U.S. Pat. No. 6,080,868, incorporated herein by reference in its entirety.

FIELD OF THE INVENTION

The present invention relates to compounds useful as quenchers in a reporter-quencher energy transfer dye pair. Specifically, the present invention relates to non-radiative cyanine quencher compounds, reagents, such as nucleosides/tides and polynucleotides, incorporating such compounds and methods utilizing such compounds and/or reagents.

BACKGROUND

Nucleic acid hybridization assays comprise an important class of techniques in modern biology. Such assays have diverse applications, including the diagnosis of inherited disease, human identification, identification of microorganisms, paternity testing, virology, and DNA sequencing, e.g., sequencing by hybridization.

An important aspect of nucleic acid hybridization assays is the method used to facilitate detection of the hybridization event. A particularly important class of methods used in nucleic acid hybridization assays employs a reporter-quencher energy-transfer compound pair comprising a "reporter" compound and a "quencher" compound that interact through a fluorescence resonance energy transfer (FRET) process. In these methods, the reporter is a luminescent compound that can be excited either by chemical reaction, producing chemiluminescence, or by light absorption, producing fluorescence. The quencher can interact with the reporter to alter its light emission, usually resulting in the decreased emission efficiency of the reporter. This phenomenon is called quenching. The efficiency of quenching is strongly correlated with the distance between the reporter molecule and the quencher molecule. Thus, in a nucleic acid hybridization assay, detection of a hybridization event is accomplished by designing an energy transfer system in which the spacing between a reporter and a quencher is modulated as a result of the hybridization.

Quencher compounds that are presently used in FRET-based nucleic acid hybridization assays are themselves fluorescent. That is, in addition to quenching the fluorescence of the reporter, the quencher produces fluorescent emissions. This is problematic, particularly in assays employing multiple spectrally resolvable reporters. Because the quencher fluorescence can interfere with the fluorescent signal produced by one or more of the reporters, detection of a hybridization event can be problematic. Accordingly, there remains a continuing need for quencher compounds that are substantially non-fluorescent. In addition, there remains a need for reagents, such as nucleoside/tides and polynucleotides, that incorporate such quencher compounds in order to more reliably monitor, e.g., hybridization events.

SUMMARY OF THE INVENTION

The present invention is directed to Applicants' discovery of a class of non-fluorescent cyanine quencher compounds that are useful in the context of a reporter-quencher energy transfer compound pair. These quencher compounds find particular application in nucleic acid hybridization assays employing fluorescence energy transfer as a means of detection.

In one embodiment, the present invention relates to compounds of formula (I):

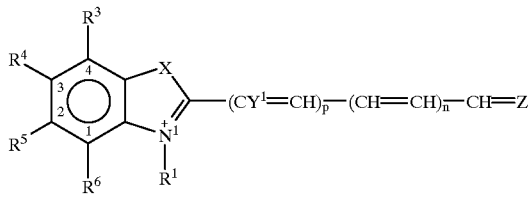

alone or in combination with a counterion thereof, wherein:
p is 0 or 1;
n is 0 or 1;
X is S, Se or O;
$N^1$ is nitrogen;
Z is selected from the group consisting of:

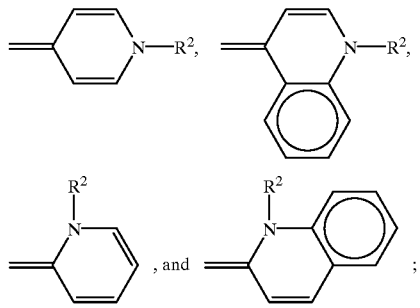

either:
(a) $R^2$ is A, $Y^1$ is H, and $R^1$ is a linking group, or
(b) $R^2$ is a linking group, and:
  (i) $R^1$ is A, or
  (ii) p is 1, and $R^1$ and $Y^1$ taken together are $(CH_2)_q$;
A is selected from the group consisting of alkyl, aryl, —$CH_2$aryl, and —$(CH_2)_m N^+(CH_3)_3$;
q is an integer ranging from 2 to 4;
each m is independently an integer ranging from 2 to 12;
A or $(CH_2)_q$ is unsubstituted or independently substituted with one or more of the same or different —$NO_2$, —OH, alkoxy, —COOH, —$COOC_1$-$C_4$ alkyl, —NHCHO, —$NHCOC_1$-$C_4$ alkyl, —$NHCOCH_3$, —$NHCOCH_2Cl$, —$NHCOCHCl_2$, —$NHCOCCl_3$, —$NHCOCF_3$, —$NHCOCH_2C_6H_4$-o-$NO_2$, —$NHCOCH_2OC_6H_4$-o-$NO_2$, —$NHCOCH_2COCH_3$, —$NHCOCH_2$—$N^+C_5H_5Cl^-$, —$NHCOCH_2NHCS_2CH_2C_6H_5$, —$NHCOCH_2CH_2C_6H_5$, —$NHCOCH_2CH_2C_6H_4$-p-OH, —$NHCOCH_2CH_2C_6H_4$-o-$NO_2$, —$NHCOC(CH_3)_2OC_6H_4$-o-$NO_2$, —$NHCOC(CH_3)_2OC_6H_4$-o-N=$NC_6H_5$, —$NHCO(CH_2)_3Cl$, —$NHCOCH(CH_3)_2$, —$NHCOCH$=$CHC_6H_4$-o-$NO_2$, or —NHCO-2-pyridyl groups; either:
(a) $R^3$, $R^5$ and $R^6$ are H and $R^4$ is —$NO_2$; or
(b) $R^3$ and $R^4$ taken together form a benzo group substituted with one or two —$NO_2$ groups and $R^5$ and $R^6$ are hydrogen; or
(c) $R^4$ and $R^5$ taken together form a benzo group substituted with one or two —$NO_2$ groups and $R^3$ and $R^6$ are hydrogen; or
(d) $R^5$ and $R^6$ taken together form a benzo group substituted with one or two —$NO_2$ groups and $R^3$ and $R^4$ are hydrogen; and with the proviso that when $R^1$ in the compounds of formula (I) has an sp$^3$ hybridized carbon atom that is covalently attached to $N^1$, then that carbon atom is methyl or, when substituted, primary, and protected derivatives thereof.

The compounds of formula (I) are useful as non-fluorescent quenchers. In addition, they are useful in a composition further comprising a reporter dye, which have utility in determining how well matched are the reporter and quencher dyes with each other with respect to the ability of the quencher to quench the fluorescence of the reporter. The compounds of formula (I) are also useful: (i) when linked to a biomolecule, wherein the biomolecule is also linked to a reporter dye; and (ii) when linked to a biomolecule in a composition with a second biomolecule linked to a reporter dye in detecting the presence of a specific nucleotide sequence in a nucleic acid sample, in detecting the presence of contiguous sequences on a target nucleic acid, in detecting the presence of mutations within a target nucleic acid sequence, in monitoring the kinetics of nucleic acid hybridization, and in monitoring the progression of PCR reactions.

In a second embodiment, the present invention relates to compounds of formula (II) NUC—L'—$R^{41}$—L—D alone or in combination with a counterion thereof, wherein: NUC is a nucleoside, a nucleotide, a nucleoside analog, or a nucleotide analog; L' is a bond or a first spacer; $R^{41}$ is a covalent linkage; L is a bond or a second spacer; and D is the chromophore of a compound of formula (I), defined above, and protected derivatives thereof.

The compounds of formula (II) are useful as monomers for the synthesis of biologically relevant molecules, particularly oligonucleotides, that comprise a non-fluorescent quencher dye.

In a third embodiment, the present invention relates to compounds of the formula (III):

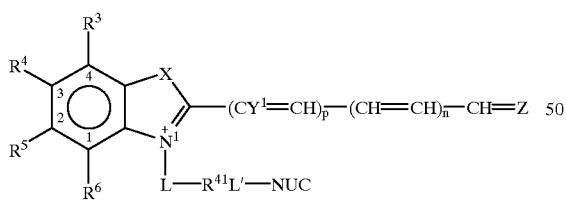

(III)

alone or in combination with a counterion thereof, wherein:

$R^2$–$R^6$, n, p, m, X, Z, NUC, L, L' and $R^{41}$ are defined for formula (I); and $Y^1$ is H, and protected derivatives thereof.

The compounds of formula (III) are useful as monomers for the synthesis of biologically relevant molecules, particularly oligonucleotides, that comprise a non-fluorescent quencher dye.

In a fourth embodiment, the present invention relates to compounds of formula (IV):

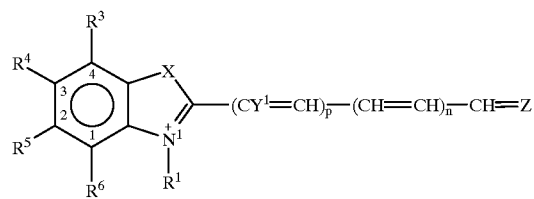

(IV)

alone or in combination with a counterion thereof, wherein:
$R^1$, $R^3$–$R^6$, n, p, X, L, L', $Y^1$, NUC and $R^{41}$ are defined as for formulas (I) and (II); and
Z is selected from the group consisting of:

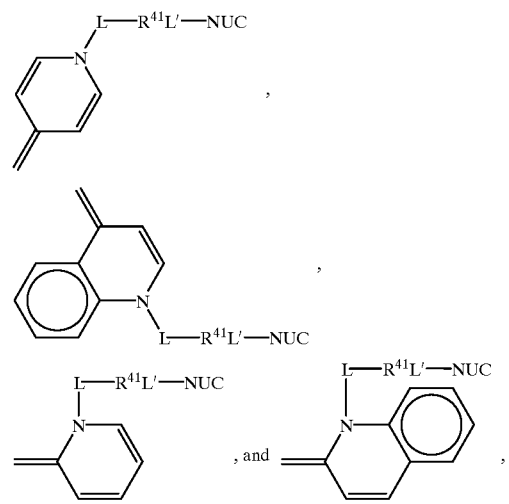

and protected derivatives thereof.

The compounds of formula (IV) are useful as monomers for the synthesis of biologically relevant molecules, particularly oligonucleotides, that comprise a non-fluorescent quencher dye.

In a fifth embodiment, the present invention relates to compounds of formula (V)

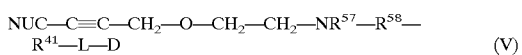

(V)

alone or in combination with a counterion thereof wherein:
NUC and D are defined as for formula (II);
$R^{41}$ is selected from a covalent linkage selected from the group consisting of carboxamides, esters, imines, hydrazones, oximes, alkyl amines, thioethers, ethers, thiophenols, aryl amines, boronate esters, hydrazides, N-acylureas or anhydrides, aminotriazines, triazinyl ethers, amidines, ureas, urethanes, thioureas, phosphite esters, silyl ethers, alkyl amines, sulfonamides, and sulfonate esters; a linkage between a pair of specific binding compounds selected from the group consisting of biotin with avidin, biotin with streptavidin, biotin with anti-biotin, IgG with protein A, IgG with protein G, a drug with a drug receptor, a toxin with a toxin receptor, a carbohydrate with a lectin, a carbohydrate with a carbohydrate receptor, a peptide with a peptide receptor; or a linkage between an anionic group and a cationic group; and
L is selected from the group consisting of bonds, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, and substituted heteroaryl-heteroalkyldiyls;

$R^{57}$ is hydrogen or $(C_1-C_6)$ alkyl; and $R^{58}$ is $-C(O)-(CH_2)_r-$, $-C(O)-CHR^{59}-$, $-C(O)-C\equiv C-CH_2-$ or $-C(O)-\phi-(CH_2)_r-$, where each r is independently an integer from 1 to 5 and $\phi$ is a $C_6$ aryldiyl or a 6-membered heteroaryldiyl, and $R^{59}$ is hydrogen, $(C_1-C_6)$ alkyl, a side chain of a gene-encoded amino acid, or a side chain of a non-encoded amino acids, and protected derivatives thereof.

The compounds of formula (V) are useful as monomers for the synthesis of biologically relevant molecules, particularly oligonucleotides, that comprise a non-fluorescent quencher dye.

In a sixth embodiment, the present invention relates to compounds of formula (VI)

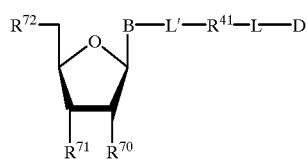

(VI)

alone or in combination with a counterion thereof wherein:

$R^{41}$, L, L', and D are defined as for formula (II);

B is a nucleobase or nucleobase analog;

$R^{70}$ and $R^{71}$ are each independently —H, —OH or a moiety which blocks polymerase-mediated template-directed polymerization; and $R^{72}$ is —OH, or a phosphate ester having the formula

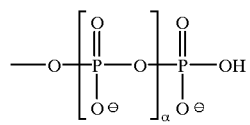

wherein a is an integer from 0 to 2, or a phosphate ester analog, and protected derivatives thereof.

In a seventh embodiment, the present invention relates to compounds of formula (VII):

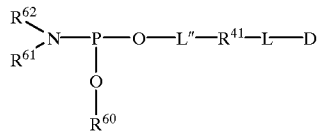

(VII)

alone or in combination with a counterion thereof wherein:

$R^{41}$, L, and D are defined above;

N, O and P represent nitrogen, oxygen and phosphorous, respectively;

L" is selected from the group consisting of bonds, alkyldiyls, substituted alkyldiyls, alkylenos, substituted alkylenos, heteroalkyldiyls, substituted heteroalkyldiyls, heteroalkylenos, substituted heteroalkylenos, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, and substituted heteroaryl-heteroalkyldiyls;

$R^{60}$ is a phosphite ester protecting group;

$R^{61}$, when taken alone, is selected from the group consisting of $(C_1-C_6)$ alkyl, $(C_1-C_6)$ alkanyl, $(C_2-C_6)$ alkenyl, $(C_2-C_6)$ alkynyl, $(C_3-C_{10})$ cycloalkyl, $(C_5-C_{20})$ aryl and $(C_6-C_{26})$ arylalkyl, or when taken together with $R^{62}$ forms a straight-chain or branched $(C_2-C_{10})$ alkyleno or a straight-chain or branched 2–10 membered heteroalkyleno; and $R^{62}$, when taken alone, is selected from the group consisting of $(C_1-C_6)$alkyl, $(C_1-C_6)$ alkanyl, $(C_2-C_6)$ alkenyl, $(C_2-C_6)$ alkynyl, $(C_3-C_{10})$ cycloalkyl, $(C_5-C_{20})$ aryl and $(C_6-C_{26})$ arylalkyl, or when taken together with $R^{61}$ forms a straight-chain or branched $(C_2-C_{10})$ alkyleno or a straight-chain or branched 2–10 membered heteroalkyleno, and protected derivatives thereof.

The compounds of formula (VII) are useful as monomers for the chemical synthesis of biologically relevant monomers that comprise a non-fluorescent quencher dye. The compounds of formula (VII) are also useful for labeling biologically relevant molecules themselves.

In an eighth embodiment, the present invention relates to compounds of formula (VIII):

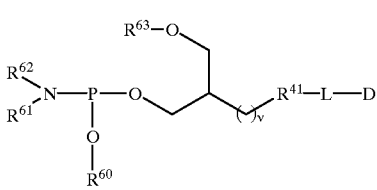

(VIII)

alone or in combination with a counterion thereof wherein:

N, P, O, $R^{41}$, L, D, $R^{60}$, $R^{61}$, and $R^{62}$ are defined above;

$R^{63}$ is hydrogen or an acid-labile hydroxyl protecting group; and v is an integer from 1 to 30, and protected derivatives thereof The compounds of formula (VIII) are useful as monomers for the chemical synthesis of biologically relevant monomers that comprise a non-fluorescent quencher dye. The compounds of formula (VIII) are also useful for labeling biologically relevant molecules themselves.

In a ninth embodiment, the present invention relates to a compound of formula (IX):

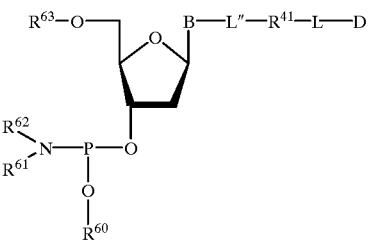

(IX)

alone or in combination with a counterion thereof wherein:
B, $R^{41}$, L, L", D, $R^{60}$, $R^{61}$, $R^{62}$ and $R^{63}$ are defined as for formula (VII),
and protected derivatives thereof.

The compounds of formula (IX) are useful as monomers for the synthesis of biologically relevant molecules, particularly oligonucleotides, that comprise a non-fluorescent quencher dye.

In a tenth embodiment, the present invention relates to compositions comprising a reporter dye and a quencher dye, wherein the quencher dye is a compound of formula (I). Such compositions have utility in determining how well matched are the reporter and quencher dyes with each other with respect to the ability of the quencher to quench the fluorescence of the reporter, in detecting the presence of a specific nucleotide sequence in a nucleic acid sample, in detecting the presence of contiguous sequences on a target nucleic acid, in detecting the presence of mutations within a target nucleic acid sequence, in monitoring the kinetics of nucleic acid hybridization, and in monitoring the progression of PCR reactions.

In an eleventh embodiment, the present invention relates to an oligonucleotide having attached thereto the chromophore of a compound of formula (I). Such attachment can be via a linking group, described below.

Such an oligonucleotide is useful for detecting the presence of a specific nucleotide sequence in a nucleic acid sample, detecting the presence of contiguous sequences on a target nucleic acid, detecting the presence of mutations within a target nucleic acid sequence, monitoring the kinetics of nucleic acid hybridization, and monitoring the progression of PCR reactions.

In a twelfth embodiment, the present invention relates to an oligonucleotide having attached thereto the chromophore of a reporter dye and the chromophore of a compound of formula (I). Such attachment can be via a linking group, described below. Such oligonucleotides are useful for detecting the presence of a specific nucleotide sequence in a nucleic acid sample, detecting the presence of contiguous sequences on a target nucleic acid, detecting the presence of mutations within a target nucleic acid sequence, monitoring the kinetics of nucleic acid hybridization, and monitoring the progression of PCR reactions.

In a thirteenth embodiment, the present invention relates to a composition comprising a first oligonucleotide having attached thereto the chromophore of a compound of formula (I) and a second oligonucleotide having attached thereto the chromophore of a reporter dye. Such attachments can be via a linking group, described below. Such compositions are useful for detecting the presence of a specific nucleotide sequence in a nucleic acid sample, detecting the presence of contiguous sequences on a target nucleic acid, detecting the presence of mutations within a target nucleic acid sequence, monitoring the kinetics of nucleic acid hybridization, and monitoring the progression of PCR reactions.

In a fourteenth embodiment, the present invention relates to a method for detecting a target nucleic acid sequence in a nucleic acid sample, comprising the steps of:
(a) contacting a target nucleic acid sequence with an oligonucleotide probe, wherein the oligonucleotide probe is labeled with: (1) the chromophore of a compound of formula (I); and (2) a reporter dye;
(b) exposing the oligonucleotide probe to light; and
(c) monitoring the change in fluorescence emission of the reporter dye relative to its emission prior to its contacting the target nucleic acid.

In a fifteenth embodiment, the present invention relates to a method for detecting a target nucleic acid sequence in a nucleic acid sample, comprising the steps of:
(a) contacting a target nucleic acid sequence with a first oligonucleotide probe having attached thereto the chromophore of the compound of formula (I); (b) contacting a target nucleic acid sequence with a second oligonucleotide probe having attached thereto a reporter dye;
(b) exposing the oligonucleotide probes to light; and
(c) monitoring the change in fluorescence emission of the reporter dye relative to its emission prior to its contacting the target nucleic acid.

These and other objects, features, and advantages of the present invention will become better understood with reference to the following description, drawings, and appended claims.

BRIEF DESCRIPTION OF THE DRAWINGS

FIGS. 2A and 2B show a generalized synthetic scheme for the synthesis of the cyanine dye quenchers of the present invention.

DETAILED DESCRIPTION OF THE INVENTION

Figure 1A:
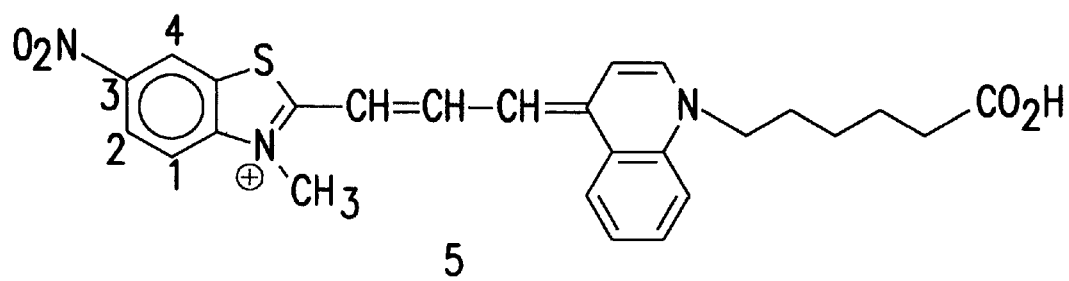
FIGS. 1A and 1B show several preferred cyanine dye compounds of the present invention.
Figure 1A:
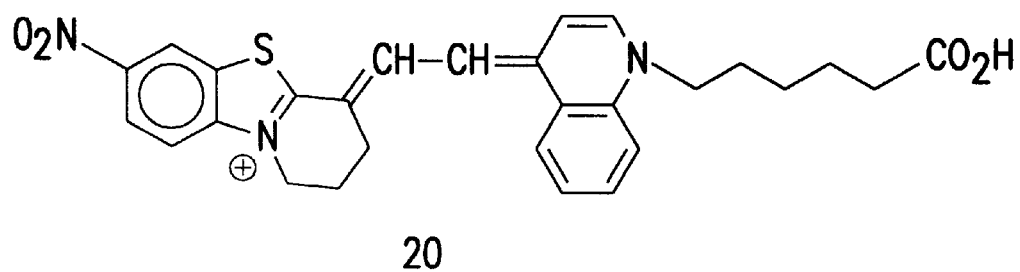
Figure 1A:
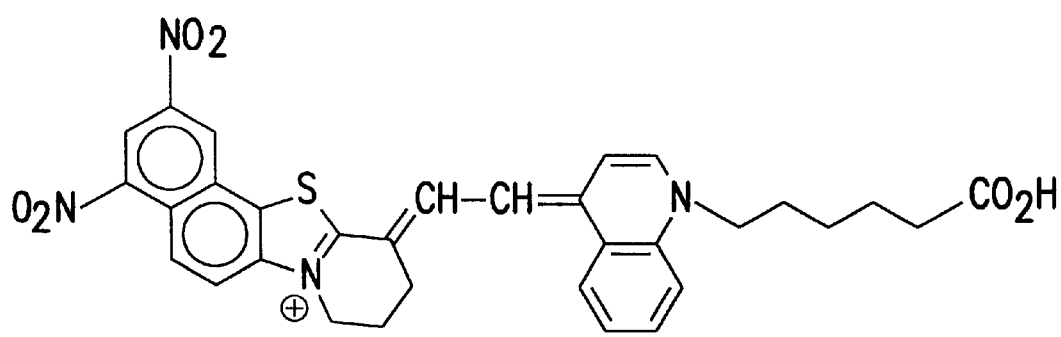
Figure 1B:
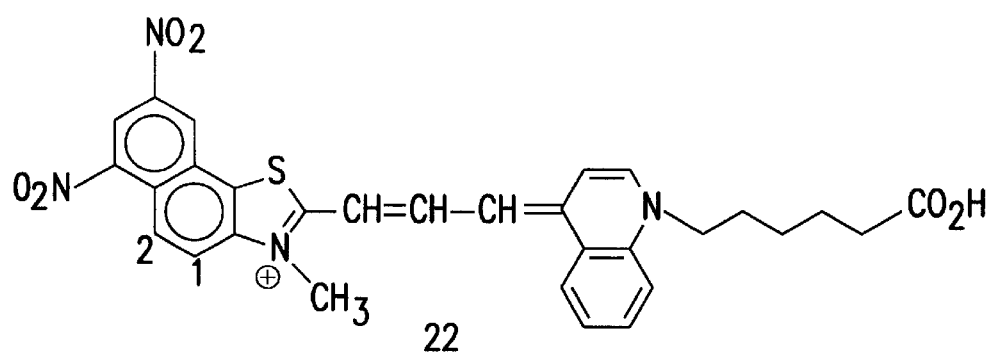
Figure 1B:
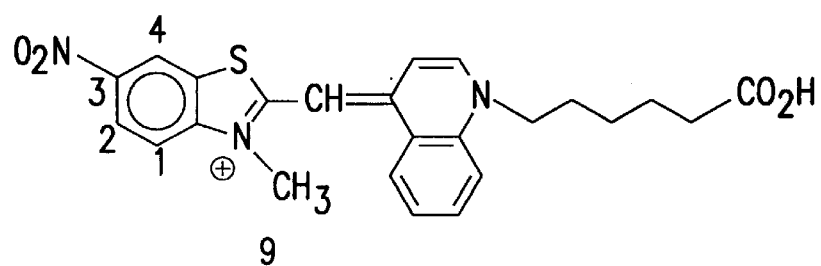
Figure 1B:
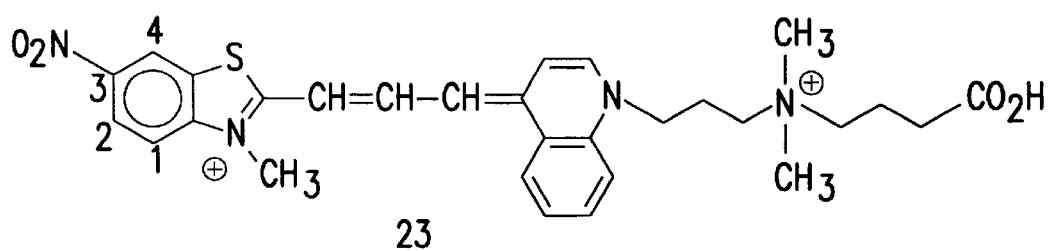

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Abbreviations and Definitions

Abbreviations

The abbreviations used throughout the specification to refer to certain nucleobases and nucleosides/tides are those commonly employed in the art and are as follows:

| Expression | Abbreviation |
| --- | --- |
| adenine | A |
| cytosine | C |
| guanine | G |
| thymine | T |
| uracil | U |
| ribonucleoside-5'-triphosphate | NTP |
| adenosine-5'-triphosphate | ATP |
| cytidine-5'-triphosphate | CTP |
| guanosine-5'-triphosphate | GTP |
| thymidine-5'-triphospate | TTP |
| uridine-5'-triphosphate | UTP |
| 2'-deoxyribonucleoside-5'-triphosphate | dNTP |
| 2'-deoxyriboadenosine-5'-triphosphate | dATP |
| 2'-deoxyribocytidine-5'-triphosphate | dCTP |
| 2'-deoxyriboguanosine-5'-triphosphate | dGTP |
| 2'-deoxyribothymidine-5'-triphospate | dTTP |
| 2'-deoxyribouridine-5'-triphosphate | dUTP |
| 2',3'-dideoxyribonucleoside-5'-triphosphate | ddNTP |
| 2',3'-dideoxyriboadenosine-5'-triphosphate | ddATP |
| 2',3'-dideoxyribocytidine-5'-triphosphate | ddCTP |
| 2',3'-dideoxyriboguanosine-5'-triphosphate | ddGTP |
| 2',3'-dideoxyribothymidine-5'-triphosphate | ddTTP |
| 2',3'-dideoxyribouridine-5'-triphosphate | ddUTP |

Definitions

Unless stated otherwise, the following terms and phrases as used herein are intended to have the following meanings:

"Energy transfer" and "fluorescence quenching" refer to processes whereby energy is transferred from an electronically excited luminescent "reporter" molecule to a "quencher" molecule, thereby returning the reporter molecule to its ground state without the emission of light from the reporter molecule. The reporter molecule may be excited to one of its higher energy levels by any of a number of processes, including light absorption and chemical reaction.

"Spectrally resolvable" means that the fluorescence emission bands of the respective dyes are sufficiently distinct, ie., sufficiently non-overlapping, that the dyes, either alone or when linked to other compounds, e.g., nucleotide/sides, are distinguishable from one another on the basis of their fluorescence signals. The fluorescence emission bands are distinguishable using standard photodetection systems such as photodetectors employing a series of band pass filters and photomultiplier tubes, charged-coupled devices (CCD), spectrographs, etc. (see U.S. Pat. Nos. 4,230,558 and 4,811,218 or Wheeless et al., 1985, *Flow Cytometry: Instrumentation and Data Analysis*, pp. 21–76, Academic Press, New York.) Preferably, all of the dyes comprising a spectrally resolvable set of dyes are excitable by a single light source.

"Linking group" is more fully defined below, but preferably refers to a moiety of a reporter or quencher molecule capable of reacting with a "complementary functionality" of a reagent, e.g., a nucleoside/tide or polynucleotide, and forming a "linkage" that connects the compound to the reagent. When the complementary functionality is amine, preferred linking groups include isothiocyanate, sulfonyl chloride, 4,6-dichlorotriazinyl, carboxylate, succinimidyl ester, other active carboxylate, e.g., —C(O)halogen, —C(O)OC$_1$–C$_4$ alkyl, or —C(O)OC(O)C$_1$–C$_4$ alkyl, amine, lower alkycarboxy or —(CH$_2$)$_m$N$^+$(CH$_3$)$_2$(CH$_2$)$_m$COOH, wherein m is an integer ranging from 2 to 12. In a particularly preferred embodiment, when the complementary functionality is amine, the linking group is a N-hydroxysuccinimidyl (NHS) ester. When the complementary functionality is sulfhydryl, the linking group is preferably maleimide, halo acetyl, or iodoacetamide. See R. Haugland (1992) Molecular Probes Handbook of Fluorescent Probes and Research Chemicals, Molecular Probes, Inc., which discloses myriad dyes and modes for conjugating them to other compounds, and references cited therein.

"Nucleobase" refers to adenine, cytidine, guanine, thymine or uracil.

"Nucleobase analog" refers to a substituted or unsubstituted nitrogen-containing parent heteroaromatic ring that is capable of forming Watson-Crick hydrogen bonds with a complementary nucleobase or nucleobase analog. Preferably, the nucleobase analog is a purine, deazapurine or pyrimidine. Exemplary nucleobase analogs include, but are not limited to, 7-deaza-adenine, inosine, nebularine, nitropyrrole, nitroindole, 2-amino-purine, 2,6-diamino-purine, hypoxanthine, pseudouridine, 5-propynyl-cytidine, isocytidine, isoguanine, 7-deaza-quanine, 2-thio-pyrimidine, 6-thio-guanine, 4-thio-thymine, 4-thio-uracil, O$^6$-methyl-guanine, N$^6$-methyl-adenine, O$^4$-methyl-thymine, 5,6-dihydrothymine, 5,6-dihydrouracil, 4-methyl-indole, ethenoadenine, etc. Additional exemplary nucleobase analogs can be found in Fasman, 1989, *Practical Handbook of Biochemistry and Molecular Biology*, pp. 385–394, CRC Press, Boca Raton, Fla., and the references cited therein.

"Nucleoside" refers to a compound consisting of a nucleobase covalently linked to the C-1' carbon of a substituted or unsubstituted ribose sugar. Typical substituted ribose sugars include, but are not limited to, those in which one or more of its carbon atoms, preferably one and most preferably the 3'-carbon atom, is substituted with one or more of the same or different —R, —OR, —NRR or halogen groups, where each R is independently —H, (C$_1$–C$_6$) alkyl or (C$_5$–C$_4$) aryl. Particularly preferred ribose sugars are ribose, 2'-deoxyribose, 2',3'-dideoxyribose, 3'-haloribose, 3'-fluororibose, 3'-chlororibose, 3'-alkylribose, etc.

When the nucleobase is A or G, the ribose sugar is attached to the N$^9$-position of the nucleobase. Where the nucleobase is C, T or U, the pentose sugar is attached to the N$^1$-position of the nucleobase (see, e.g., Kornberg and Baker, 1992, *DNA Replication*, 2$^{nd}$ Ed., Freeman, San Francisco).

"Nucleoside analog" refers to a nucleoside in which the nucleobase, the ribose sugar, or both, are replaced with their respective analogs. Exemplary nucleobase analogs are those previously defined. Exemplary ribose sugar analogs include, but are not limited to, substituted or unsubstituted furanoses having more or fewer than 5 ring atoms, e.g., erythroses and hexoses and substituted or unsubstituted 3–6 carbon acyclic sugars. Typical substituted furanoses and acyclic sugars are those in which one or more of the carbon atoms are substituted with one or more of the same or different —R, —OR, —NRR or halogen groups, where each R is independently —H, (C$_1$–C$_6$) alkyl or (C$_5$–C$_{14}$) aryl.

"Nucleotide" refers to a nucleoside in which one or more, typically one, of the ribose carbons is substituted with a phosphate ester having the formula:

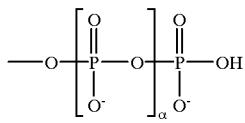

where a is an integer from 0 to 4. Preferably, a is 2 and the phosphate ester is attached to the 3'- or 5'-carbon of the ribose, e.g., ribose-3'-triphosphate, 2'-deoxyribose-3'-triphosphate, ribose-5'-triphosphate, 2'-deoxyribose-5'-triphosphate, 3'-haloribose-5'-triphosphate, 3'-alkylribose-5'-triphosphate, 2',3'-dideoxyribose-5'-triphosphate, etc.

"Nucleotide analog" refers to a nucleotide in which the nucleobase, the ribose sugar and/or one or more of the phosphate esters is replaced with a respective analog. Exemplary nucleobase and ribose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, peptide nucleic acid (PNA) monomers, etc., including any associated counterions, if present.

"Enzymatically extendable nucleotide or nucleotide analog" refers to a nucleotide or nucleotide analog that is capable of acting as a substrate for a polymerizing enzyme, enabling it to be enzymatically incorporated into a nascent polynucleotide chain. Typically, enzymatically extendable nucleotides or nucleotide analogs are nucleotides and nucleotide analogs, respectively, in which the furanose of the nucleotide or nucleotide analog is a pentose-5'-triphosphate, e.g., ribose-5'-triphosphate, 2'-deoxyribose-5'-triphosphate, 3'-haloribose-5'-triphosphate, 3'-alkylribose-5'-triphosphate, 2',3'-dideoxyribose-5'-triphosphate, etc.

"Terminator" refers to an enzymatically extendable nucleotide or nucleotide analog in which the ribose sugar or sugar analog does not contain a hydroxyl group available for further polymerization. Preferred terminators are enzymatically extendable 2',3'-dideoxyribonucleotides, 2',3'-dideoxyribonucleotide analogs, 3'-haloribonucleotides, 3'-haloribonucleotide analogs, 3'-alkylribonucleotides and 3'-alkylribonucleotide analogs, particularly those in which the nucleobase is adenine, 7-deaza-adenine, cytidine, guanine, 7-deaza-guanine, thymine and uracil.

"Nucleoside/tide" refers to nucleosides and/or nucleotides and/or mixtures thereof.

"Polynucleotide" refers to a linear polymeric chain of nucleoside monomer units that are covalently connected to one another by phosphate ester internucleoside linkages. Unless stated otherwise, "polynucleotide" as used herein includes polymers of any length, including oligonucleotides, polynucleotides and nucleic acids as those terms are commonly used in the art. Where polynucleotides of specific size ranges are intended, the number of monomer units is specifically delineated. Thus, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g., "ATGCCTG," it will be understood that the sequence is presented in the 5'→3' direction.

2'-Deoxyribopolynucleotides are preceded with the letter "d" and expressed parenthetically, e.g., "d(ATGCCTG)."

"Polynucleotide analog" refers to a polynucleotide in which at least one nucleoside monomer unit is a nucleoside analog and/or at least one phosphate ester internucleoside linkage is a phosphate ester analog, as defined above under "nucleotide analog". Preferred classes of polynucleotide analogs are those in which the sugar and internucleoside linkages are replaced with an uncharged, neutral amide, such as a morpholino-carbamate and peptide nucleic acids ("PNA"). Preferred PNAs are those having a N-(2-aminoethyl)-glycine amide backbone (see, e.g., Nielsen et al., 1991, Science 254:1497–1500). PNA sequences represented as a sequence of letters are preceded with the letter "p" and expressed parenthetically, e.g., "p(ATGCCTG)." In such representations, it is understood that the amino terminus is at the left-hand side (equivalent to the 5' end in polynucleotides) and the carboxyl terminus is at the right-hand side (equivalent to the 3' end in polynucleotides).

"Labeled nucleoside/tide, nucleoside/tide analog, polynucleotide polynucleotide analog or terminator" refers to a nucleoside/tide, nucleoside/tide analog polynucleotide, polynucleotide analog or terminator which has a fluorescent dye or quencher dye covalently attached to either the nucleobase or the sugar moiety.

"Reagent" refers to any molecule or substance to which the dyes of the invention can be conjugated, including by way of example and not limitation, proteins, polypeptides, polysaccharides, nucleosides, nucleotides, polynucleotides, lipids, solid supports, organic and inorganic polymers, and combinations and assemblages thereof, such as chromosomes, nuclei, living cells (e.g., bacteria or other microorganisms, mammalian cells, tissues, etc.), and the like.

"Methine bridge" refers to a portion of a cyanine dye compound connecting two heterocyclic moieties, the bridge having the following structure

where n is typically 0.

"Polymethine bridge" is where n is 1 or 2. Each —(CH=CH)— of —(CH=CH)$_n$—CH— can exist in either a cis or trans configuration.

"Isothiocyanate" has the structure —N=C=S.

"Sulfonyl chloride" has the structure —SO$_2$Cl.

"4,6-Dichlorotriazinyl" has the structure:

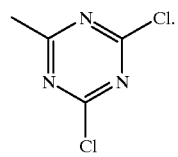

"Succinimidyl ester" has the structure:

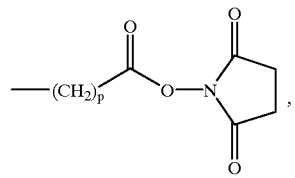

wherein p is an integer ranging from 0 to 12.

"Active carboxylate" is a carbonyl group having a leaving group and includes —C(O)halogen, —C(O)OC$_1$–C$_4$ alkyl, and —C(O)OC(O)C$_1$–C$_4$ alkyl.

"Carboxylate" has the structure —COO⁺M⁺, wherein M⁺ is a counterion.

"Counterion" refers to an ion that is stable and synthetically accessible. As used herein, a substance that is biologically compatible is not toxic as used, and does not have a substantially deleterious effect on biomolecules. Examples of counterions include (but are not limited to) chloride, bromide, iodide, sulfate, benzene sulfonate, p-toluenesulfonate, p-bromobenzenesulfonate, methanesulfonate, trifluoromethanesulfonate, phosphate, perchlorate, tetrafluoroborate, tetraphenylboride, nitrate and anions of aromatic or aliphatic carboxylic acids. Preferred counterions are chloride, iodide, perchlorate and the sulfonates listed above.

"Amine," when used as an example of a linking group, has the structure —(CH$_2$)$_r$NH$_2$, wherein r is an integer ranging from 1 to 8.

"Maleimide" has the structure:

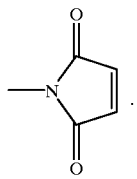

"Halo acetyl" has the structure —C(O)CH$_2$halogen.
"Iodoacetamide" has the structure —NHC(O)CH$_2$I.
"Lower alkycarboxy" has the structure —(CH$_2$)$_r$COOH.
"Alkoxy" means —O-alkyl.

"Cyanine dyes" are compounds comprising two nitrogen-containing rings joined by a methine, or polymethine, bridge. Examples of cyanine dyes are found in Ficken (1971) *The Chemistry of Synthetic Dyes, Vol. IV*, (Venkataraman).

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl , prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C$_1$–C$_6$) alkyl, with (C$_1$–C$_3$) being particularly preferred.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl, 2-methyl-propan-1-yl (isobutyl), 2-methyl-propan-2-yl (t-butyl), cyclobutan-1-yl, etc.; and the like. In preferred embodiments, the alkanyl groups are (C$_1$–C$_6$) alkanyl, with (C$_1$–C$_3$) being particularly preferred.

"Alkenyl" refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl , prop-1-en-2-yl, prop-2-en-1-yl, prop-2-en-2-yl, cycloprop-1-en-1-yl; cycloprop-2-en-1-yl ; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C$_2$–C$_6$) alkenyl, with (C$_2$–C$_3$) being particularly preferred.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propenyls such as prop-1-en-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C$_2$–C$_6$) alkynyl, with (C$_2$–C$_3$) being particularly preferred.

"Alkyldiyl" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is (C$_1$–C$_6$) alkyldiyl, with (C$_1$–C$_3$) being particularly preferred. Also preferred are saturated acyclic alkanyldiyl radicals in which the radical centers are at the terminal carbons, e.g., methandiyl (methano); ethan-1,2-diyl (ethano); propan-1,3-diyl (propano); butan-1,4-diyl (butano); and the like (also referred to as alkylenos, as defined infra).

"Vic Alkyldiyl" refers to an alkyldiyl radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2- diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is ($C_2$–$C_6$) vic alkyldiyl, with ($C_2$–$C_3$) being particularly preferred.

"Gem Alkyldiyl" refers to an alkyldiyl radical having one divalent radical center derived by the removal of two hydrogen atoms from a single carbon atom of a parent alkane, alkene or alkyne. Each valency of the divalent radical center forms bonds with two different atoms. Typical gem alkyldiyls include, but are not limited to gem methanyldiyl; gem ethyldiyls such as ethan-1,1-diyl,ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methanylidene-propan-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is ($C_1$–$C_6$) gem alkyldiyl, with ($C_1$–$C_3$) being particularly preferred.

"Alkyleno" refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno (—C≡C—); propylenos such as propano, prop(1)eno, propa(1,2)dieno, prop(1)yno, etc.; butylenos such as butano, but(1)eno, but(2)eno, buta(1,3)dieno, but(1)yno, but(2)yno, but(1,3)diyno, etc.; and the like. Where specific levels of saturation are intended, the nomenclature alkano, alkeno and/or alkyno is used. In preferred embodiments, the alkyleno group is ($C_1$–$C_6$) alkyleno, with ($C_1$–$C_3$) being particularly preferred. Also preferred are straight-chain saturated alkano radicals, e.g., methano, ethano, propano, butano, and the like.

"Alkylidene" refers to an alkyldiyl radical having one divalent radical center derived by removal of two hydrogen atoms from the same carbon atom of a parent alkane, alkene or alkyne. Each valency of the divalent radical center forms a bond with the same atom, ie., the divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene (isopropylidene), cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene (iosbutylidene), cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is ($C_1$–$C_6$) alkylidene, with ($C_1$–$C_3$) being particularly preferred.

"Heteroalkyl, heteroalkanyl, heteroalkenyl, heteroalkynyl, heteroalkylidene, heteroalkyldiyl, vic heteralkyldiyl, gem heteroalkyldiyl and heteroalkyleno" refer to alkyl, alkanyl, alkenyl, alkynyl, alkylidene, alkyldiyl, vic alkyldiyl, gem alkyldiyl and alkyleno radicals, respectively, in which one or more carbon atoms (and any necessary associated hydrogen atoms) are each independently replaced with the same or different heteroatoms (including any necessary hydrogen or other atoms). Typical heteroatoms to replace the carbon atom(s) include, but are not limited to, N, P, O, S, Si, etc. Thus, heteroalkyl, heteroalkanyl, heteroalkenyl, heteroalkynyl, heteroalkylidene, heteroalkyldiyl, vic heteroalkyldiyl, gem heteroalkyldiyl and heteroalkyleno radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfa no (—$SH_2$—), sulfonyl (—S(O)$_2$—), and the like, where each R' is independently hydrogen or ($C_1$–$C_6$) alkyl.

"Acyclic heteroatomic bridge" refers to a divalent bridge in which the backbone atoms are exclusively the same or different heteroatoms, e.g., O, S, N, P, Si, Se, etc. Typical heteroatomic bridges include, but are not limited to, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfa no (—$SH_2$—), sulfonyl (—S(O)$_2$—), and the like, and combinations thereof, where each R' is independently hydrogen or ($C_1$–$C_6$) alkyl.

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$–$C_{20}$) aryl, with ($C_5$–$C_{10}$) being even more preferred. Particularly preferred aryls are phenyl and naphthyl.

"Aryldiyl" refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryldiyl group is ($C_5$–$C_{20}$) aryldiyl, with ($C_5$–$C_{10}$) being even more preferred. The most preferred aryldiyl groups are divalent radicals derived from benzene and naphthalene, especially phen-1, 4-diyl, naphth-2,6-diyl and naphth-2,7-diyl.

"Aryleno" refers to an aryldiyl radical having two adjacent monovalent radical centers radical derived by the removal of one hydrogen atom from each of two adjacent carbon atoms of a parent cyclic or polycyclic aromatic ring system. The two monovalent radical centers each from bonds with different atoms. Typical aryleno groups include, but are not limited to, aceanthryleno, acenaphthyleno, acephenanthryleno, anthraceno, azuleno, benzeno (benzo), chryseno, coroneno, fluorantheno, fluoreno, hexaceno, hexapheno, hexaleno, as-indaceno, s-indaceno, indeno, naphthaleno (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridged carbon atoms are denoted in brackets, e.g., (1,2)benzeno ((1,2)benzo), (3,4)naphthyleno ((3,4)naphtho), (3,4)aceanthryleno, (8,9)aceanthryleno, etc. In preferred embodiments, the aryleno group is ($C_5$–$C_{20}$) aryleno, with ($C_5$–$C_{10}$) being even more preferred. The most preferred aryleno groups are benzo and naphtho.

"Arylaryl" refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenylnaphthyl, binaphthyl, biphenyl-naphthyl, and the like. Where the number of carbon atoms in an arylaryl group are specified, the numbers refer to the carbon atoms comprising each parent aromatic ring. For example, ($C_5$–$C_{20}$) arylaryl is an arylaryl group in which each aromatic ring comprises from 5 to 20 carbons, e.g., biphenyl, triphenyl, binaphthyl, phenylnaphthyl, etc. Preferably, each parent aromatic ring system of an arylaryl group is independently a ($C_5$–$C_{20}$) aromatic, more preferably a ($C_5$–$C_{10}$) aromatic. Also preferred are arylaryl groups in which all of the parent aromatic ring systems are identical, e.g., biphenyl, triphenyl, binaphthyl, trinaphthyl, etc.

"Biaryl" refers to an arylaryl radical having two identical parent aromatic systems joined directly together by a single bond. Typical biaryl groups include, but are not limited to, biphenyl, binaphthyl, bianthracyl, and the like. Preferably, the aromatic ring systems are ($C_5$–$C_{20}$) aromatic rings, more preferably ($C_5$–$C_{10}$) aromatic rings. A particularly preferred biaryl group is biphenyl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$–$C_{26}$) arylalkyl, e.g., the alkanyl, alkenyl or alkynyl moiety of the arylalkyl group is ($C_1$–$C_6$) and the aryl moiety is ($C_5$–$C_{20}$). In particularly preferred embodiments the arylalkyl group is ($C_6$–$C_{13}$), e.g., the alkanyl, alkenyl or alkynyl moiety of the arylalkyl group is ($C_1$–$C_3$) and the aryl moiety is ($C_5$–$C_{10}$).

"Arylheteroalkyl" refers to an acyclic heteroalkyl radical in which one of the hydrogen atoms bonded to a carbon or heteroatom, typically a terminal carbon or heteroatom, is replaced with an aryl radical. Where arylheteroalkyl moieties having specified levels of saturation intended, the nomenclature aryl heteroalkanyl, aryl heteroalkenyl and/or aryl heteroalkynyl is used. In preferred embodiments, the arylheteroalkyl group is a 6–26 membered arylheteroalkyl, e.g., the heteroalkyl moiety is 1–6 membered and the aryl moiety is ($C_6$–$C_{20}$) aryl. In particularly preferred embodiments, the arylheteroalkyl group is 6–13 membered, e.g., the heteroalkyl moiety is 1–3 membered and the aryl moiety is ($C_5$–$C_{10}$).

"Parent heteroaromatic ring system" refers to a parent aromatic ring system in which one or more carbon atoms (and any associated hydrogen atoms) are each independently replaced with the same or different heteroatom. Typical heteratoms to replace the carbon atoms include, but are not limited to, N, P, O, S, Si, etc. (Including and associated hydrogen or other atoms). Specifically included within the definition of "parent heteroaromatic ring systems" are fused ring systems in which one or more of the rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–20 membered heteroaryl, with 5–10 membered heteroaryl being particularly preferred.

"Heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryldiyl group is 5–20 membered heteroaryldiyl, with 5–10 membered being particularly preferred.

"Heteroaryleno" refers to a heteroalkydiyl radical having two adjacent monovalent radical centers derived by the removal of one hydrogen atom from each of two adjacent atoms of a parent heteroaromatic ring system. Each monovalent radical center forms a bond with a different atom. Typical heteroaryleno groups include, but are not limited to, acridino, carbazolo, β-carbolino, chromeno, cinnolino, furano, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, and the like. Where a specific connectivity is intended, the involved bridged atoms are denoted in brackets, e.g., (3,4)furano, (5,6)isoindoleno, (2,3)pyridino, (3,4)pyridino, etc. In preferred embodiments, the heteroaryleno group is a 5–20 membered heteroaryleno, with 5–10 membered heteroarylenos being particularly preferred.

"Heteroaryl-heteroaryl" refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Where the number of atoms are specified, the numbers refer to the number of atoms comprising each parent heteroatomatic ring systems. For example, 5–20 membered heteroaryl-heteroaryl is a heteroaryl-heteroaryl group in which each parent heteroaromatic ring system comprises from 5 to 20 atoms. Preferably, each parent heteroaromatic ring system is independently a 5–20 membered heteroaromatic, more preferably a 5–10 membered heteroaromatic.

"Biheteroaryl" refers to a heteroaryl-heteroaryl radical having two identical parent heteroaromatic ring systems joined directly together by a single bond. Preferably, the heteroaromatic ring systems are 5–20 membered heteroaromatic rings, more preferably 5–10 membered heteroaromatic rings.

"Heteroarylalkyl" refers to an acyclic alkyl radical in which one of the hydrogen atoms bonded to a carbon atom, typically a terminal or sp³ carbon atom, is replaced with a heteroaryl radical. Where specific alkyl moieties are intended, the nomenclature heteroarylalkanyl, heteroarylakenyl and/or heterorylalkynyl is used. In preferred embodiments, the heteroarylalkyl group is a 6–26 membered heteroarylalkyl, e.g., the alkanyl, alkenyl or alkynyl moiety of the heteroarylalkyl is 1–6 membered and the heteroaryl moiety is a 5–20-membered heteroaryl. In particularly preferred embodiments, the heteroarylalkyl is a 6–13 membered heteroarylalkyl, e.g. the alkanyl, alkenyl or alkynyl moiety is 1–3 membered and the heteroaryl moiety is a 5–10 membered heteroaryl.

"Heteroaryl-heteroalkyl" refers to an acyclic heteroalkyl radcial in which one of the hydrogen atoms bonded to a carbon or heteroatom, typically a terminal carbon or heteroatom, is replaced with a heteroaryl radical. Where heteroaryl-heteroalkyl moieties having specified levels of saturation are intended, the nomenclature heteroaryl-heteroalkanyl, heteroaryl-heteroalkenyl or heteroaryl-heteroalkynyl is used. In preferred embodiments, the heteroaryl-heteroalkyl group is 6–26 membered, e.g., the heteroalkyl moiety is 1–6 membered and the heteroaryl moiety is 5–20 membered. In particularly preferred embodiments, the heteroaryl-heteroalkyl is 6–13 membered, e.g., the heteroalkyl moiety is 1–3 membered and the heteroaryl moiety is 5–10 membered.

"Substituted" refers to a radical in which one or more hydrogen atoms are each independently replaced with the same or different substituent(s). Typical substituents include, but are not limited to, alkoxy, —X, —R, —O⁻, =O, —OR, —O—OR, —SR, —S⁻, =S, —NRR, =NR, —CX₃, —CN, —OCN, —SCN, —NCO, —NCS, —NHCHO, —NHCOC₁–C₄alkyl, —NHCOCH₃, —NHCOCH₂Cl, —NHCOCHCl₂, —NHCOCCl₃, —NHCOCF₃, —NHCOCH₂C₆H₄-o-NO₂, —NHCOCH₂OC₆H₄-o-NO₂, —NHCOCH₂COCH₃, —NHCOCH₂—N⁺C₅H₅Cl⁻, —NHCOCH₂NHCS₂CH₂C₆H₅, —NHCOCH₂CH₂C₆H₅, —NHCOCH₂CH₂C₆H₄-p-OH, —NHCOCH₂CH₂C₆H₄-o-NO₂, —NHCOC(CH₃)₂OC₆H₄-o-NO₂, —NHCOC(CH₃)₂OC₆H₄-o-N=NC₆H₅, —NHCO(CH₂)₃Cl, —NHCOCH(CH₃)₂, —NHCOCH=CHC₆H₄-o-NO₂, —NHCO-2-pyridyl, —NO, —NO₂, =N₂, —N₃, —NHOH, —S(O)₂O⁻, —S(O)₂OH, —S(O)₂R, —P(O)(O⁻)₂, —P(O)(OH)₂, —C(O)R, —C(O)X, —C(S)R, —C(S)X, —COOH, —C(O)OR, —C(O)O⁻, —C(S)OR, 13 C(O)SR, —C(S)SR, —C(O)NRR, —C(S)NRR and —C(NR)NRR, where each X is independently a halogen (preferably —F, —Cl or —Br) and each R is independently —H, alkyl, lower alkyl, alkenyl, alkynyl, aryl, arylalkyl, arylheteroalkyl heteroaryl, heteroarylalkyl or heteroaryl-heteroalkyl, as defined herein. Preferred substituents include alkanyl.

"Reporter dye" refers to a compound which, when exposed to light, emits energy.

"The chromophore of a reporter dye" is the network of atoms of the reporter dye that, when exposed to radiation, emits radiation at a level that is detectable by conventional spectroscopic means.

In a preferred embodiment, the chromophore of a reporter dye is:

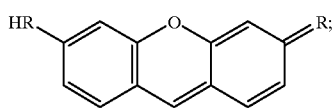

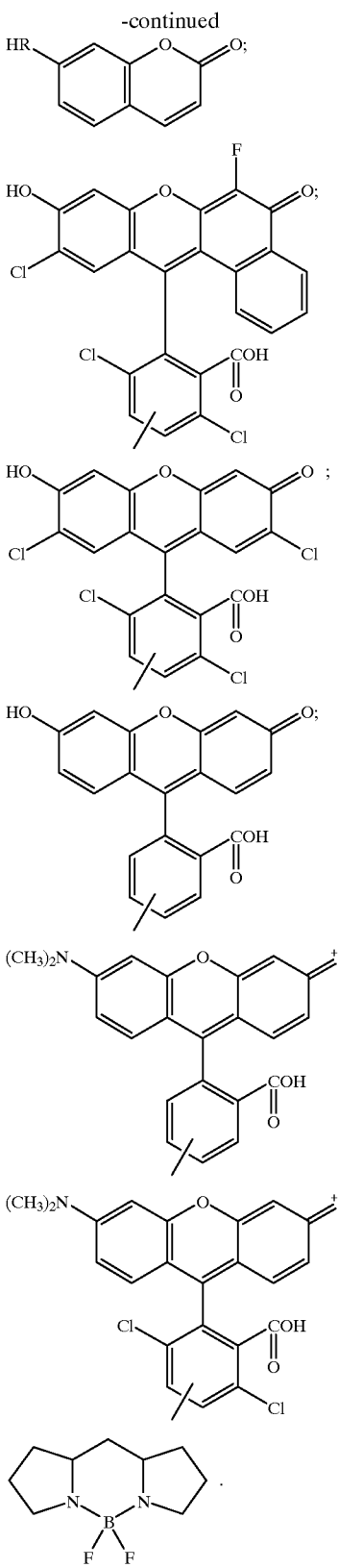

that is attached to a nucleic acid via —L'—R$^{41}$—L—, as defined above.

"The chromophore of a compound of formula (I)" is the network of atoms of the compound of formula (I) that is responsible for the ability of the compound to quench the fluorescence of the chromophore of a reporter without emitting radiation at a level that is detectable by conventional spectroscopic means.

In a preferred embodiment, the chromophore of a compound of formula (I) has the structure of formula (X):

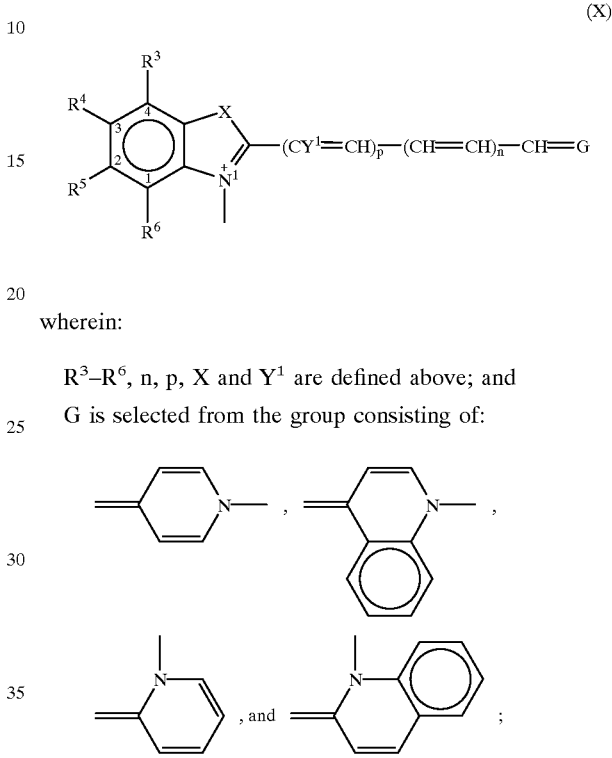

wherein:

$R^3$–$R^6$, n, p, X and $Y^1$ are defined above; and

G is selected from the group consisting of:

that is attached to a nucleic acid via —L'—R$^{41}$—L—, as defined above at either $N^1$ or at the N atom of G. When linked to the nucleic acid at $N^1$, then the N atom of G is linked to A, as defined above; when linked to the nucleic acid at the N atom of G, then $N^1$ is linked to A, as defined above.

"Non-fluorescent" refers to a compound that, when exposed to radiation, does not emit radiation at a level that is detectable by conventional spectroscopic means.

"Reporter quencher energy transfer dye pair" includes: (i) a composition comprising a quencher dye and a reporter dye; (ii) a biomolecule to which is attached a reporter dye and a quencher dye; and (iii) a composition comprising a first biomolecule to which is attached a reporter dye and a second biomolecule to which is attached a quencher dye.

"Biologically relevant" compounds are those substances whose presence and proper function are necessary for maintaining the life of an organism and include peptides, proteins, enzymes, polynucleotides, polysaccharides, and lipids, all of which contain at least one repeat unit of the chromophore of a compound of formula (I).

"Light" refers to electromagnetic energy having a wavelength which causes a reporter dye to fluoresce, wherein that wavelength may be in the range of 190–800 nm.

"Primary carbon atom" refers to a carbon atom having attached thereto one alkyl chain.

Asymmetric Cyanine Dye Compounds

Structure

In a first aspect, the present invention comprises a novel class of cyanine dye compounds useful as nonfluorescent quenchers. The compounds of the present invention have the general structure shown in formula (I):

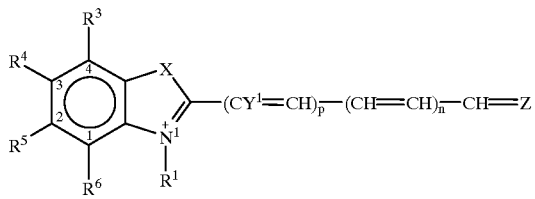

(I)

alone or in combination with a counterion thereof, wherein:

p is 0 or 1;
n is 0 or 1;
X is S, Se or O;
$N^1$ is nitrogen;
Z is selected from the group consisting of:

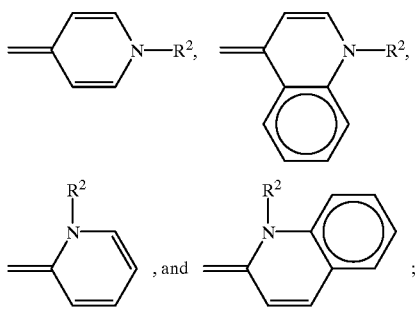

either:
(a) $R^2$ is A, $Y^1$ is H, and $R^1$ is a linking group, or
(b) $R^2$ is a linking group, and:
 (i) $R^1$ is A, or
 (ii) p is 1, and $R^1$ and $Y^1$ taken together are $(CH_2)_q$;
A is selected from the group consisting of alkyl, aryl, —$CH_2$aryl, and —$(CH_2)_mN^+(CH_3)_3$;
q is an integer ranging from 2 to 4;
each m is independently an integer ranging from 2 to 12;
A or $(CH_2)_q$ is unsubstituted or independently substituted with one or more of the same or different —$NO_2$, —OH, alkoxy, —COOH, —$COOC_1$-$C_4$ alkyl, —NHCHO, —$NHCOC_1$-$C_4$ alkyl, —$NHCOCH_3$, —$NHCOCH_2Cl$, —$NHCOCHCl_2$, —$NHCOCCl_3$, —$NHCOCF_3$, —$NHCOCH_2C_6H_4$-o-$NO_2$, —$NHCOCH_2OC_6H_4$-o-$NO_2$, —$NHCOCH_2COCH_3$, —$NHCOCH_2$—$N^+C_5H_5Cl^-$, —$NHCOCH_2NHCS_2CH_2C_6H_5$, —$NHCOCH_2CH_2C_6H_5$, —$NHCOCH_2CH_2C_6H_4$-p-OH, —$NHCOCH_2CH_2C_6H_4$-o-$NO_2$, —NHCOC$(CH_3)_2$ $OC_6H_4$-o-$NO_2$, —$NHCOC(CH_3)_2OC_6H_4$-o-N=$NC_6H_5$, —$NHCO(CH_2)_3Cl$, —$NHCOCH(CH_3)_2$, —$NHCOCH$=$CHC_6H_4$-o-$NO_2$, or —NHCO-2-pyridyl groups; either:
(a) $R^3$, $R^5$ and $R^6$ are H and $R^4$ is —$NO_2$; or
(b) $R^3$ and $R^4$ taken together form a benzo group substituted with one or two —$NO_2$ groups and $R^5$ and $R^6$ are hydrogen; or
(c) $R^4$ and $R^5$ taken together form a benzo group substituted with one or two —$NO_2$ groups and $R^3$ and $R^6$ are hydrogen; or
(d) $R^5$ and $R^6$ taken together form a benzo group substituted with one or two —$NO_2$ groups and $R^3$ and $R^4$ are hydrogen;

with the proviso that when $R^1$ in the compounds of formula (I) has an $sp^3$ hybridized carbon atom that is covalently attached to $N^1$, then that carbon atom is methyl or, when substituted, primary, and protected derivatives thereof.

In a preferred embodiment, the compounds of formula (I) have $R^1$=alkyl, and particularly alkanyl. In another preferred embodiment, $R^1$ and $Y^1$ taken together are $(CH_2)_q$ wherein q is an integer ranging from 2 to 4, and q is 3.

A preferred class of the compounds of formula (I) have the structure of formula (XI):

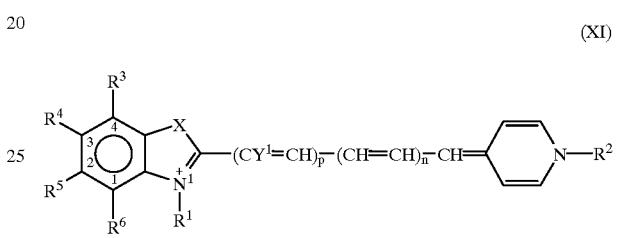

(XI)

the compound of formula (XI) existing alone or in combination with a counterion thereof, wherein $R^1$–$R^6$, X, $Y^1$, p and n are as defined above.

Another preferred class of the compounds of formula (I) have the structure of formula (XII):

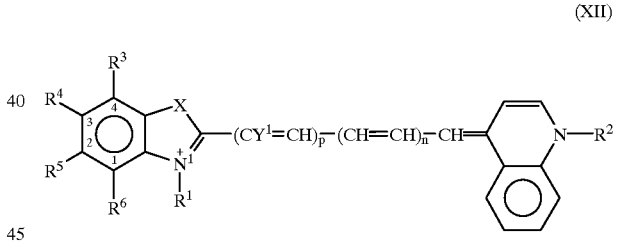

(XII)

the compounds of formula (XII) existing alone or in combination with a counterion thereof, wherein $R^1$–$R^6$, X, $Y^1$, p and n are as defined above.

A preferred class of compounds of formula (XII) have the structure of formula (XIII):

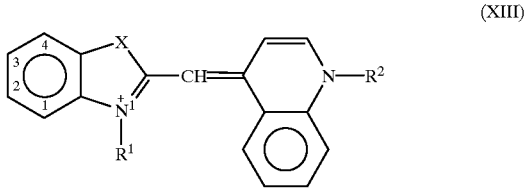

(XIII)

the compound of formula (XIII) existing alone or in combination with a counterion thereof, wherein $R^1$, $R^2$, and X are defined above.

Another preferred class of compounds of formula (XII) has the structure of formula (XIV):

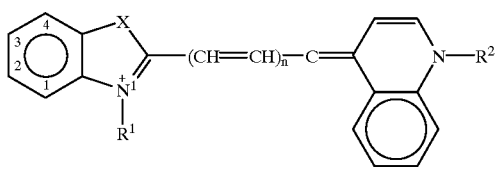
(XIV)

the compound of formula (XIV) existing alone or in combination with a counterion thereof, wherein n, $R^1$, $R^2$, and X are defined above.

Another preferred class of compounds of formula (I) has the structure of formula (XV):

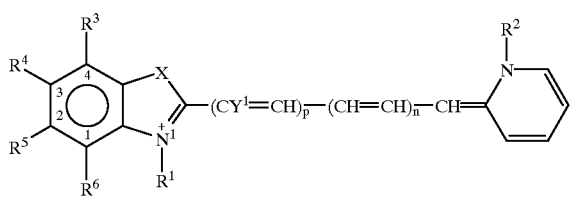
(XV)

the compound of formula (XV) existing alone or in combination with a counterion thereof, wherein n, p, $R^1$–$R^6$, and X are defined above.

Yet another preferred class of compounds of formula (I) has the structure of formula (XVI):

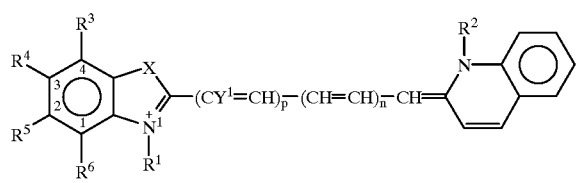
(XVI)

the compound of formula (XVI) existing alone or in combination with a counterion thereof, wherein n, p, $R^1$–$R^6$, X and $Y^1$ are defined above.

Another preferred class of compounds of formula (I) has the structure of formula (XVII):

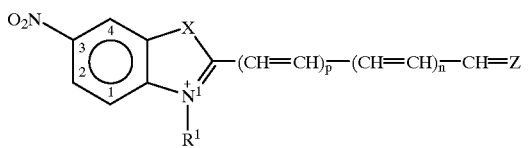
(XVII)

the compound of formula (XVII) existing alone or in combination with a counterion thereof, wherein n, p, $R^1$, Z, and X are defined above.

Yet another preferred class of compounds of formula (I) has the structure of formula (XVIII):

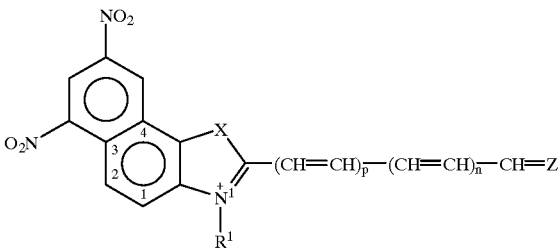
(XVIII)

the compound of formula (VII) existing alone or in combination with a counterion thereof, wherein n, p, $R^1$, Z, and X are defined above.

Still another preferred class of compounds of formula (I) has the structure of formula (XIX):

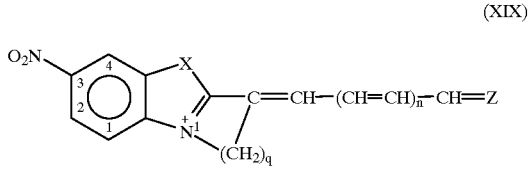
(XIX)

the compound of formula (XIX) existing alone or in combination with a counterion thereof, wherein n, q, Z, and X are defined above.

Another preferred class of compounds of formula (I) has the structure of formula (XX):

(XX)

the compound of formula (IX) existing alone or in combination with a counterion thereof, wherein n, q, Z, and X are defined above.

In a preferred embodiment of the present invention, the compound of formula (I) comprises a linking group that is amine or lower alkylcarboxy.

In another preferred embodiment of the present invention, the compound of formula (I) comprises one of $R^1$ or $R^2$ that is —$(CH_2)_m N^+(CH_3)_3$, and the other of $R^1$ and $R^2$ that is a linking group.

In still another preferred embodiment of the present invention, the compound of formula (I) comprises the linking group —$(CH_2)_m N^+(CH_3)_2(CH_2)_m CO_2 H$.

In another preferred embodiment of the present invention, the compound of formula (I) comprises X that is sulfur.

In another preferred embodiment of the present invention, the compound of formula (I) comprises q that is 2.

Preferably, the compounds of formula (I) are selected from the group consisting of:

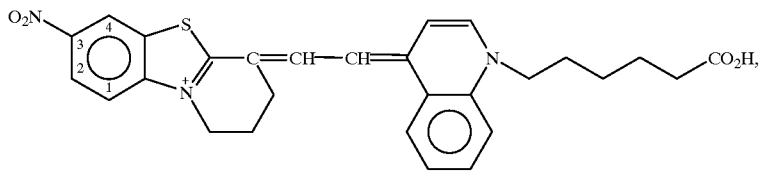

(XXI)

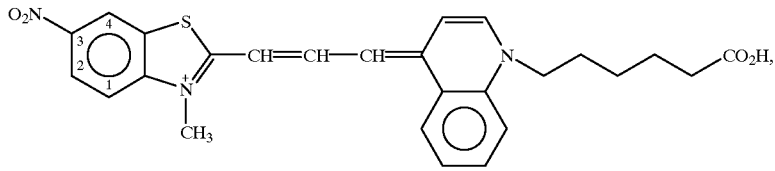

(XXII)

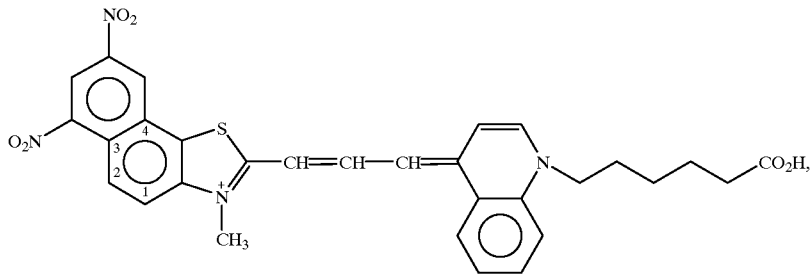

(XXIII)

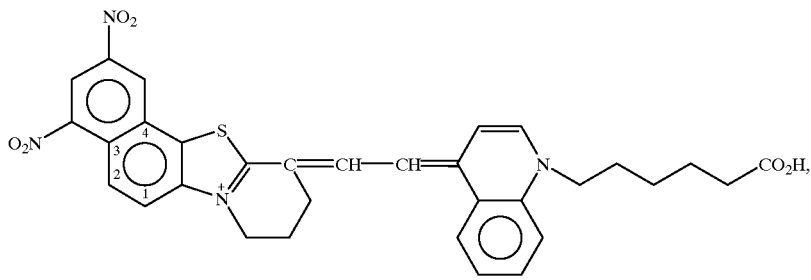

(XXIV)

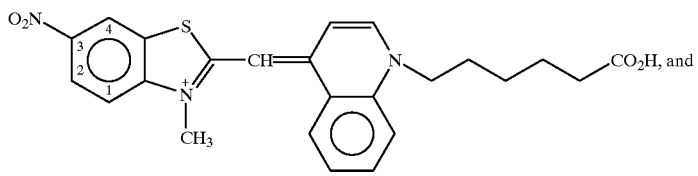

(XXV)

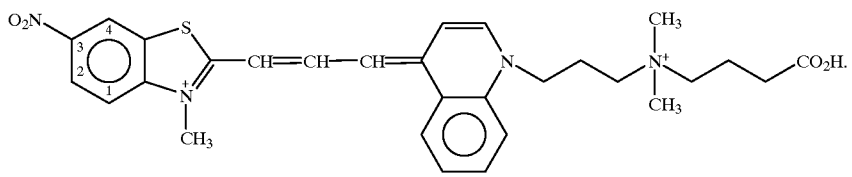

(XXVI)

Linking Groups

In another aspect, the present invention comprises one or more reagents linked to the asymmetric cyanine dyes of the invention. The dyes are conjugated with the reagent via the linking group by a variety of means, including hydrophobic attraction, ionic attraction, covalent attachment or with the aid of pairs of specific binding molecules, as previously described. Preferably, the dyes are linked via covalent attachment.

The compounds of formula (I) can be linked to a variety of molecules and substances without altering the quenching and spectral properties of the dyes, or in most instances, the biological activity of the reagent. The linking group can be used to link, preferably by way of covalent attachment, the asymmetric cyanine dye to a reagent. As depicted in structural formula (I), the linking group is attached either to $N^1$ or to the heteroaromatic nitrogen in group Z.

Generally, the linking group has the structure —L—$R_x$, where $R_x$ is a reactive functional group attached to the compound of formula (I) via covalent linkage L. Depending upon the particular application, reactive group $R_x$ may be attached directly to $N^1$ or to the heteroaromatic ring nitrogen of Z, or it may be spaced away through one or more intervening atoms that serve as a spacer. In the former embodiment, L represents a bond. In the latter embodiment, L represents a spacer. The spacer can be hydrophilic or hydrophobic, long or short, rigid, semirigid or flexible, depending upon the particular application. The spacer can be optionally substituted with one or more additional reactive functional groups, which may be the same or different than reactive functional group $R_x$, thereby providing a "polyvalent" linking group capable of conjugating with multiple molecules or substances. Preferably, however, spacer L does not include such additional reactive groups.

A wide variety of spacers L having stable bonds suitable for spacing reactive groups such as $R_x$ from molecules are known in the art, and include by way of example and not limitation, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. Thus, spacer L may include single, double, triple or aromatic carbon-carbon bonds, nitrogen-nitrogen bonds, carbon-oxygen bonds and/or carbon-sulfur bonds, and may therefore include functionalities such as carbonyls, ethers, esters, thioether, thioesters, carboxamides, sulfonamides, ureas, urethanes, carbonates, hydrazines, etc. In one embodiment, spacer L has 1–20 non-hydrogen atoms selected from the group consisting of C, N, O, Se and S and is composed of any combination of ether, thioether, amine, ester, carboxamide, sulfaramide, hydrazide, aromatic and heteroaromatic bonds. Choosing a spacer having properties suitable for a particular application is within the capabilities of those having skill in the art.

For example, where a rigid spacer is desired, the spacer may be a rigid polypeptide such as polyproline, a rigid polyunsaturated alkyldiyl or an aryldiyl, biaryldiyl, arylaryldiyl, heteroaryldiyl, biheteroaryldiyl, heteroaryl-heteroaryldiyl, etc. Where a flexible spacer is desired the spacer may be a flexible polypeptide such as polyglycine or a flexible saturated alkanyldiyl or heteroalkanyldiyl. Hydrophilic spacers may be, for example, polyalcohols or polyethers such as polyalkyleneglycols. Hydrophobic spacers may be, for example, alkyldiyls or aryldiyls. Preferred spacers, suitable for use in most biological applications include ($C_1$–$C_6$) alkyldiyls, particularly alkanyldiyls such as propano (—$CH_2$—$CH_2$—$CH_2$—), butano (—$CH_2$—$CH_2$—$CH_2$—$CH_2$—), pentano (—$CH_2$—$CH_2$—$CH_2$—$CH_2$—$CH_2$—) and hexano (—$CH_2$—$CH_2$—$CH_2$—$CH_2$—$CH_2$—$CH_2$—); ($C_5$–$C_{20}$) aryldiyls, particularly phen-1,3-diyl, phen-1,4-diyl, naphtha-2,6-diyl and naphtha-2,7-diyl; and ($C_6$–$C_{26}$) arylalkyldiyls, particularly those having the structural formula —($CH_2$)$_i$-ϕ- or —($CH_2$)$_i$-ψ-, where each i is independently an integer from 1 to 6, ϕ is phenyldiyl (especially phen-1,3-diyl or phen-1,4-diyl) and ψ is naphthyldiyl (especially naphtha-2,6-diyl or naphtha-2,7-diyl). Analogs of these preferred spacers L containing one or more heteroatoms, particularly those selected from the group consisting of O, S, N and NR", where R" is hydrogen or ($C_1$–$C_6$) alkyl, can also be conveniently used to space reactive group $R_x$ from the compounds of formula (I). Other preferred spacers include: alkyldiyls, substituted allyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. Spacers tailored to specific applications are discussed in more detail, infra.

The compounds of formula (I) can be conveniently covalently conjugated to a wide variety of organic or inorganic molecules or substances by reacting the dye with molecules or substances that contain, or are modified to contain, one or more functional groups $F_x$ that are complementary to reactive group $R_x$. By "complementary" is meant that functional group $F_x$ reacts with reactive group $R_x$ to form a covalent linkage. The reaction of reactive group $R_x$ with complementary functional group $F_x$ results in the covalent attachment of the dye to a reagent.

Complementary groups capable of forming covalent linkages with one another are well-known. Typically, reactive group $R_x$ is an electrophile and functional group $F_x$ is a nucleophile, or reactive group $R_x$ is a nucleophile and functional group $F_x$ is an electrophile. Accordingly, reactive group $R_x$ and functional group $F_x$ are complementary electrophiles and nucleophiles capable of forming a covalent linkages with one another. Alternatively, reactive group $R_x$ can be a photoactivatable group that becomes chemically reactive only after illumination with light of an appropriate wavelength. Such photoactivatable groups can be conveniently used to cross-link the dye to the reagent.

A plethora of complementary electrophile/nucleophile pairs and photoactivatable groups suitable for covalently conjugating two molecules together are well-known. The actual choice of complementary pairs or photoactivatable group will depend upon a variety of factors, and will be apparent to those of skill in the art. Examples of complementary electrophiles and nucleophiles suitable for use in a wide variety of contexts are shown in Table 1, where the reaction of the indicated electrophilic and nucleophilic group yields the indicated resulting linkage. Conditions under which the covalent linkages are formed are well-known.

TABLE 1

Examples of Some Routes to Useful Covalent Linkages

| Electrophilic Group | Nucleophilic Group | Resulting Linkage |
|---|---|---|
| activated esters* | amines/anilines | carboxamides |
| acyl azides** | amines/anilines | carboxamides |
| acyl halides (especially halo acetyl) | amines/anilines | carboxamides |
| acyl halides (especially halo acetyl) | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | esters |
| anhydrides | alcohols/phenols | esters |
| anhydrides | amines/anilines | carboxamides |
| aryl halides | thiols | thiophenols |

TABLE 1-continued

Examples of Some Routes to Useful Covalent Linkages

| Electrophilic Group | Nucleophilic Group | Resulting Linkage |
|---|---|---|
| aryl halides | amines | aryl amines |
| arizidines | thiols | thioethers |
| boronates | glycols | boronate esters |
| carboxylic acids*** | amines/anilines | carboxamides |
| carboxylic acids*** | alcohols | esters |
| carboxylic acids*** | hydrazines | hydrazides |
| carbodimides | carboxylic acids | N-acylureas or anhydrides |
| diazoalkanes | carboxylic acids | esters |
| epoxides | thiols | thioethers |
| haloacetamides (especially iodo-acetamide) | thiols | thioethers |
| halotriazines (especially 4,6-dichloro-triazines) | amines/anilines | aminotriazines |
| halotriazines (especially 4,6-dichloro-triazines) | alcohols/phenols | amidines |
| imido esters | amines/anilines | amidines |
| isocyanates | amines/anilines | ureas |
| isocyanates | alcohols/phenols | urethanes |
| isothiocyanates | aminieslanilines | thioureas |
| maleimides | thiols | thioethers |
| phosphoramidites | alcohols | phosphite esters |
| silyl halides | alcohols | silyl ethers |
| succinimidyl esters | amines | amides |
| succinimidyl esters | alcohols | esters |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides (especially sulfonyl chlorides) | amines/anilines | sulfonamides |
| sulfonyl halides (especially sulfonyl chlorides) | phenols/alcohols | sulfonate esters |

*Activated esters, as understood in the art, generally have the formula —COG, where G is a good leaving group, e.g., oxysuccinimidyl (—OC$_4$H$_4$O$_2$), oxysulfosuccinimidyl (—OC$_4$H$_3$O$_2$—SO$_3$H), 1-oxybenzotriazoiyl (—OC$_6$H$_4$N$_3$); or an aryloxy group of the formula —ORH" where R" is an aryl or an aryl substituted with one or more of the same or different electron- withdrawing substitutes (e.g., —NO$_2$, —F, —Cl, —CN or —CF$_3$), used to form an anhydride or mixed anhydride of the formula —OCOR$^a$ or OCNR$^a$NHR$^b$, where R$^a$ and R$^b$ which may be the same or different, are (C$_1$–C$_6$) alkyl, (C$_1$–C$_6$) perfluoroalkyl or (C$_1$–C$_6$) alkoxy or cyclohexyl, 3-dimethylaminopropyl, or N-morpholinoethyl.
**Acyl azides can also rearrange to isocyanates.
***especially preferred carboxylic acids are —(CH$_2$)$_m$N$^+$(CH$_3$)$_2$(CH$_2$)$_m$CO$_2$H where each m is independently an integer from 2 to 12.

Exemplary photoactivatable groups suitable for conjugation via light-activated cross-linking include, but are not limited to, azido (—N$_3$), 4-azido-phenyl and 2-nitro-4-azido-phenyl. Conjugation using photoactivatable groups typically involves illuminating a mixture comprising the photoactivatable dyes and the molecule or substance to be conjugated to activate the dyes, followed by separation of unreacted dyes and byproducts.

The selection of reactive group R$_x$ used to covalently link the compounds of formula (I) to the reagent typically depends upon the identity of the complementary functional group F$_x$ on the molecule or substance to be conjugated. The types of complementary functional groups typically present on molecules or substances to be conjugated include, but are not limited to, amines, thiols, alcohols, phenols, aldehydes, ketones, phosphates, imidazoles, hydrazines, hydroxylamines, mono- and disubstituted amines, halides, epoxides, sulfonate esters, carboxylic acids or carboxylates, or a combination of these groups. A single type of complementary functional group may be available on the molecule or substance (typical for polysaccharide), or a variety of different complementary functional groups may be available (e.g. amines, thiols, alcohols, phenols), as is typical for proteins. The reagent may be linked to more than one asymmetric dye, which may be the same or different. Although some selectivity can be obtained by carefully controlling the reaction conditions, selectivity of conjugation is best obtained by appropriate choice of reactive group R$_x$.

In a preferred embodiment, reactive group R$_x$ reacts with an amine, a thiol or an alcohol. In one embodiment, reactive group R$_x$ is an acrylamide, an activated ester of a carboxylic acid or carboxylate, an acyl azide, an acyl nitrile, an acyl halide, an aldehyde, an alkyl halide, an amine, an anhydride, an aniline, an aryl halide, an azide, an aziridine, a boronate, a carboxylic acid or carboxylate, a diazoalkane, a haloacetamide, a halotriazine, a hydrazine, an imido ester, an isocyanate, an isothiocyanate, a maleimide, a phosphoramidite, a sulfonyl halide, or a thiol group.

In a particularly preferred embodiment, reactive group R$_x$ is a carboxylic acid or carboxylate, an activated ester of a carboxylic acid or carboxylate, a succinimide ester, an amine, a haloacetamide, an acyl halide, an alkyl halide, a sulfonyl halide, an isothiocyanate, a maleimide or an azidoperfluorobenzamido group. In an even more preferred embodiment, reactive group R$_x$ is an N-hydroxysuccinimidyl (NHS) ester and complementary functional group R$_x$ is an amine, where to form the NHS ester, an asynmmetric dye of the invention including a carboxylic acid or carboxylate reactive group is activated with dicyclohexylcarbodiimide and N-hydroxysuccinimide according to known methods.

For a thorough discussion of the various reactive groups R$_x$ and respective complementary functional groups F$_x$ that can be conveniently used to covalently conjugate the compounds of formula (I) to a variety of reagents, see R. Haugland, 1996, *Molecular Probes Handbook of Fluorescent Probes and Research Chemicals,* Molecular Probes, Inc. and the references cited therein, and Brindley, 1992, Bioconjugate Chem. 3:2.

Alternatively, the conjugation of the compounds of formula (I) to reagents may be mediated by non-covalent interactions, such as hydrophobic interactions, ionic interactions, or through the use of pairs of specific binding compounds, such as biotin and avidin/streptavidin. When conjugation via hydrophobic interactions is desired, both reactive group R$_x$ and complementary functional group F$_x$ are hydrophobic moieties such as aryl, arylaryl, heteroaryl or heteroaryl-heteroaryl groups.

When conjugation via ionic interactions is desired, groups R$_x$ and F$_x$ are oppositely charged such that they attract one another. Typical charged groups include, by way of example and not limitation, quaternary ammoniums, carboxylates, sulfates, sulfonates, and phosphates. A variety of cyclic quaternary ammoniums that are suitable for use as R$_x$ are described in U.S. Pat. No. 5,863,753, (see, e.g., Cols. 8–9), the disclosure of which is incorporated herein by reference.

When conjugation via pairs of specific binding compounds such as biotin and streptavidin is desired, one of R$_x$ or F$_x$ will constitute one member of the binding pair and the other will constitute the other member of the binding pair. Where one of the members of the specific binding pair is a small molecule, such as biotin or a hormone, that member preferably comprises R$_x$. A variety of biotins capable of being covalently linked to reactive functional groups such as amines are commercially available (e.g., from Molecular Probes, Eugene, Oreg.). These biotins can be reacted with linking moieties containing amine reactive groups to generate biotin-linking moieties.

Other representative specific binding pairs that can be used to conjugate the dyes to reagents are provided in Table 2.

TABLE 2

Representative Specific Binding Pairs

| | |
|---|---|
| biotin | avidin (or streptavidin or anti-biotin) |
| IgG | protein A or protein G |
| drug | drug receptor |
| toxin | toxin receptor |
| carbohydrate | lectin or carbohydrate receptor |
| peptide | peptide receptor |
| protein | protein receptor |
| enzyme inhibitor | enzyme |
| hormone | hormone receptor |
| ion | chelator |

Synthesis

The compounds of formula (I) can be obtained using conventional methods. See, for example, U.S. Pat. No. 5,658,751 to Yue et al.; U.S. Pat. No. 5,436,134 to Haugland et al.; G. E. Ficken, *Cyanine Dyes, in Chemistry of Cyanine Dyes* 211–341 (Venkataraman ed., 1971); D. M. Sturmer, *Synthesis and Properties of Cyanine and Related Dyes, in The Chemistry of Heterocyclic Compounds* 441–601 (A. Weissberger and E. C. Taylor eds., 1977); and references cited therein.

For example, the compounds of formula (IV), in the case where p and n are not both 0, can be obtained by nitrating, with nitric acid, 2-methylbenzothiazole, 2-methylbenzoselenazole, or 2-methylbenzoxazole, where X of the compound of formula (IV) is S, Se, or O, respectively. N-Alkylation of the resulting product with $R^1$—LG provides an azolium species, where LG is a leaving group. It will be understood that N-alkylation with $R^1$—LG provides $LG^-$, which is a counterion that can associate with the compounds of formula (I). In the case where p is 0 and n is 1, or where p is 1 and n is 0, the azolium species is reacted with PhNHCH=NPh in the presence of acetic anhydride to afford an acetanilidovinylazolium species. The acetanilidovinylazolium species is then reacted, in the presence of base, with the N—$R^2$ salt product of $R^2$—LG and 4-methylpyridine, 4-methylquinoline, 2-methylpyridine, or 2-methylquinoline to provide the desired compounds.

In the case of the compounds of formula (IV) where both p and n are 1, the azolium species obtained above is reacted with PhNHCH=CH—CH=NPh according to the methods of U.S. Pat. No. 2,269,234 to Sprague to obtain a 2-(4-anilino)-1,3-butadienyl)azolium species. The 2-(4-anilino)-1,3-butadienyl)azolium species is then reacted, in the presence of base, with the N—$R^2$ salt product of $R^2$—LG and 4-methylpyridine, 4-methylquinoline, 2-methylpyridine, or 2-methylquinoline to provide the desired compounds.

In the case of the compounds of formula (IV) where both p and n are 0, 2-(methylthio)benzothiazole, 2-(methylthio) benzoselenazole, or 2-(methylthio)benzoxazole, where X of the compound of formula (IV) is S, Se, or O, respectively, are nitrated with nitric acid and then N-alkylated with $R^1$—LG as described above. The resulting azolium species is then reacted, in the presence of base, with the N—$R^2$ salt product of $R^2$—LG and 4-methylpyridine, 4-methylquinoline, 2-methylpyridine, or 2-methylquinoline to provide the desired compounds.

The compounds of formula (VII) and those compounds of formula (I) where $R^4$ and $R^5$ taken together form a benzo group and $R^3$ and $R^6$ are hydrogen, or where $R^5$ and $R^6$ taken together form a benzo group and $R^3$ and $R^4$ are hydrogen, can be obtained according to the methods used to obtain the compounds of formula (IV), except that the appropriate naphthothiazole, napthoselenazole, or naphthoxazole is substituted for the appropriate benzothiazole, benzoselenazole, or benzoxazole, respectively.

The compounds of formula (VIII) can be obtained by treating the nitrated 2-methylbenzothiazole, 2-methylbenzoselenazole, or 2-methylbenzoxazole, described above, with LG—$(CH_2)$p-LG to obtain an N—$(CH_2)$p-LG azolium species. —$(CH_2)$p- can be unsubstituted or substituted as described above. The 2-methyl group of the N—$(CH_2)$p-LG azolium species is then deprotonated in the presence of base, and the resulting anion displaces the —LG of the N—$(CH_2)$p-LG to form a fused ring of 3+q members. The carbon atom of the former 2-methyl group is further deprotonated with base and treated with either PhNHCH=NPh and acetic anhydride (where n=0 for the compounds of formula (VIII)) or PhNHCH=CH—CH=NHPh (where n=1 for the compounds of formula (VIII)). The resulting product is reacted, in the presence of base, with the N—$R^2$ salt product of $R^2$—LG and 4-methylpyridine, 4-methylquinoline, 2-methylpyridine, or 2-methylquinoline to provide the desired compounds.

The compounds of formula (IX) and those compounds of formula (I) where $R^4$ and $R^5$ taken together form a benzo group and $R^3$ and $R^6$ are hydrogen, or $R^5$ and $R^6$ taken together form a benzo group and $R^3$ and $R^4$ are hydrogen, can be obtained according to the methods used to obtain the compounds of formula (VIII), except that the appropriate naphthothiazole, napthoselenazole, or naphthoxazole is substituted for the appropriate benzothiazole, benzoselenazole, or benzoxazole, respectively.

Nucleoside/Tide Reagents

Structure

One embodiment of the present invention includes a class of labeled reagents comprising nucleosides/tides and nucleoside/tide analogs that incorporate a compound of formula (I). Such labeled reagents are particularly useful for labeling polynucleotides formed by enzymatic synthesis, e.g., labeled nucleotide triphosphates used in the context of PCR amplification, Sanger-type polynucleotide sequencing, and nick-translation reactions.

To the extent that the labeled reagents of the invention are used in oligonucleotide synthesis that entails the use of reactive nucleoside/tide species, the present invention contemplates the use of one or more protecting groups for any chromophore or spacer having a functional group that, if unprotected, could potentially react with a nucleoside/tide that has a reactive functional group. Thus, a "protected derivative" of any of the compounds of the invention is a compound comprising one or more protecting groups. Suitable protecting groups are known to those skilled in the art and are found in, e.g., Greene, 1981, *Protective Groups in Organic Synthesis*, John Wiley & Sons, Inc., New York. Exemplary protecting groups for hydroxyl groups can be found on pages 10–86 of the above; exemplary protecting groups for phenols and catechols can be found on pages 87–113 of the above; exemplary protecting groups for carbonyl groups can be found on pages 114–151 of the above; exemplary protecting groups for carboxyl groups can be found on pages 152–192 of the above; exemplary protecting groups for thiol groups can be found on pages 193–217 of the above; and exemplary protecting groups for amino groups can be found on pages 218–287 of the above.

Generally, the labeled nucleoside/tide reagents are compounds according to structural formula (II):

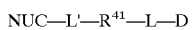

(II)

wherein:
NUC is a nucleoside/tide or nucleoside/tide analog;
L' is a bond or a first spacer;
$R^{41}$ is a covalent linkage;
L is a bond or a second spacer as previously described; and
D is the chromophore of formula (I),
and protected derivatives thereof As depicted in structural formula (II), dye chromophore D is covalently attached to the nucleoside/tide or nucleoside/tide analog through linkage —L'—$R^{41}$—L—. L may be attached to the heteroaromatic imminium nitrogen as depicted in structural formula (I), in which case $R^1$ of formula I is NUC—L'$R^{41}$—L—; alternatively, —L'—$R^{41}$—L—. L may be attached to the heteroaromatic nitrogen in group Z as depicted in structural formula (I), in which case $R^2$ is NUC—L'$R^{41}$—L—.

In one embodiment, D comprises one or more protecting groups.

Thus a preferred embodiment of the invention contemplates a compound of formula (III)

(III)

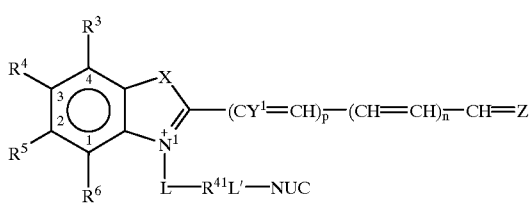

alone or in combination with a counterion thereof, wherein:
p is 0 or 1;
n is 0 or 1;
X is S, Se or O;
$N^1$ is nitrogen;
$Y^1$ is H;
$N^1$ is nitrogen;
L and L' are independently a bond or a spacer;
$R^{41}$ is a linkage selected from the group consisting of covalent linkages, ionic linkages, and specific binding pair linkages; and
Z is selected from the group consisting of:

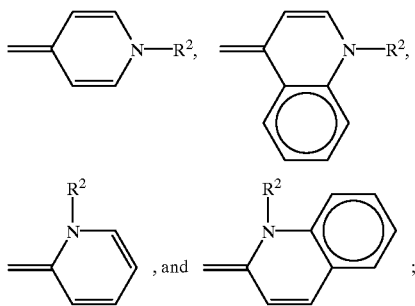

NUC is a nucleotide, a nucleotide analog, a nucleoside, or a nucleoside analog;
$R^2$ is selected from the group consisting of alkyl, aryl, —$CH_2$aryl, and —$(CH_2)_m N^+(CH_3)_3$, optionally substituted with one or more of the same or different —$NO_2$, —OH, alkoxy, —COOH, —$COOC_1$-$C_4$ alkyl, —NHCHO, —$NHCOC_1$-$C_4$ alkyl, —$NHCOCH_3$, —$NHCOCH_2Cl$, —$NHCOCHCl_2$, —$NHCOCCl_3$, —$NHCOCF_3$, —$NHCOCH_2C_6H_4$-o-$NO_2$, —$NHCOCH_2OC_6H_4$-o-$NO_2$, —$NHCOCH_2COCH_3$, —$NHCOCH_2$—$N^+C_5H_5Cl^-$, —$NHCOCH_2NHCS_2CH_2C_6H_5$, —$NHCOCH_2CH_2C_6H_5$, —$NHCOCH_2CH_2C_6H_4$-p-OH, —$NHCOCH_2CH_2C_6H_4$-o-$NO_2$, —$NHCOC(CH_3)_2OC_6H_4$-o-$NO_2$, —$NHCOC(CH_3)_2OC_6H_4$-o-N=$NC_6H_5$, —$NHCO(CH_2)_3Cl$, —$NHCOCH(CH_3)_2$, —$NHCOCH$=$CHC_6H_4$-o-$NO_2$, or —NHCO-2-pyridyl groups; either:

(a) $R^3$, $R^5$ and $R^6$ are H and $R^4$ is —$NO_2$; or
(b) $R^3$ and $R^4$ taken together form a benzo group substituted with one or two —$NO_2$ groups and $R^5$ and $R^6$ are hydrogen; or
(c) $R^4$ and $R^5$ taken together form a benzo group substituted with one or two —$NO_2$ groups and $R^3$ and $R^6$ are hydrogen; or
(d) $R^5$ and $R^6$ taken together form a benzo group substituted with one or two —$NO_2$ groups and $R^3$ and $R^4$ are hydrogen;

with the proviso that when L—$R^{41}$ or formula (III) has an $sp^3$ hybridized carbon atom that is covalently attached to $N^1$, then that carbon atom is methyl or, when substituted, primary, and protected derivatives thereof.

A preferred class of compounds are the compounds of the formula (XXVII):

(XXVII)

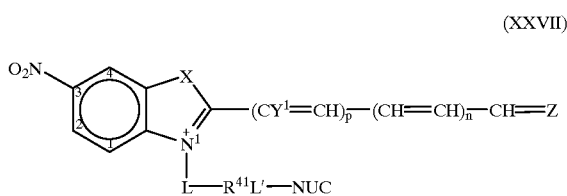

alone or in combination with a counterion thereof.

Another preferred class of compounds are the compounds of the formula (XXVIII):

(XXVIII)

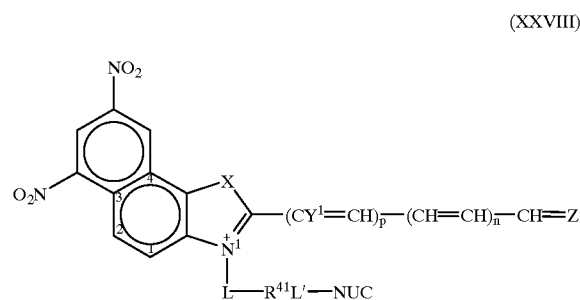

alone or in combination with a counterion thereof.

Another preferred embodiment includes a compound of formula (IV):

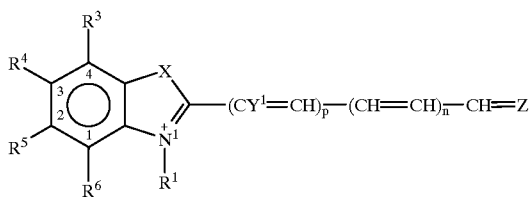

(IV)

alone or in combination with a counterion thereof, wherein:

p is 0 or 1;

n is 0 or 1;

$N^1$ is nitrogen;

X is S, Se or O;

L and L" are independently a bond or a spacer,

Z is selected from the group consisting of:

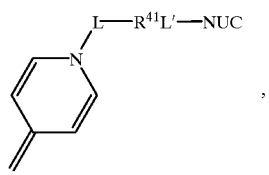

,

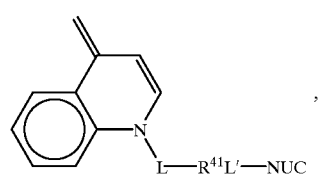

,

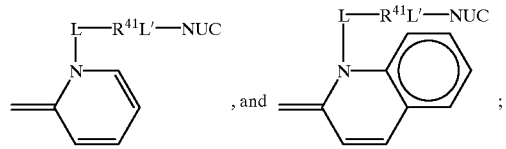

, and ;

NUC is a nucleoside, a nucleotide analog, a nuclueoside, or a nucleoside analog;

$R^{41}$ is a linkage selected from the group consisting of covalent linkages, ionic linkages, and specific binding pair linkages.

$R^1$ is A, and $Y^1$ is H, or p is 1 and $R^1$ and $Y^1$ taken together are $(CH_2)_q$;

A is selected from the group consisting of alkyl, aryl, —$CH_2$aryl, and —$(CH_2)_m N^+(CH_3)_3$;

q is an integer ranging from 2 to 4;

each m is independently an integer ranging from 2 to 12;

A or $(CH_2)_q$ are unsubstituted or independently substituted with one or more of the same or different —$NO_2$, —OH, alkoxy, —COOH, —$COOC_1$-$C_4$ alkyl, —NHCHO, —$NHCOC_1$-$C_4$ alkyl, —$NHCOCH_3$, —$NHCOCH_2Cl$, —$NHCOCHCl_2$, —$NHCOCCl_3$, —$NHCOCF_3$, —$NHCOCH_2C_6H_4$-o-$NO_2$, —$NHCOCH_2OC_6H_4$-o-$NO_2$, —$NHCOCH_2COCH_3$, —$NHCOCH_2$—$N^+C_5H_5Cl^-$, —$NHCOCH_2NHCS_2CH_2C_6H_5$, —$NHCOCH_2CH_2C_6H_5$, —$NHCOCH_2CH_2C_6H_4$-p-OH, —$NHCOCH_2CH_2C_6H_4$-o-$NO_2$, —NHCOC$(CH_3)_2OC_6H_4$-o-$NO_2$, —$NHCOC(CH_3)_2OC_6H_4$-o-N=$NC_6H_5$, —$NHCO(CH_2)_3Cl$, —$NHCOCH(CH_3)_2$, —NHCOCH=$CHC_6H_4$-o-$NO_2$, or —NHCO-2-pyridyl groups; either:

(a) $R^3$, $R^5$ and $R^6$ are H and $R^4$ is —$NO_2$; or (b) $R^3$ and $R^4$ taken together form a benzo group substituted with one or two —$NO_2$ groups and $R^5$ and $R^6$ are hydrogen; or (c) $R^4$ and $R^5$ taken together form a benzo group substituted with one or two —$NO_2$ groups and $R^3$ and $R^6$ are hydrogen; or (d) $R^5$ and $R^6$ taken together form a benzo group substituted with one or two —$NO_2$ groups and $R^3$ and $R^4$ are hydrogen;

with the proviso that when $R^1$ in the compounds of formula (I) has an $sp^3$ hybridized carbon atom that is covalently attached to $N^1$, then that carbon atom is methyl or, when substituted, primary, and protected derivatives thereof.

A preferred class of compounds of formula (IV) have the structure formula (XXIX):

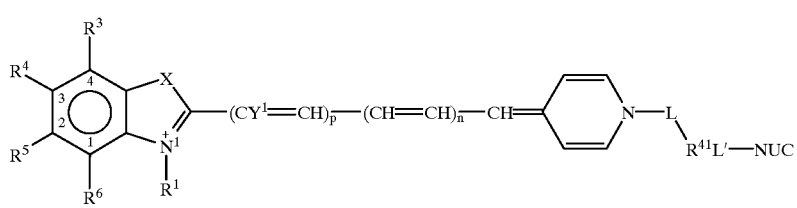

(XXIX)

alone or in combination with a counterion thereof.

A second preferred class of compounds of formula (IV) have the structure of formula (XXX):

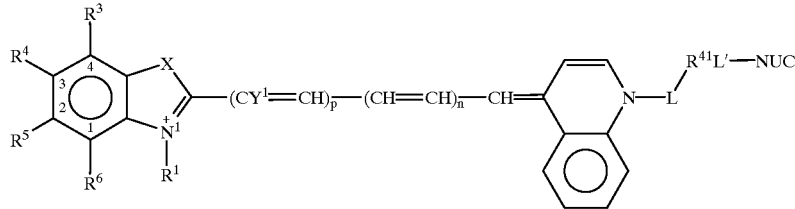

alone or in combination with a counterion thereof.

A third preferred class of compounds of formula (IV) have the structure of formula (XXXI):

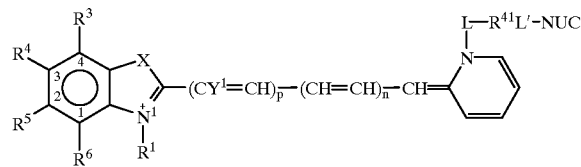

alone or in combination with a counterion thereof.

A fourth preferred class of the compounds of formula (VI) have the structure of formula (XXXII):

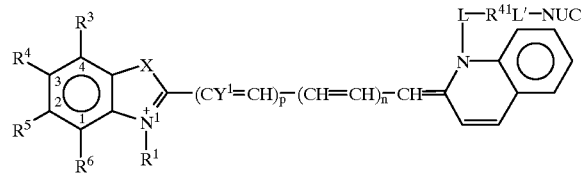

alone or in combination with a counterion thereof.

In preferred embodiments, $R^{41}$ in formulas (III) and (IV) is a linkage selected from the group consisting of:

a covalent linkage selected carboxamides, esters, imines, hydrazones, oximes, alkylamines, thioethers, ethers, thiophenols, aryl amines, boronate esters, hydrazides, N-acylureas or anhydrides, aminotriazines, triazinyl ethers, amidines, ureas, urethanes, thioureas, phosphite esters, silyl ethers, alkyl amines, sulfonamides, and sulfonate esters;

a linkage between a pair of specific binding compounds selected from the group consisting of biotin with avidin, biotin with streptavidin, biotin with anti-biotin, IgG with protein A, IgG with protein G, a drug with a drug receptor, a toxin with a toxin receptor, a carbohydrate with a lectin, a carbohydrate with a carbohydrate receptor, and a peptide with a peptide receptor; and a linkage between an anionic group and a cationic group; and L and L' are independently selected from the group consisting of a carbon-carbon bond, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, azylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, and substituted heteroaryl-heteroalkyldiyls.

In more preferred embodiments, $R^{41}$ in formulas (III) and (IV) is a linkage selected from the group consisting of amides, esters, thioesters, alkyl amines, aryl amines, sulfonamides, ureas, and thioureas, and L and L' are independently bonds or alkyldyls.

In most preferred embodiments, $R^{41}$ in formulas (III) and (IV) is a linkage selected from the group consisting of amides, esters, and thioesters.

D can be covalently linked to the sugar moiety, or, preferably, to the nucleobase moiety of NUC. When NUC includes a purine nucleobase moiety, —L'—$R^{41}$—L—D preferably forms a covalent linkage with the $C^7$ position of the nucleobase; when NUC includes a 7-deazapurine nucleobase moiety, —L'—$R^{41}$—D preferably forms a covalent linkage with the $C^7$-position of the nucleobase; and when NUC includes a pyrimidine nucleobase, —L'—$R^{41}$—L—D preferably forms a covalent linkage with the $C^5$-position of the nucleobase. Nucleobase analogs can also be labeled at these same positions, or other corresponding positions (depending upon the particular analog), as will be apparent to those of skill in the art.

Labeled polynucleotides or polynucleotide analogs synthesized with labeled nucleoside/tide reagents according to structural formula (II) are particularly useful as fluorescence quenching probes in assays involving nucleic acid hybridization. Thus, the linkage —L'—$R^{41}$—L— should: (i) be stable to oligonucleotide synthesis conditions; (ii) not interfere with probe-target hybridization; and (iii) be compatible with relevant enzymes, e.g., polymerases, ligases, and the like.

Preferred spacers L' for covalently conjugating the dyes of the invention to nucleoside/tide or nucleoside/tide analogs include ($C_1$–$C_{20}$) alkylenos and 2–20 membered heteroalkylenos, especially ($C_1$–$C_{20}$) alkynos, ($C_1$–$C_{20}$) alkenos, 2–20 membered heteroalkylenos and 2–20 membered heteroalkenos. A particularly preferred spacer L' is —C≡C—$CH_2$— where the terminal alkynyl (sp) carbon is covalently attached to NUC and the terminal methylene ($sp^3$) carbon is covalently attached to $R_x$ in the compounds of structural formula (II), or to $F_x$ in compound 10 of Scheme (III). Labeled nucleoside/tide or nucleoside/tide analogs including this preferred spacer L' are compounds according to structural formula (XXXIII):

wherein NUC, $R^{41}$, L and D are as previously defined for structural formula (II).

Additional preferred spacers L' for covalently conjugating the asymmetric dyes of the invention to nucleosides/tides and/or nucleoside/tide analogs include propargylethoxy groups according to structural formula —C≡C—CH$_2$—O—CH$_2$—CH$_2$NR$^{57}$—R$^{58}$—, wherein $R^{57}$ is hydrogen or ($C_1$–$C_6$) alkyl; $R^{58}$ is selected from the group consisting of —C(O)—(CH$_2$)$_r$—, —C(O)—CHR$^{59}$—, —C(O)—C≡C—CH$_2$— and —C(O)-φ-(CH$_2$)$_r$—, where each r is independently an integer from 1 to 5 and φ represents a $C_6$ aryldiyl or a 6-membered heteroaryldiyl, preferably phen-1,4-diyl

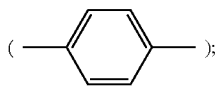

and $R^{59}$ is hydrogen, ($C_1$–$C_6$) alkyl or an amino acid side chain (including both gene-encoded and non-encoded amino acids). With these spacers, the terminal alkynyl carbon is attached to NUC and the other terminal group ($R^{58}$) is attached to $R^{41}$ in the compounds of structural formula (II) or $R_x$ in compounds 11 of Scheme (III). Labeled nucleoside/tide or nucleoside/tide analogs including these preferred spacers L' are compounds according to structural formula (V):

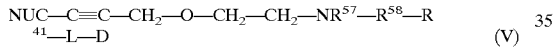

wherein:
NUC, L and D are as previously defined for structural formula (IV);
$R_{57}$ is hydrogen or ($C_1$–$C_6$) alkyl;
$R^{58}$ is —C(O)—(CH$_2$)$_r$—, —C(O)—CHR$^{59}$—, —C(O)—C≡C—CH$_2$— or —C(O)-φ-(CH$_2$)$_r$—;
each r is independently an integer from 1 to 5;
φ is a $C_6$ aryldiyl or a 6-membered heteroaryldiyl, preferably phen-1,4-diyl

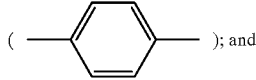

and
$R^{59}$ is hydrogen, ($C_1$–$C_6$) alkyl or an amino acid side chain (including both gene-encoded and non-encoded amino acids).

Preferred labeled nucleosides/tides and/or nucleoside/tide analogs according to structural formulae (II), (V) and (VI) are those in which $R^{41}$ is an amide or substituted amide of the formula —NR$^{56}$—C(O)—, where $R^{56}$ is ($C_1$–$C_6$) alkyl or preferably hydrogen; L is a ($C_1$–$C_6$) alkyleno, a ($C_1$–$C_6$) alkano, or pentano; and/or D is an asymmetric dye chromophore derived from structural formula (I).

Particularly preferred labeled nucleosides/tides and nucleoside/tide analogs of the present invention are compounds according to structural formula (VI):

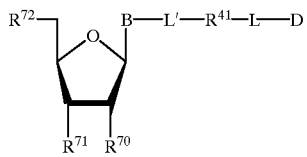

wherein:
B is a nucleobase or nucleobase analog;
L' is a bond or a first spacer as previously described;
$R^{41}$ represents a covlent linkage as previously described;
L is a bond or a second spacer as previously described;
D is an asymmetric cyanine dye chromophore as previously described;
$R^{70}$ and $R^{71}$ are each independently —H, —OH or a moiety that blocks polymerase-mediated, template-directed polymerization (e.g., halo, —N$_3$, —NH$_2$, ($C_1$–$C_6$), alkoxy, methoxy, etc); and
$R^{72}$ is —OH, a phosphate ester having the formula

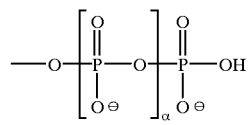

where a is an integer from 0 to 2, or a phosphate ester analog, and protected derivatives thereof. Typically, $R^{41}$ is an amide or substituted amide of the formula —NR$^{56}$—C(O)—, where $R^{56}$ is as previously described for structural formula (XXXII), but can be any covalent linkage formed between complementary reactive groups, such as those exemplified in Table 1, supra.

In a preferred embodiment of compounds according to structural formula (VI), B is a 7-deaza-purine, purine, or pyrimidine nucleobase or nucleobase analog. In a particularly preferred embodiment, B is a nucleobase or nucleobase analog selected from the group consisting of adenine, 7-deaza-adenine, cytosine, guanine, 7-deaza-guanine, thymine and uracil. When B is a purine or 7-deaza-purine, the ribose moiety is attached to the $N^9$-position of the nucleobase, and when B is a pyrimidine, the ribose moiety is attached to the N'-position of the nucleobase.

Spacer L' is attached to the various nucleobases and/or nucleobase analogs at the positions previously described in conjunction with compounds of structural formula (II). Preferred spacer arms L', spacers L, and dye chromophores D are those previously described in conjunction with compounds of structural formulae (II), (XXXIII) and (V).

In the compounds of formula (VI), when both $R^{70}$ and $R^{71}$ are —OH, the compound is a labeled ribonucleoside/tide or ribonucleoside/tide analog. When $R^{70}$ is —H and $R^{71}$ is —OH, the compound of formula (VI) is a labeled 2'-deoxyribonucleoside/tide or 2'-deoxyribonucleoside/tide analog. When $R^{70}$ and $R^{71}$ are each —H, the compound of formula (VI) is a 2',3'-dideoxyribonucleoside/tide or 2',3'-dideoxyribonucleoside/tide analog. Preferred compounds of structural formula (VI) are ribonucleoside-5'-triphosphates, 2'-deoxyribonucleoside-5'-triphosphates and 2',3'-dideoxyribonucleoside-5'-triphosphates, particularly those in which the nucleobase or nucleobase analog B is adenine, 7-deaza-adenine, cytosine, guanine, 7-deaza-guanine, thymine or uracil.

Synthesis

Conjugation typically results from mixing the compound of formula (I) and the reagent in a suitable solvent in which both are soluble, using methods well-known in the art, followed by separation of the conjugate of formula (II), e.g., labeled nucleotide/side, from any unconjugated starting materials or unwanted by-products. The dye conjugate of formula (II) can be stored dry or in solution for later use.

The labeled nucleoside/tide reagents can be synthesized, as illustrated in Scheme (III), below:

Scheme (III)

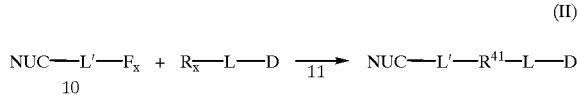

Referring to Scheme (III), reagent, e.g., a nucleoside/tide or nucleoside/tide analog, (10) modified to contain linking arm —L'—$F_x$ is condensed with an asymmetric dye including an optional linking group —L—$R_x$ (11) under conditions in which $R_x$ and $F_x$ react to form covalent linkage, thereby yielding compounds of structural formula (II). Methods for synthesizing compounds 10 are described below. In Scheme (m), NUC, L', $R^{41}$, L and D are as previously defined for structural formula (II) and $F_x$ is a functional group complementary to reactive group $R_x$ as previously described (see, e.g. Table 1). Thus, in the compounds of structural formula (II), $R^{41}$ represents the covalent linkage formed between complementary groups $R_x$ and $F_x$. In a preferred embodiment, $R^{41}$ constitutes an amide or substituted amide, especially an amide or substituted amide of the formula —$NR^{56}$—C(O)—, where $R^{56}$ is hydrogen or ($C_1$–$C_6$) alkyl. Accordingly, in a preferred embodiment, one of $R_x$ or $F_x$ according to Scheme (III) is a primary or secondary amino group having the formula —$NHR^{56}$, where $R^{56}$ is as defined supra, and the other one of $R_x$ or $F_x$ is a carboxyl or carboxylate, or an activated ester thereof.

Complementary functional group $F_x$ is attached to NUC via linkage L'. L' is analagous to L, described supra. Thus, complementary functional group $F_x$ may be attached directly to NUC, in which case L' represents a bond, or it may be spaced away from NUC by one or more intervening atoms, in which case L' represents a spacer. Any of the spacers previously defined for L can be used for spacer L'. Additional spacers L' useful for covalently conjugating the compounds of formula (I) to reagents can be found in U.S. Pat. Nos. 5,821,356, 5,770,716 and U.S. application Ser. No. 08/833,854 filed Apr. 10, 1997, the disclosures of which are incorporated herein by reference.

Referring to Scheme (III), supra, the synthesis of alkynylamino-derivatized nucleosides 10 useful for conjugating the dyes of the invention to nucleosidesitides is taught in EP 87305844.0 and Hobbs et al., 1989, J. Org. Chem. 54:3420. Briefly, the alkynylamino-derivatized nucleotides are formed by placing the appropriate halonucleoside (usually 5-iodopyrimnidine and 7-iodo-7-deazapurine dideoxynucleosides as taught by Hobbs et al., 1989, supra) and Cu(I) in a flask, flushing the flask with argon to remove air and adding dry DMF followed by addition of an alkynylamine, triethylamine and Pd(0). The reaction mixture is stirred for several hours, or until thin layer chromatography indicates consumption of the halonucleoside. When an unprotected alkynylamine is used, the alkynylamino-nucleoside can be isolated by concentrating the reaction mixture and subjecting the resulting residue to chromatography on silica gel using an eluting solvent that contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The resulting slurry can then be stirred for about 45 minutes and filtered, and the resin is then rinsed with additional ethanol/methylene chloride. The combined filtrates can be concentrated and purified using flash-chromatography on silica gel with a methanol-methylene chloride gradient. The corresponding nucleoside mono-, di- and triphosphates, as well as nucleosides/tides and nucleoside/tide analogs modified with propargylethoxyamido linker arms, are obtained by standard techniques (see, e.g., the methods described in U.S. Pat. Nos. 5,821,356, 5,770,716 and U.S. application Ser. No. 08/833,854 filed Apr. 10, 1997, discussed supra).

Additional synthesis procedures suitable for use in synthesizing compounds according to structural formula (II) are described, for example, in Gibson et al., 1987, Nucl. Acids Res. 15:6455–6467; Gebeyehu et al., 1987, Nucl. Acids Res. 15:4513–4535; Haralambidis et al., 1987, Nucl. Acids Res. 15:4856–4876; Nelson et al., 1986, Nucl. Acids Res. 5(3) :233–241; Bergstrom et al., 1989, J. Am. Chem. Soc. 111:374–375; U.S. Pat. Nos. 4,855,225, 5,231,191, and 5,449,767, the disclosures of which are incorporated herein by reference.

Any of these methods can be readily adopted or modified as necessary synthesized the full range of compounds accordingly to structural formulae (II), (XXXIII), (V) and/or (VI).

It should be noted, however, that cyanine dyes, including the compounds of formula (I), are generally not completely stable under the basic conditions typically used to deprotect and/or cleave synthetic polynucleotides from synthesis resins. Thus, any base-labile protecting groups used can be removed from the compounds of formula (II) under relatively mild basic conditions (e.g., exposure to ammonium hydroxide or 0.05 M potassium carbonate in methanol for 2 hrs. or less at a temperature of 55° C. or less or, alternatively, exposure to a 50:50 mixture of ammonium hydroxide and 40% aqueous methylamine for 90 min at room temperature or 5 mm at 65° C.). It will be appreciated that any exocyclic amines or other functionalities on the nucleoside phosphoramidites used to synthesize the labeled polynucleotides, should likewise be protected with such mild base-labile protecting groups. Suitable groups are known in the art, for example those disclosed in T. W. Greene, Protective Groups in Organic Synthesis (1981), and include, for example, isobutyryl, phenoxyacetyl, 4-isopropyl-phenoxyacetyl and acetyl. Other protecting groups having these properties will be apparent to those having skill in the art. Polynucleotide synthesis reagents and supports having appropriate base-labile linkage and protecting groups, as well as reagents for their removal and/or cleavage are commercially available (see, e.g., products catalog of Glen Research, Sterling, Va. 20164).

Phosphoramidite Reagents

Another preferred class of reagents of the invention are phosphoramidite compounds that incorporate the asymmetric cyanine dyes of formula (I). Such phosphoramidite reagents are particularly useful for the automated chemical synthesis of polynucleotides labeled with the compounds of formula (I). Such phosphoramidite reagents, when reacted with a hydroxyl group, such as a 5'-hydroxyl group of a nucleoside/tide or polynucleotide, form a phosphite ester linkage which, in turn, is oxidized to yield a phosphate ester linkage. For a detailed discussion of phosphoramidite chemistry see, e.g., Carruthers et al., U.S. Pat. Nos. 4,458,066 and 4,415,732 and Gait, 1985, *Oligonucleotide Synthesis: A Practical Approach,* IRL Press, Oxford, England. The phosphoramidite reagents can be nucleosidic or non-nucleosidic, as will be described in more detail, below.

Non-Nucleosidic Phosphoramidite Reagents

In one aspect, the phosphoramidite reagents of the invention are non-nucleosidic compounds having the formula (VII):

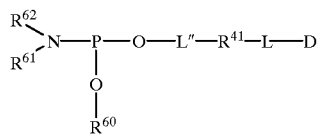

(VII)

wherein:
N, O and P represent nitrogen, oxygen and phosphorous, respectively;
L" represents a bond or a spacer as will be described more fully below;
$R^{41}$ represents a bond or a linkage as previously defined for structural formula (II);
L represents a spacer as previously defined for structural formula (I);
D represents a dye chromophore according to the invention;
$R^{60}$ is a phosphite ester protecting group;
$R^{61}$, when taken alone, is selected from the group consisting of $(C_1-C_6)$ alkyl, $(C_1-C_6)$ alkanyl, $(C_2-C_6)$ alkenyl, $(C_2-C_6)$ alkynyl, $(C_3-C_{10})$ cycloalkyl, $(C_5-C_{20})$ aryl and $(C_6-C_{26})$ arylalkyl, or when taken together with $R^{62}$ forms a straight-chain or branched $(C_2-C_{10})$ alkyleno or a straight-chain or branched 2–10 membered heteroalkyleno; and
$R^{62}$, when taken alone, is selected from the group consisting of $(C_1-C_6)$alkyl, $(C_1-C_6)$ alkanyl, $(C_2-C_6)$ alkenyl, $(C_2-C_6)$ alkynyl, $(C_3-C_{10})$ cycloalkyl, $(C_5-C_{20})$ aryl and $C_6-C_{26})$ arylalkyl, or when taken together with $R^{61}$ forms a straight-chain or branched $(C_2-C_{10})$ alkyleno or a straight-chain or branched 2–10 membered heteroalkyleno, and protected derivatives thereof.

According to structural formula (VII), $R^{60}$ is a phosphite ester protecting group which prevents unwanted extension of the polynucleotide to which the phosphoramidite is attached. Generally, $R^{60}$ is stable to polynucleotide synthesis conditions yet is able to be removed from a synthetic polynucleotide product with a reagent that does not adversely affect the integrity of the polynucleotide or the dye. A variety of phosphite ester groups having these characteristics are well-known in the art (see, e.g., Greene & Wuts, 1991, *Protective Groups in Organic Synthesis,* John Wiley & Sons, Inc., New York). Preferably, $R^{60}$ is methyl, β-cyanoethyl or 4-nitrophenylethyl.

While not depicted in structural formula (VI), dye chromophore D is attached to spacer L at the heteroaromatic imminium nitrogen or the heteroaromatic nitrogen on Z, as depicted in structural formulas (III) and (IV). In some instances, D may contain functional groups that require protection, either during the synthesis of the phosphoramidite reagent or during its subsequent use to label molecules such as polynucletodies. The protecting group(s) used will depend upon the nature of the functional groups, and will be apparent to those having skill in the art. Generally, the protecting groups used should be stable to acidic conditions commonly employed in polynucleotide synthesis employed to remove 5'-hydroxyl protecting groups (e.g., dimethoxytrityl) and shall be labile under the basic conditions used to deprotect and/or cleave synthetic polynucleotides from resins. Guidance for selecting appropriate protecting groups can be found, for example, in Greene & Wuts, 1991, *Protective Groups in Organic Synthesis,* John Wiley & Sons, Inc., New York.

Spacer L" is analogous to spacer L and therefore may be flexible or rigid, long or short, or hydrophobic or hydrophilic, depending upon the particular application. Spacer L" can be any of the previously described spacers L or L' that are stable to polynucleotide synthesis conditions. Selection of an appropriate adapter molecule will depend upon the particular application, and will be apparent to those having skill in the art. For example, spacer L" may be a $(C_1-C_{30})$, preferably a $(C_1-C_{12})$, more preferably a $(C_1-C_6)$ alkyldiyl, a $(C_1-C_{30})$, preferably a $(C_1-C_{12})$, more preferably a $(C_1-C_6)$ membered heteroalkyldiyl, a $(C_6-C_{30})$, preferably a $(C_6-C_{10})$ aryldiyl, a $(C_{12}-C_{30})$, preferably a $(C_{12}-C_{18})$ arylaryldiyl, a $(C_7-C_{30})$, preferably a $(C_7-C_{12})$ arylalkyldiyl, a $(C_7-C_{30})$, preferably a $(C_7-C_{12})$ arylheteroalkyldiyl, a $(C_6-C_{30})$, preferably a $(C_6-C_{10})$ heteroaryldiyl, a $(C_{12}-C_{30})$, preferably a $(C_{12}-C_{18})$ heteroaryl-heteroaryldiyl, a $(C_7-C_{30})$, preferably a $(C_7-C_{12})$ heteroarylalkyldiyl or a $(C_7-C_{30})$, preferably a $(C_7-C_{12})$ heteroaryl-heteroalkyldiyl. Particularly preferred spacers L" include alkylenos and heteroalkylenos, especially $(C_1-C_{30})$ alkanos and linear polyethylene oxides having the formula —$(CH_2CH_2O)_u$—$CH_2CH_2$—, where u is an integer ranging from 1 to 30, preferably from 2 to 10, and more preferably from 2 to 6.

Those of skill in the art will appreciate that compounds according to structural formula (VII) are particularly useful for labeling the 5'-terminus of synthetic polynucleotides with the asymmetric dyes of the invention. However, in many instances it may be desirable to label the 3'-terminus and/or to provide internal labels intervening the nucleosides of a synthetic polynucleotide. In these instances, spacer L" (or, alternatively spacer L) should provide a primary or secondary hydroxyl group for subsequent synthesis. The hydroxyl for subsequent synthesis is protected during the phosphitylation reaction with an acid-labile protecting group, such as those typically used to protect the primary 5'-hydroxyl of the 2'-deoxyribonucleoside phosphoramidites commonly employed in polynucleotide synthesis, as described in more detail, infra. Preferred spacers L" (or alternatively L) according to this aspect of the invention include branched ($C_1$–$C_{30}$) alkyls substituted with a primary or secondary hydroxyl. Particularly preferred phosphoramidite reagents according to this aspect of the invention are compounds according to structural formula (VIII):

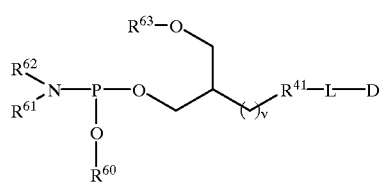

(VIII)

wherein:
N, P and O represent nitrogen, phosphorous and oxygen, respectively;
$R^{41}$, L, D, $R^{60}$, $R^{61}$ and $R^{62}$ are previously defined for structural formula (VII);
$R^{63}$ is hydrogen or an acid-labile hydroxyl protecting group; and
v is an integer from 1 to 30, preferably from 1 to 10.

In the compounds of structural formula (VIII), $R^{63}$ is hydrogen or an acid labile hydroxyl protecting group. Preferably, $R^{63}$ is a triphenylmethyl (trityl) group or a derivative thereof that is substituted with one or more of the same or different electron-donating substituents. As used herein, the term "electron-donating" refers to the tendency of a substituent to release valence electrons to neighboring atoms in the molecule of which it is a part, i.e., it is electropositive with respect to neighboring atoms. Preferably, electron-donating substituents include amino, ($C_1$–$C_6$) alkyl, ($C_1$–$C$,) aryl, ($C_1$–$C_6$) alkoxy, and the like. More preferably, the electron-donating substituent(s) are methoxy. Exemplary acid-labile trityl derivatives include 4,4'-dimethoxytrityl, i.e. bis(p-anisyl)phenylmethyl, monomethoxytrityl, a-naphthyldiphenylmethyl, tri(p-methoxyphenyl)methyl, and the like. Attachment and cleavage conditions for these and other trityls can be found in Greene and Wuts, 1991, *Protective Groups in Organic Synthesis*, 2$^{nd}$ Ed., John Wiley & Sons, New York, and Gait, 1985, *Oligonucleotide Synthesis: A Practical Approach*, IRL Press, Oxford, England.

In a preferred embodiment of the invention, in the compounds of structural formulae (VII) and (VIII), $R^{61}$ and $R^{62}$ are taken alone and are each independently a branched or straight-chain ($C_1$–$C_6$) alkyl, more preferably a branched or straight-chain ($C_1$–$C_6$) alkanyl. In a particularly preferred embodiment, $R^{61}$ and $R^{62}$ are each independently propan-2-yl (isopropyl), butan-2-yl, butan-3-yl, 2-methyl-propan-1-yl (iso-butyl) or 2-methyl-propan-2-yl (t-butyl).

In another preferred embodiment, $R^{61}$ and $R^{62}$ are taken together and form a straight chain ($C_2$–$C_5$) alkanyleno bridge or a ($C_2$–$C_{10}$) branched alkanyleno bridge in which the principle chain or bridge contains from 2 to 5 carbon atoms. In an alternative preferred embodiment, $R^{61}$ and $R^{62}$, when taken together with the nitrogen atom, form a 5–8 membered heteroalkyl, optionally containing one or more additional heteroatoms selected from the group consisting of nitrogen, oxygen and sulfur. In a particularly preferred embodiment, $R_{61}$ and $R_{62}$, when taken together with the nitrogen atom, form a morpholino group.

Phosphoramidite reagents according to structural formulae (VI) and (VIII) can be synthesized by a variety of known methods. Hydroxyls and other reactive functionalities of the chromophore of the compounds of formula (I) are protected with protecting groups that can be removed under the desired conditions, commonly with a DNA synthesis deprotection agent, such as ammonia, ethanolamine, methylamine/ammonium hydroxide mixtures, and mixtures of tbutylamine/water/methanol (1:2:1) (see, e.g., U.S. Pat. No. 5,231,191). Preferred protecting groups include esters of benzoic acid or pivalic acid. Most preferably, the protecting groups are removable under mildly basic conditions, as described supra.

Nucleosidic Phosphoramidite Reagents

In a second preferred embodiment, the phosphoramidite reagents of the invention are 2'-deoxyribonucleoside-5'-phosphoramidites according to structural formula (IX):

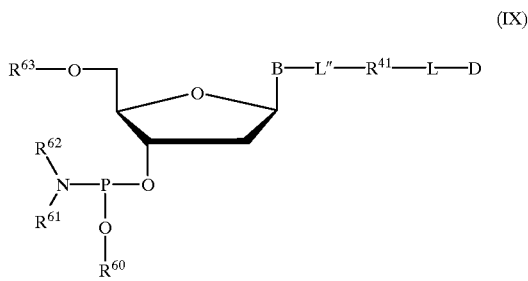

(IX)

wherein:
B is a nucleobase or nucleobase analog;
L", $R^{41}$, L, D, $R^{60}$, $R^{61}$ and $R^{62}$ are as previously described for structural formula (VII); and
$R^{63}$ is as previously described for structural formula (VIII), and protected derivatives thereof.

When B is a purine or 7-deazapurine, the 2'-deoxyribose moiety is attached to the $N^9$-position of the purine or deazapurine. Alternatively, when B is a pyrimidine, the 2'-deoxyribose moiety is attached at the $N^1$-position of the pyrimidine. B and D are linked through linkage —L"—$R^{41}$—L—, typically formed by the reaction of complementary reactive and functional groups, as described in detail above. If B is a purine, U is attached to the C-8 position of the purine, while if B is a 7-deazapurine, L" is attached to the C-7 position of the 7-deazapurine. If B is a pyrimidine, L" is attached to the C-5 position of the pyrimidine. L" is attached to the same position of the various nucleobase analogs, or to corresponding positions or will be apparent to those of skill in the art.

As will be recognized by those of skill in the art, the exocyclic amines and other functionalities of nucleobase or nucleobase analog B may require protection during the synthesis of the phosphoramidite reagent and/or during its subsequent use to synthesize labeled polynucleotides. The particular protecting group(s) selected will depend on the identity of the nucleobase or nucleobase analog, and will be apparent to those of skill in the art. Generally, protecting groups commonly used in the art of nucleic acid synthesis are used. For example, the exocyclic amines of adenine and cytosine can be protected with benzoyl (Bz) and the exocyclic amine of guanine can be protected with isobutyryl (iBu) using conventional N-acylating procedures. The $Q^6$ amide oxygen of guanine, as well as the $Q^4$ amide oxygen of thymine and/or uracil can also be optionally protected with, for example, phosphinothioyl, 2-nitrophenyl or substituted ethyl groups (e.g. cyanoethyl) using conventional techniques (see, e.g., Deskalov et al., 1981, Bull. Chem. Soc. Japan 54:3076; Jones et al., 1981, Tetrahedron Lett. 22:4755; Gaffney & Jones, 1982, Tetrahedron Lett. 23:2257; Trichtinger et al., 1983, Tetrahedron Lett. 24:211; Himmeisbach et al., 1981, Tetrahedron Lett. 40:59).

Preferably, the nucleobase or nucleobase analog is protected with groups that are readily removed under mild basic conditions, as previously described. Protecting groups removable under such mild basic conditions are well-known. For example, polynucleotides synthesized with one or more nucleotide phosphoramidites having protecting groups, e.g., $dA^{Bz}$, $dC^{Bz}$, $dG^{iBu}$ and dT (and their corresponding resins), can be cleaved and deprotected in 90 minutes or less using a 50:50 mixture of ammonium hydroxide and 40% aqueous methylamine (Aldrich, catalog no. M2, 775-1), depending upon the temperature (5 minutes at 65° C.; 90 minutes at 25° C.). Polynucleotides synthesized with $dA^{iBz}$, $dA^{Pac}$, $dC^{Ac}$, $dG^{iPr-iPac}$ and dT phosphoramidites (and their corresponding resins) can be cleaved and deprotected in 2 hours at room temperature with animonium hydroxide or 0.05 M potassium carbonate in 3methanol. Thus, preferred exocyclic amine protecting groups for adenine are benzoyl (Bz), isobutyryl (iBu) and phenoxyacetyl (Pac). Preferred exocyclic amine protecting groups for cytosine are Bz and acetyl (Ac). Preferred exocyclic amine protecting groups for guanine are iBu and 4-isopropyl-phenoxyacetyl (iPr-Pac). The actual protecting group selected for a particular nucleobase will depend upon the protection of the other nucleobase and will be apparent to those of skill in the art.

Preferred compounds according to structural formula (IX) include those compounds in which L" is —CC—CH$_2$— NH—, and L, D, $R^{60}$, $R^{61}$, $R^{62}$ and/or $R^{63}$ are their respective preferred embodiments previously described in connection with structural formula (VII) or (VIII).

Labeled 2'-deoxyribonucleoside-3'-phosphoramidites according to structural formula (IX) are particularly well suited for providing labels at the 3', 5' and/or internal positions of chemically-synthesized polynucleotides.

Synthesis

The phosphoramidite portion of the molecule is linked to dye chromophore D via linkage —L'—$R^{41}$—L—. As discussed in more detail above, the linkage —L'—$R^{41}$—L— can take a variety of forms, but generally must be a linkage that is (i) stable to DNA synthesis conditions; and (ii) does not substantially interfere with oligonucleotide-target hybridization; e.g., U.S. Pat. Nos. 5,231,191, 5,258,538, 4,757,141 and 5,212,304.

The composition of—L'—$R^{41}$—L— is in part dictated by the methods used to synthesize the phosphoramidite reagents. For example, appropriately protected asymmetric dyes according to structural formula (I) in which the linking group substituent includes a primary (or secondary?) hydroxyl group (e.g., linking group has the structure —L—OH) can be conveniently phosphitylated using standard methods and reagents to yield phosphoramidites according to structural formula (VII). In these instances, L is any of the previously-described spacers that is compatible with polynucleotide synthesis conditions and —L"—$R_{11}$ constitutes a bond.

Alternatively, where the linking group of structural formula (II) does not include a primary or secondary hydroxyl group for phosphitylation, an appropriately protected dye according to structural formula (I) in which linking group has the structure —L—$R_x$, where $R_x$ is a reactive group as previously described, can be conveniently "converted" to include a primary or secondary hydroxyl by reacting the dye with an "adapter molecule" which has a primary or secondary hydroxyl and a functional group complementary to reactive group $R_x$, such as any of the previously-described complementary functional groups $F_x$ (see, e.g., Table 1, supra). Analogous to the compounds of structural formula (II), in the compounds of structural formula (VII), the reaction between reactive group $R_x$ and functional group $F_x$ form linkage $R^{41}$. The oxygen intervening the phosphorous atom and spacer L" is contributed by the adapter molecule. Thus, adapter molecules useful for providing a hydroxyl group suitable for phosphitylation are generally compounds having the structure $R^{63}$—O—L"—$F_x$, where $R^{63}$ is hydrogen or a hydroxyl protecting group, preferably an acid-labile hydroxyl protecting group as described in more detail, infra. Preferably, $F_x$ is an amine of the formula —NHR$^{56}$, where $R^{56}$ is as previously defined, and reactive group $R_x$ of the dye is a carboxyl or carboxylate, or an activated ester thereof, such that $R^{41}$ in the compounds of structural formula (VII) is an amide or substituted amide having the formula —NR$^{56}$—C(O)—, where $R^{56}$ is as previously described.

Any hydroxyl groups on L, L', or L" for subsequent synthesis are protected with an acid-labile protecting group, preferably 4,4'-dimethoxytrityl, prior to phosphitylation. If the linking group of the protected dye includes a primary or secondary hydroxyl, it can be phosphitylated according to standard methods. If the linking group contains reactive group $R_x$, such as, for example, a carboxyl group, it can be activated, e.g., with a carbodiimide, and reacted with an adapter molecule, e.g., ethanolamine, hexanol amine, or the like, in N,N-dimethylformamide (DMF), or another similar aprotic solvent to yield a protected dye with a hydroxyl functionality. The hydroxyl group is then reacted with a phosphitylating agent using standard procedures, e.g., using di-(N,N-diisopropylamino)methoxyphosphine in acetonitrile containing catalytic amounts of tetrazole diisopropylamine, to yield the phosphoramidite (see, e.g., U.S. Pat. No. 5,231,191).

The 2'-deoxyribonucleoside phosphoramidites according to structural formula (IV) can be synthesized using standard methods, as is illustrated in Scheme (IV), below, with propargyl spacers L', carboxyl reactive groups Rh and primary amino complementary functional groups $F_x$.

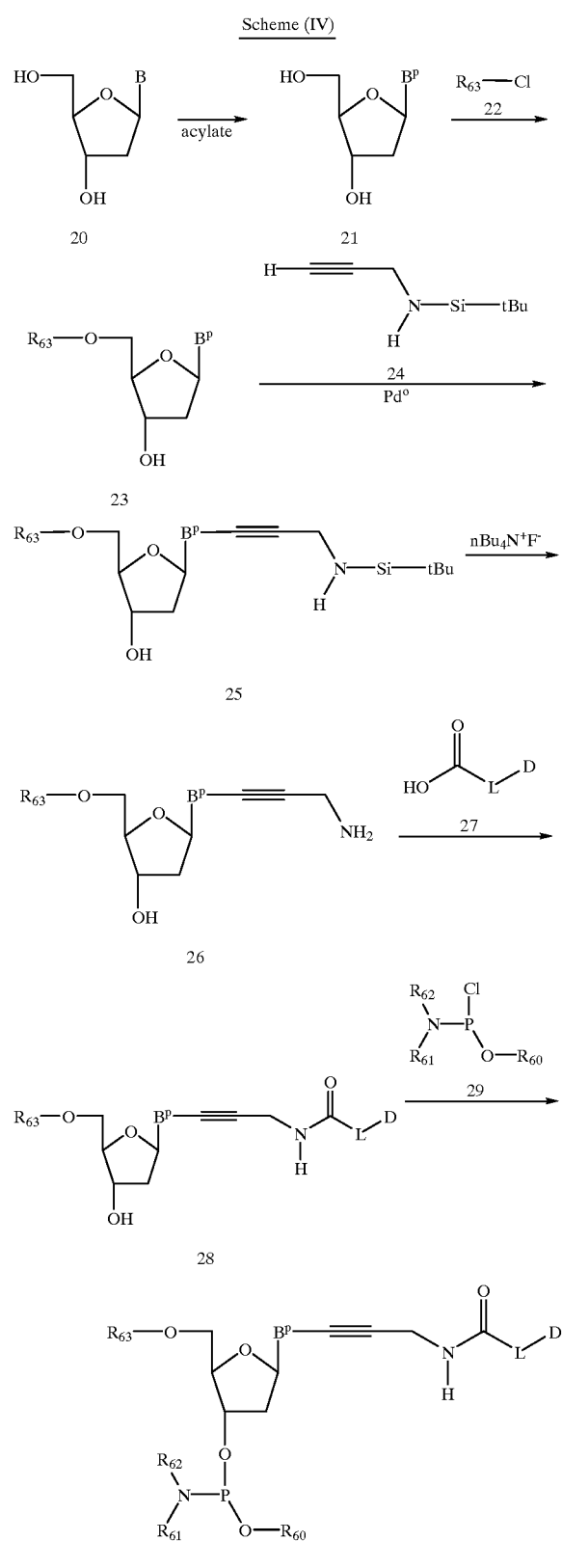

Scheme (IV)

In Scheme (IV), $R^{60}$, $R^{61}$, $R^{62}$, $R^{63}$, B, L and D are as previously defined for structural formula (VIII) and B" is a protected nucleobase or nucleobase analog.

According to Scheme (IV), nucleoside 20 is N-acylated using standard procedures to protect any exocyclic amines, yielding protected nucleoside 21. Protected nucleoside 21 is reacted with chloride 22 (e.g., 4,4'-dimethoxytritylchloride) to yield 5'-protected nucleoside 23. Compound 23 is reacted with compound 24 in the presence of palladium(0), yielding protected propargyl linker-modified nucleoside 25. The t-butylsilyl protecting group of the propargylamino linker is selectively removed with a source of fluoride ion, preferably NaF or $nBu_4N^+F^-$, to yield protected nucleoside 26. Next, the protected nucleoside 26 is labeled with the dye by reacting it with dye 27 under conditions in which the reactive group of the dye react with the complementary functional group of the protected nucleoside to form a covalent linkage, In the specific example illustrated in Scheme (IV), the reactive carboxyl of dye 27 is conveniently converted to a reactive ester, e.g., a NHS ester, with dicyclohexyl carbodiimide and N-hydroxysuccinimide. The activated NHS ester then reacts with compound 26 to yield dye-labeled nucleoside 28, which is phosphitylated with compound 29 to yield phosphoramidite 30. Any reactive groups on dye chromophore D or linker L can be protected as previously described. Methods of synthesizing compounds according to structural formula (VIII) including spacers L' and linkages $R^{41}$ other than those depicted in Scheme (VIII) can be synthesized by routine modification of the above method, by resort to other conventional synthetic methods (see, e.g., Meyer, "Incorporation of Modified Bases into Oligonucleotides," In. *Methods in Molecular Biology Volume 26: Protocols for Oligonucleotide Conjugates*, Chapter 2, Agarwal, Ed., 1994, Humana Press, Totowa, N.J., as well as the references cited therein), or by routine modification of the methods provided in connected with the compounds of structural formula (V).

Dye Pairs Including Non-Fluorescent Cyanine Dyes

Reporter-quencher dye pairs may comprise any pair of molecules that participate in an energy transfer process. Exemplary reporters are fluorescent and may be selected from xanthene dyes, including fluoresceins, and rhodamine dyes. Many suitable forms of these compounds are commercially available having various substituents on their xanthene rings that can be used as a site for bonding or as the bonding functionality for attachment to a reagent, preferably an oligonucleotide. Another group of fluorescent reporters are the naphthylamines and their derivatives, having an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include but are not limited to coumarins, such as 3-phenyl-7-isocyanatocoumarin; acridines, such as 9-isothiocyanatoacridine and acridine orange; N-(p-(2-benzoxazolyl)phenyl)maleimide; cyanines; BODIPY™ dyes; benzoxadiazoles; stilbenes; pyrenes; and the like.

Preferably, reporter molecules are selected from fluorescein and rhodamine dyes. These dyes and appropriate linking methodologies for attachment to oligonucleotides are described elsewhere (Khanna et al. U.S. Pat. No. 4,439,356; Marshall (1975) *Histochemical J.,* 7:299–303; Menchen et al., U.S. Pat. No. 5,188,934; Menchen et al., European Patent Application No. 87310256.0; and Bergot et al., International Application PCT/U590/05565). Particularly preferred reporter molecules include fluorescein dyes NED, TET and FAM.

Exemplary reporter-quencher pairs include the following:

| Reporter | Quencher |
|---|---|
| FAM | Nitothiazole Orange (9) |
| FAM | Nitothiazole Blue (XXXIV) |
| TET | Nitothiazole Blue (XXXIV) |
| TET | Nitothiazole Blue (XXXIV) |
| NED | Nitothiazole Blue (XXXIV) |

One embodiment of the present invention includes compositions comprising a reporter dye and a quencher dye, wherein the quencher dye is a compound according to formula (I). Preferably, the reporter dye is selected from the group consisting of xanthene, coumarin, napthylamine, cyanine, and BODIPY™ dyes. More preferably, the reporter dye is a xanthene dye. Most preferably, the xanthene dye is selected from the group consisting of fluorescein dyes and rhodamine dyes.

Such reporter/quencher compositions are useful, for example (but without any limitation), in determining how well matched are the reporter and quencher dyes with each other with respect to the ability of the quencher to quench the fluorescence of the reporter. Such compositions are also useful, for example (and without limitation), in the various assays including those described in the examples, below. Preferably, compositions comprising a reporter and a quencher also include a solvent system in which one or both of the reporter and quencher are soluble. Such solvents are well known to those in the art, and include (but are not limited to) water; water/surfactant mixtures; halogenated hydrocarbons, including (but not limited to) dichloromethane, chloroform, carbon tetrachloride and polychlorinated ethanes and ethenes; aromatic solvents including (but not limited to) benzene, toluene, xylenes, and the like; alcohols including but not limited to methanol, ethanol, ethylene glycol, and isopropanol; ethers such as (but not limited to) diethyl ether, and polyethylene glycol derivatives such as (but not limited to) digols; ketones such as (but not limited to) acetone and methyl ethyl ketone/dimethylsulfoxide; tetrahydrofuran; N-methylpyrrolidinone; dimethylformamide; and the like.

Dye-Labeled Polynucleotides

Structure

Yet another preferred class of reagents of the present invention comprise polynucleotides or polynucleotide analogs labeled with the compounds of formula (I). Such labeled polynucleotides or analogs are useful in a number of important contexts, including as DNA sequencing primers, PCR primers, oligonucleotide hybridization probes, oligonucleotide ligation probes, and the like. In some cases polynucleotides or analogs labeled with fluorescent reporter dyes are used in conjunction with polynucleotides or analogs labeled with a compound of formula (I). The labeled polynucleotides can also have a reporter dye attached thereto. These reporter-labeled polynucleotides and analogs are made by incorporating reporter-labeled nucleotides into polynucleotides using standard synthetic methods and as described, below.

In one preferred embodiment, the labeled polynucleotides or polynucleotide analogs of the present invention include one or more compounds of formula (I). Such labeled polynucleotides are useful in the assay methods as described below.

In another preferred embodiment, the reagents include one or more compounds of formula (I) and correspondingly one or more fluorescent reporter dyes, all of which are located such that fluorescence energy transfer takes place between the one or more reporter dyes and the compounds of formula (1). Such multiply labeled polynucleotides are useful in various assays, particularly the "Taqman" assay as described, below.

Generally, the design of oligonucleotide hybridization probes labeled with the compounds of formula (I) follows conventional teachings. Thus, in designing labeled oligonucleotide hybridization probes, the following general guidelines are preferably followed: (i) if the target nucleic acid sequence is located within a PCR amplicon, the probe sequence should be such that the probe hybridizes at a location on the sequence between the PCR primers; (ii) probes should be about 20–30 nucleotides long so as to ensure good hybridization kinetics and specificity of binding; (iii) the sequence of the probe should be such that there is no internal base pairing in the probe, thus avoiding the formation of secondary structure (e.g., stem-loop structures); (iv) if the probe is being used in combination with PCR primers, it should not hybridize to the primers; (v) probes with more than four contiguous identical bases should be avoided; and (vi) when choosing between a probe sequence and its complement, the probe sequence should have more C nucleotides than G nucleotides.

Synthesis

Labeled polynucleotides and/or polynucleotide analogs may be synthesized using methods known to those in the art either enzymatically, e.g. using a DNA polymerase or ligase (see, e.g., Stryer, 1981, *Biochemisty,* Chapter 24, W. H. Freeman and Company), or by chemical synthesis, e.g., by the phosphoramidite method, the phosphite-triester method, and the like (see, e.g., Gait, 1990, *Oligonucleotide Synthesis,* IRL Press, Oxford, England). Labels (reporters and the compounds of formula (I)) may be introduced during enzymatic synthesis utilizing the labeled nucleoside-5'-triphosphate monomers described above, or during chemical synthesis using the labeled non-nucleosidic or nucleosidic phosphoramidite reagents described above.

"Xanthene dyes" are dyes that comprise the following fused three-ring structure:

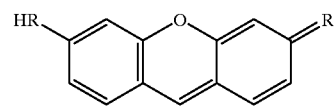

where R is oxygen (fluorescein) or NH (rhodamines), including substituted forms thereof.

Exemplary substituted fluorescein compounds include the "NED" dye, which has the structure:

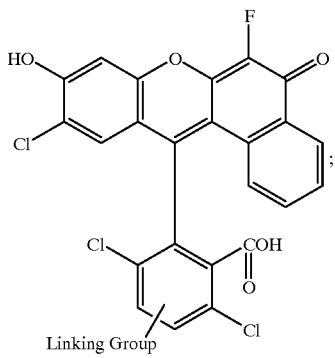

the "TET" dye, which has the structure:

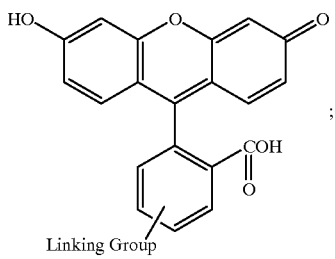

and the "FAM" dye, which has the structure:

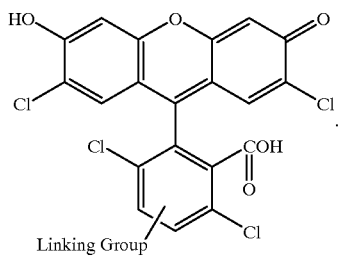

An exemplary rhodamine dye is the "TAMRA," also known as the "TMR," dye, which has the structure:

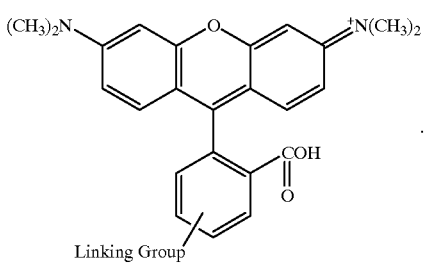

Another exemplary rhodamine dye are the dichlororhodamine dyes (U.S. Pat. No. 5,847,162) having the structure:

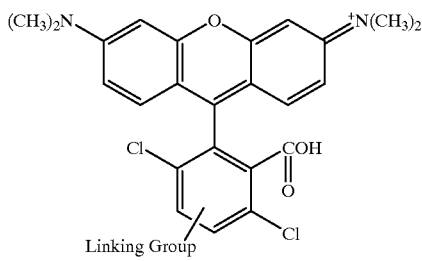

"Coumarin dyes" are dyes that comprise the following fused two-ring structure:

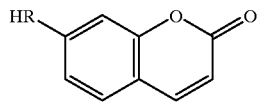

where R is oxygen (hydroxycoumarin) or NH (aminocoumarin), including substituted forms thereof.

"BODIPY™ dyes" are dyes comprising the following fused ring structure:

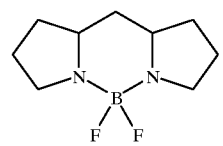

including substituted forms thereof. For examples of additional BODIPY™ dyes, see Haugland (1996) *Handbook of Fluorescent Probes and Research Chemicals, Sixth Addition,* (Molecular Probes, Inc.), Chapter 1, Section 1.2.

Reporter dye-labeled nucleotides can be purchased from, e.g., Sigma-Aldrich, St. Louis, Mo. (1999 Catalog, p. 1587). Alternatively, they can be synthesized by well-known means (see, e.g., *Handbook of Fluorescent Probes and Research Chemicals, Sixth Addition,* Section 8.2). In one embodiment, such reporter-nucleotide compounds can be made in an analogous fashion to quencher-nucleotide compounds. Functionalized reporter dyes for labeling of nucleic acids and other biomolecules can be purchased from, e.g., Molecular Probes, Inc., Eugene, Oreg. (http://www.probes.com).

Singly- or doubly-labeled polynucleotides may be prepared using any of a number of well known methods. Methods suitable for labeling an oligonucleotide at the 3'-end include but are by no means limited to: (i) periodate oxidation of a 3'-terminal ribonucleotide, followed by reaction with an amine-containing label (Heller & Morrison (1985) in *Rapid Detection and Identification of Infectious Agents,* D. T. Kingsbury and S. Falkow, eds., pp 245–256, Academic Press); (ii) enzymatic addition of a 3'-aliphatic amine-containing nucleotide using deoxynucleotidyl transferase, followed by reaction with an amine-reactive label (Morrison, European Patent Application No. 232 967); and (iii) periodate oxidation of a 3'-ribonucleotide, followed by reaction with 1,6-hexanediamine to provide a 3'-terminal aliphatic amine, followed by reaction with an amine-reactive label (Cardullo et al. (1988) *Proc. Natl. Acad. Sci. USA,* 85: 8790–8794).

Generally, if the labeled polynucleotide is made using enzymatic synthesis, the following procedure may be used:

A target DNA is denatured and an oligonucleotide primer is annealed to the template DNA. A mixture of 2'-deoxyribonucleoside-5'-triphosphates capable of supporting template-directed enzymatic extension of the primed target (e.g., a mixture including dGTP, dATP, dCTP, and dTTP) is added to the primed target. At least a fraction of the deoxynucleotides is labeled with a compound of formula (1) as described above. Next, a polymerase enzyme is added to the mixture under conditions where the polymerase enzyme is active. A labeled polynucleotide is formed by the incorporation of the labeled deoxynucleotides during polymerase-mediated strand synthesis. In an alternative enzymatic synthesis method, two primers are used instead of one: one complementary to the +strand of the target and another complementary to the −strand of the target, the polymerase is a thermostable polymerase and the reaction temperature is cycled between a denaturation temperature and an extension temperature, thereby exponentially synthesizing a labeled complement to the target sequence by PCR, (see, e.g., *PCR Protocols,* 1990, Innis et al. Eds., Academic Press).

Labeled polynucleotides or polynucleotide analogs may also be chemically synthesized using the phosphoramidite or other solution or solid-phase methods. Detailed descriptions of the chemistry used to form polynucleotides by the phosphoramidite method are provided elsewhere (see, e.g., Caruthers et al., U.S. Pat. Nos. 4,458,066 and 4,415,732; Caruthers et al., 1982, Genetic Engineering 4:1–17; *Users Manual Model* 392 *and* 394 *Polynucleotide Synthesizers,* 1990, pages 6-1 through 6-22, Applied Biosystems, Part No. 901237).

The phosphoramidite method of polynucleotide synthesis is the preferred method because of its efficient and rapid coupling and the stability of the starting materials. The synthesis is performed with the growing polynucleotide chain attached to a solid support, such that excess reagents, which are in the liquid phase, can be easily removed by decanting, filtration, etc., thereby eliminating the need for purification steps between synthesis cycles.

The following briefly describes the steps of a typical polynucleotide synthesis cycle using the phosphoramidite method. First, a solid support including a protected nucleoside monomer is treated with acid, e.g., trichloroacetic acid, to remove the 5'-hydroxyl protecting group, freeing the hydroxyl for a subsequent coupling reaction. An activated intermediate is then formed by simultaneously adding a protected nucleoside phosphoramidite monomer and a weak acid, e.g., tetrazole, to the reaction. The weak acid protonates the nitrogen atom of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g. trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and any protecting groups on the dyes are removed by treating the polynucleotide solution in base at an elevated temperature, e.g., 55° C. Preferably the various protecting groups removed using the mildly basic conditions previously described.

Any of the nucleoside phosphoramidite monomers may be dye-labeled phosphoramidites as described above. If the 5'-terminal position of the nucleotide is labeled, a labeled non-nucleotidic phosphoramidite of the invention may be used during the final condensation step. If the 3'-terminal position or one or more internal position of the oligonucleotide are labeled, a labeled nucleosidic phosphoramidite of the invention may be used during any of the condensation steps or, alternatively, using the non-nucleosidic phosphoramidites of the invention.

Methods for labeling the 5' end of an oligonucleotide include but are by no means limited to: (i) periodate oxidation of a 5'-to-5'-coupled ribonucleotide, followed by reaction with an amine-reactive label (Heller & Morisson (1985) in *Rapid Detection and Identification of Infectious Agents,* D. T. Kingsbury and S. Falkow, eds., pp 245–256, Academic Press); (ii) condensation of ethylenediamine with 5'-phosphorylated polynucleotide, followed by reaction with an amine reactive label (Morrison, European Patent Application 232 967); and (iii) introduction of an aliphatic amine substituent using an aminohexyl phosphite reagent in solid-phase DNA synthesis, followed by reaction with an amine reactive label (Cardullo et al. (1988) *Proc. Natl. Acad. Sci. USA,* 85: 8790–8794).

In addition to these end-labeling methods, labels can be placed at specific locations within synthetic polynucleotides using amine-containing nucleotide phosphoramidite reagents, e.g., 5'-dimethoxytrityl-5-(N-trifluoroacetylaminohexyl-3-acrylimido)-2-deoxyuridine 3'-((2-cyanoethyl)-(N,N-diisopropyl))phosphoramidite e.g., Amino-Modifier C6 dT phosphoramidite (Linker Arm Nucleotide, Glen Research, Inc.) (Mathies et al., U.S. Pat. No. 5,688,648).

For a thorough review of oligonucleotide labeling procedures see R. Haugland (1983) in *Excited States of Biopolymers,* (Steiner ed., Plenum Press); *Fluorogenic Probe Design and Synthesis: A Technical Guide,* PB Applied Biosystems (1996); and G. T. Herman (1996) *Bioconjugate Techniques,* (Academic Press).

Hybridization Methods Utilizing Non-Fluorescent Cyanine Dyes as Quencher Molecules Several hybridization assay formats that employ energy transfer as a means for detecting hybridization have been described, five of which are discussed below and shown schematically in FIGS. 5A–E. These assays are useful for, e.g., detecting the presence of a specific nucleotide sequence in a nucleic acid sample, detecting the presence of contiguous sequences on a target nucleic acid, for detecting the presence of mutations within a target nucleic acid sequence, monitoring the kinetics of nucleic acid hybridization, and monitoring the progression of PCR reactions.

Figure 5A:
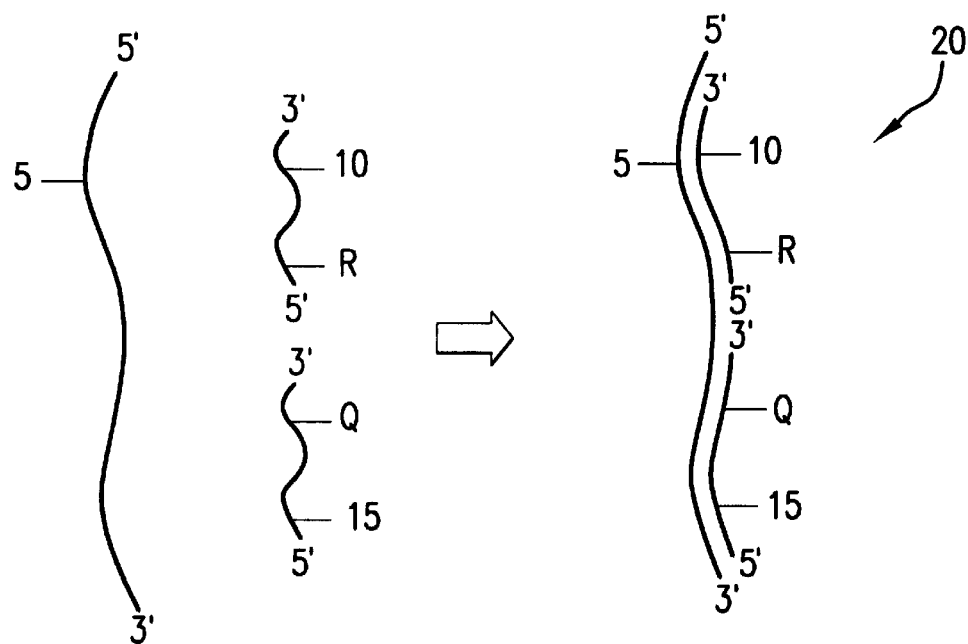
FIGS. 5A–5E show a schematic depiction of several hybridization detection methods according to the present invention.

In a first assay format, shown in FIG. 5A, the sequences of two oligonucleotide probes are selected such that they will hybridize to contiguous regions of a target nucleic acid 5. The first probe 10, hybridizing toward the 5'-terminus of the target nucleic acid, is labeled near its 5'-terminus with a reporter label, whereas the second probe 15 is labeled near its 3'-terminus with a quencher label. Thus, when a 3-way hybrid 20 is formed among the target nucleic acid 5 and the first 10 and second 15 probes, the reporter and quencher are brought into close proximity and energy transfer can take place. Thus, in this format, the emission of the reporter is quenched upon the hybridization of the two probes to the target. (Heller et al., European Patent Publication No. EP 070 685 (1983)).

Figure 5B:
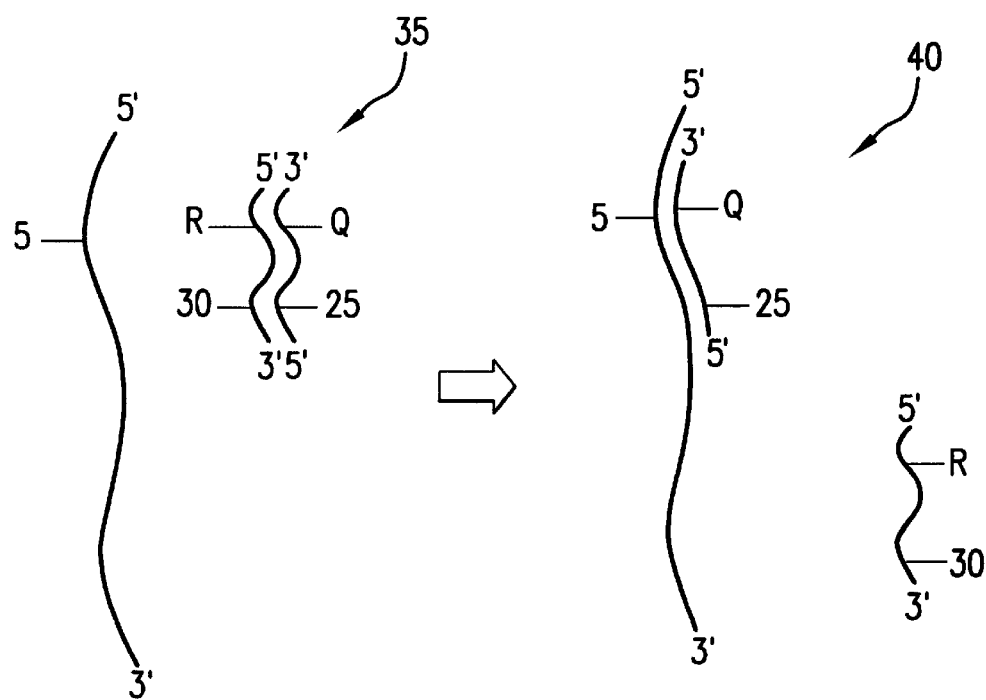

In a second assay format, shown in FIG. 5B, two oligonucleotide probes 25 and 30 that are complementary to each other, one of which contains a reporter label and the other of which contains a quencher label, are used. The location of the labels is selected such that when the probes are hybridized to each other to form the double-stranded, probe-probe hybrid 35, the quenching interaction is favored, whereas an insignificant amount of quenching occurs when the probes are separated. The detection of target nucleic acid is achieved by denaturing both the target nucleic acid 5 and the probes 25 and 30, and then allowing the strands to reanneal. Thus, there is a competition between probe-probe hybridization and probe-target hybridization. The more target nucleic acid that is present, the larger the number of probes that will hybridize to the target, forming probe-target hybrids 40. The presence of target DNA is indicated by an increased emission from the reporter R due to the reduced quenching by the quencher Q caused by a reduction in the number of probe-probe hybrids. (Morrison, European Patent Application 232 967 (1987)).

Figure 5C:
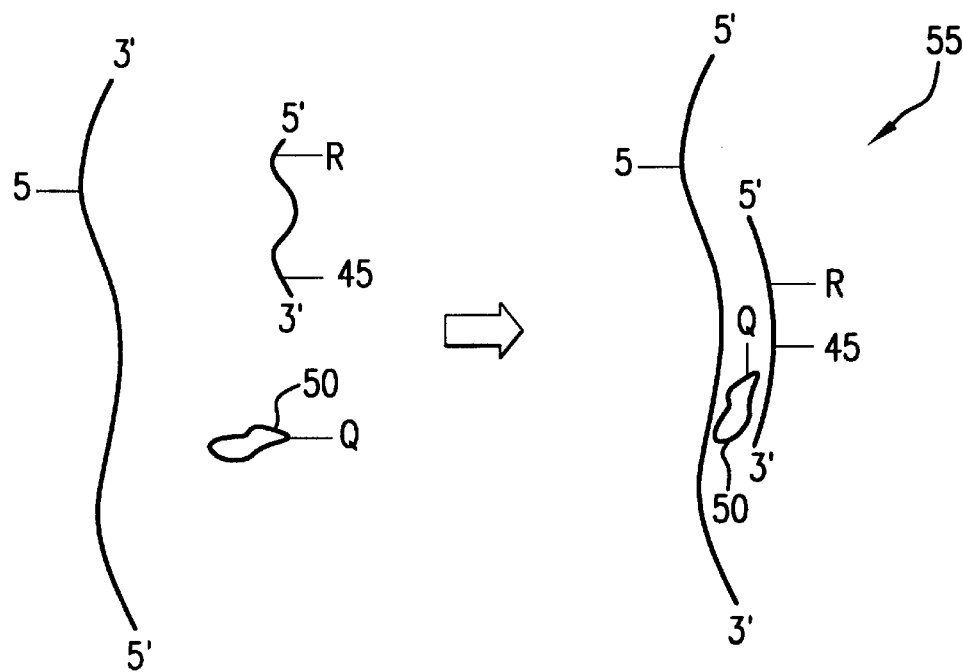

A third assay format, depicted in FIG. 5C, uses only one probe labeled with a reporter 45 and a quencher dye that binds preferentially to double-stranded nucleic acid 50. This quencher dye 50 may intercalate between the base pairs of the double-stranded species or it may bind in the major or minor grooves or to the backbone of the double helix. Thus, in the absence of hybridization, the quencher Q does not bind to the single-stranded probe 45, and the reporter R is unaffected by Q. However, in the presence of a complementary nucleotide sequence within the target nucleic acid 5, the probe 45 hybridizes to the target nucleic acid and Q binds to the resulting double-stranded region forming a target-probe-dye complex 55. In the complex, Q and R are placed in close proximity and energy transfer or fluorescence quenching may take place. Thus, in this format, the emission of the reporter is quenched upon the hybridization of the probe to the target. (Heller & Morrison (1985) in *Rapid Detection and Identification of Infectious Agents,* D. T. Kingsbury and S. Falkow, eds., pp 245–256, Academic Press).

Figure 5D:
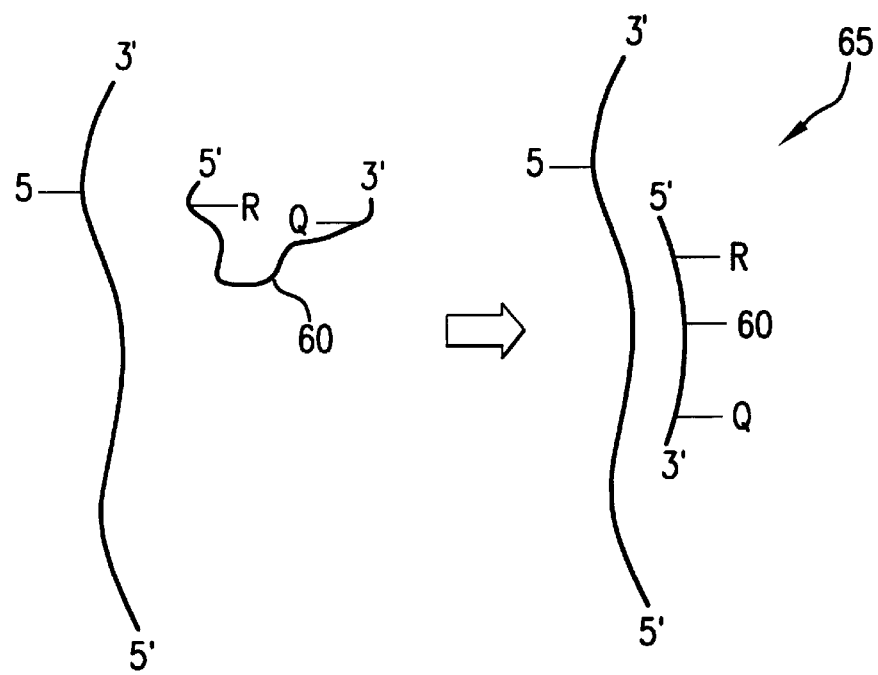

In a fourth assay format, shown in FIG. 5D, a single oligonucleotide probe 60 is used. Probe 60 is labeled with both a reporter and a quencher. The location of the reporter and quencher labels is selected so that when the probe is not hybridized to a target nucleic acid, the conformation of the probe is such that the reporter and quencher labels are in close proximity, thereby allowing energy transfer to take place. The reporter dye can be attached to the 3' end of the probe and the quencher dye can be attached to the 5' end; alternatively, the reporter dye can be attached at the 5' end of the probe and the quencher dye can be attached at the 3' end. In one embodiment, the reporter and quencher are brought into close proximity by designing the probe sequence such that a hairpin forms at the ends of the probe, thereby putting the reporter and quencher molecules in close enough proximity for energy transfer (Bagwell, European patent Application No. 601 889 (1994); Tyagi & Kramer (1996) *Nature Biotechnology,* 14:303–308). In another embodiment, the reporter and quencher are located far enough apart on the probe such that the random-coil confirmation of the single-stranded probe serves to bring the quencher and reporter into sufficiently close proximity so that the quencher quenches the emission of the reporter dye (Mayrand, U.S. Pat. No. 5,691,146). When the double-labeled probe 60 is hybridized to a target nucleic acid 5 forming a probe-target hybrid 65, the reporter and quencher are separated from one another, and the quenching interaction is prevented. In other words, the location of the reporter dye and the quencher dye is such that when the probe is hybridized to a target nucleic acid sequence, the reporter dye is not effectively quenched by the quencher dye. Likewise, when the probe is not hybridized to a target nucleic acid sequence, the reporter dye is effectively quenched by the quencher dye. Preferably, when the reporter dye is quenched by the quencher dye, its fluorescence is reduced by at least a factor of two, more preferably by at least a factor of six, when compared to its fluorescence when it is not effectively quenched. Thus, in this format, the emission of the reporter becomes unquenched upon the hybridization of the probe to the target.

Figure 5E:
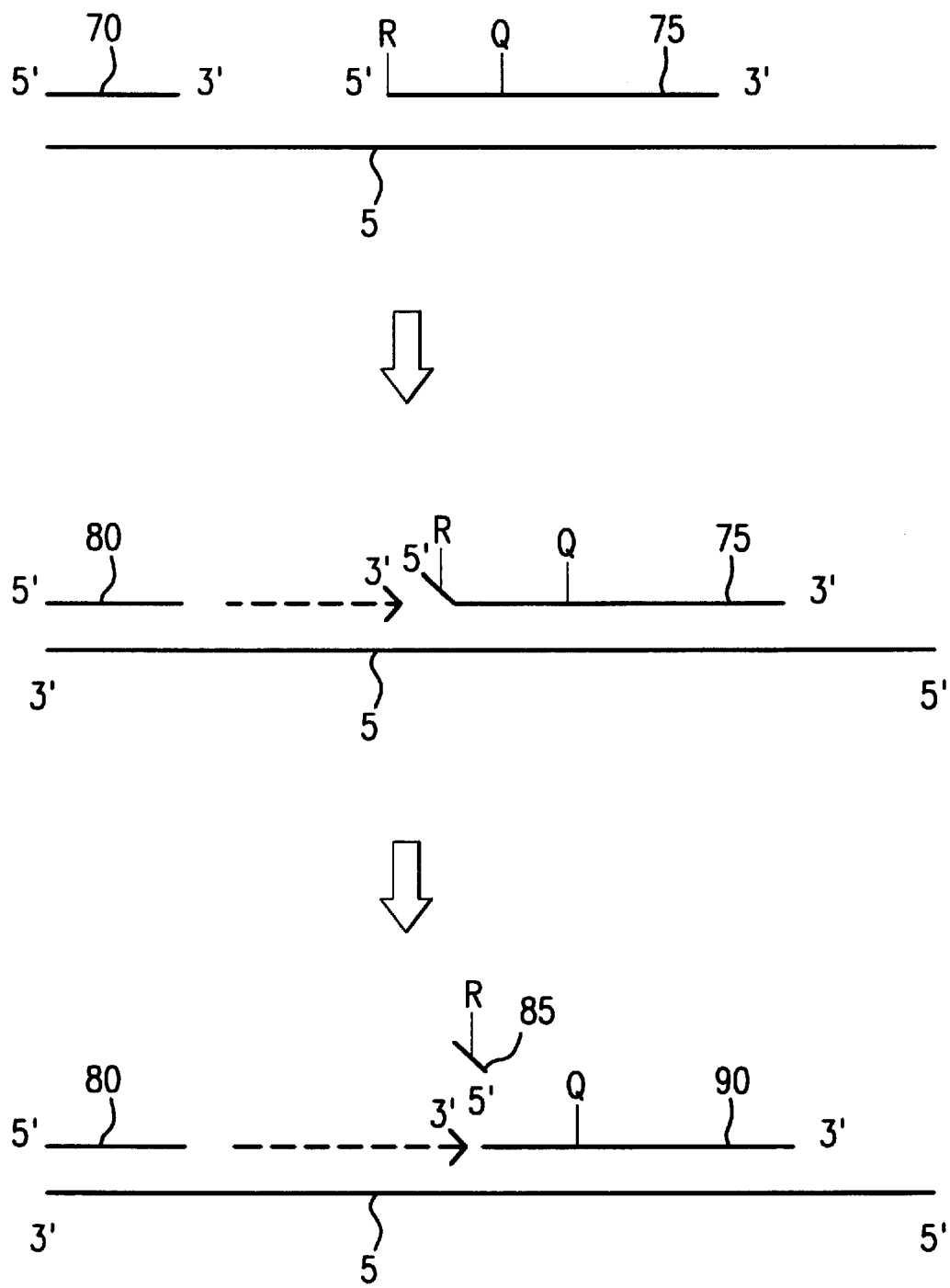

In a fifth assay format, referred to herein as the "Taqman" assay and illustrated in FIG. 5E, a doubly labeled probe including both a reporter label and a quencher label is digested upon hybridization to a target nucleic acid, thereby liberating one or both of the labels from the probe (Lee et al., 1993, Nucleic Acids Research 21:3761–3766; Holland et al. (1991) *Proc. Natl. Acad Sci. USA,* 88:7276–7280; Livak, U.S. Pat. No. 5,538,848). In this method, the doubly labeled probe 75 is hybridized to a target nucleic acid 5. In addition, an oligonucleotide primer 70 is hybridized to the target nucleic acid at a position upstream from the probe, i.e., in the 5' direction relative to the probe and closer to the 3'-end of the target nucleic acid. The primer 70 is then extended using a polymerase enzyme, e.g., a DNA polymerase, thereby forming an extended primer 80. During the primer extension reaction, the 5'→3' exonuclease activity of the polymerase serves to digest the probe 75 so as to form a first probe fragment 85 including the reporter label and a second probe fragment 90 including the quencher label. Thus, the reporter and quencher labels are separated, and energy transfer between the two is prevented. In this format, the emission of the reporter becomes unquenched upon hybridization of the primer oligonucleotide to the target nucleic acid and subsequent primer elongation, which results in digestion of the doubly labeled probe that is hybridized to the target nucleic acid 3' of the oligonucleotide primer.

Note that in each of the five assay formats discussed above and depicted in FIGS. 5A–E, unless otherwise specified, the location of the reporter and quencher is arbitrary. That is, while the reporter may be depicted on one probe and the quencher on another probe, their positions may be reversed.

While the assay formats described above are represented in terms of systems employing only a single reporter label, multi-reporter systems may also be practiced. Such multi-reporter systems are advantageous in applications requiring the analysis of multiple hybridization events in a single reaction volume. In such systems, each of the reporter molecules produces an emission that is spectrally resolvable among the emissions of the other reporters. The particular quencher used with each reporter can be the same or different, depending on the spectral properties of the quencher and reporter.

Each of the assays described above may be conducted in combination with a nucleic acid amplification step, e.g., PCR. That is, prior to conducting the hybridization assay, all or part of the nucleic acid sample may be amplified. When performed in combination with an amplification step, the hybridization assay may be conducted in an end-point mode or a real-time mode. In an end-point mode, the hybridization assay is performed after the amplification reaction is complete, e.g., after all or substantially all of the amplification cycles of a PCR reaction have been completed. In a real-time mode, a hybridization assay is performed multiple times during the amplification reaction, e.g., after each thermocycle of a PCR process (Higuchi, European Patent Publication No. EP 512 334). The real-time mode is preferred when a quantitative measure of the initial amount of target nucleic acid is required, e.g., where the copy-number of pathogen nucleic acid present in a blood sample.

EXAMPLES

The invention will be further clarified by a consideration of the following examples, which are intended to be purely exemplary of the invention and not to in any way limit its scope.

Example 1
Syntheses of Nitrothiazole Blue 5 and Nitrothiazole Orange 9

Figure 3A:
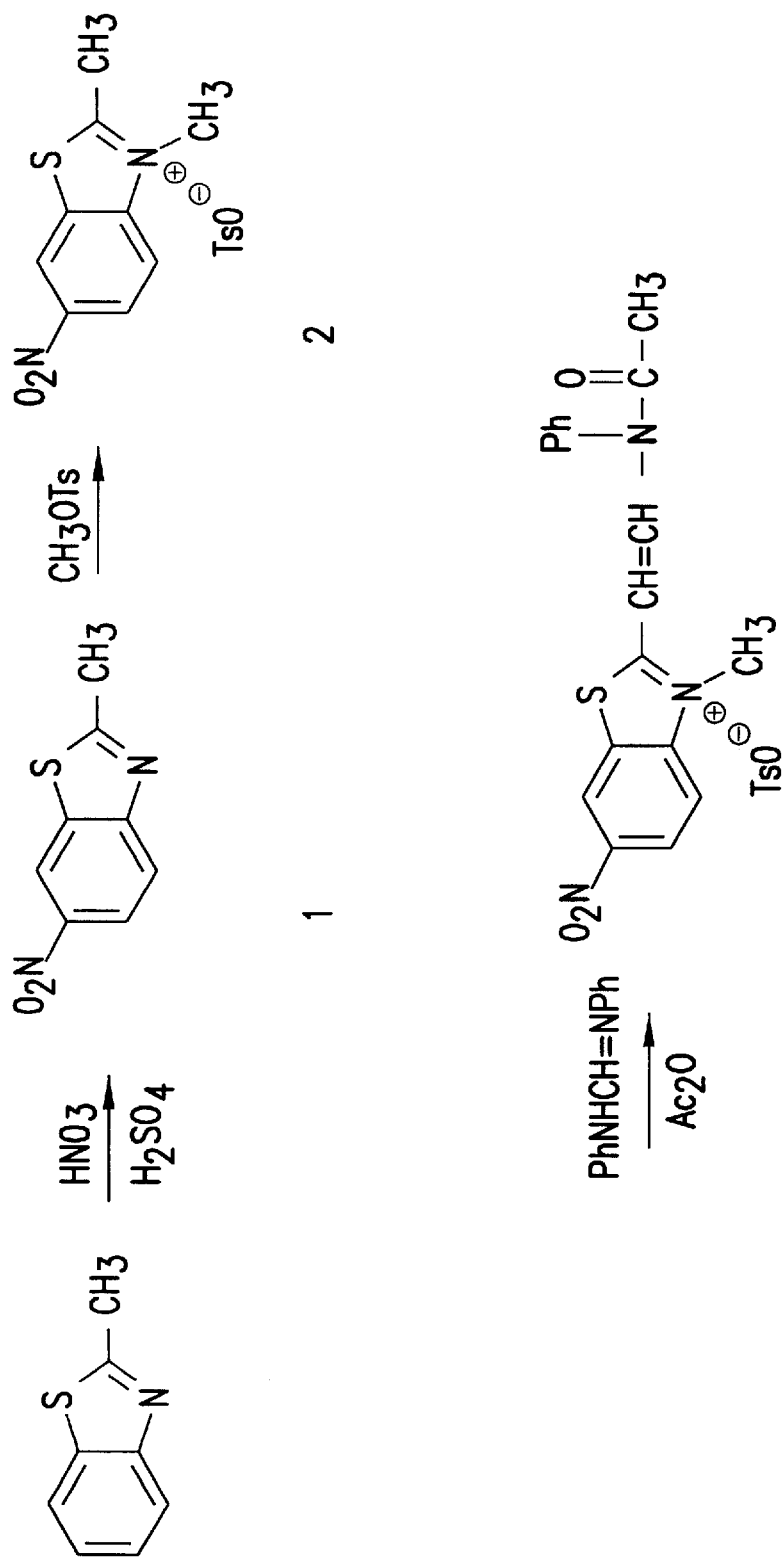
FIGS. 3A–3C show a synthetic scheme for the synthesis a first preferred cyanine dye quencher of the present invention.
Figure 3B:
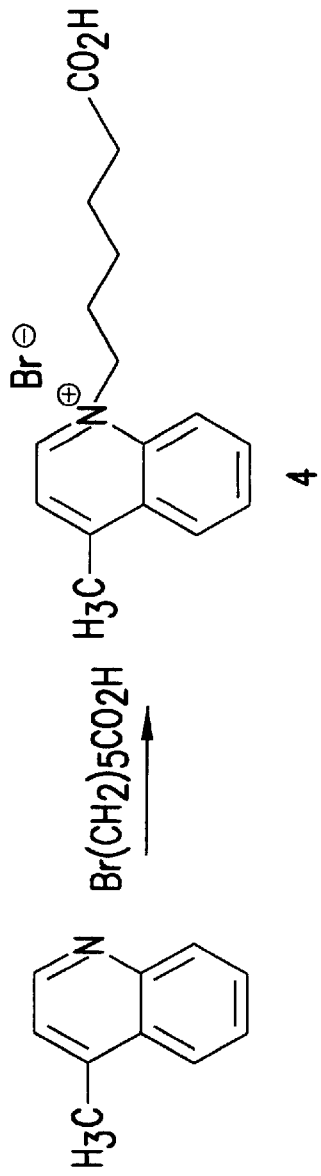
Figure 3C:
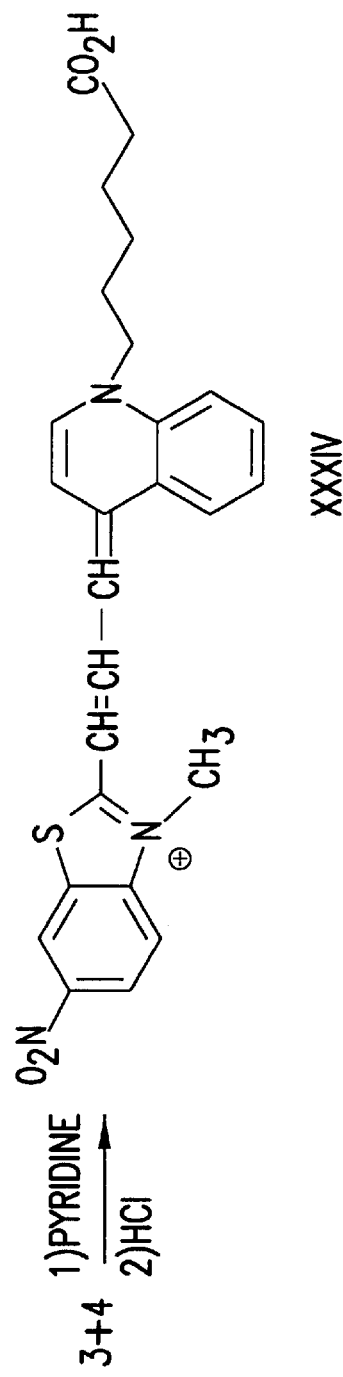
Figure 4A:
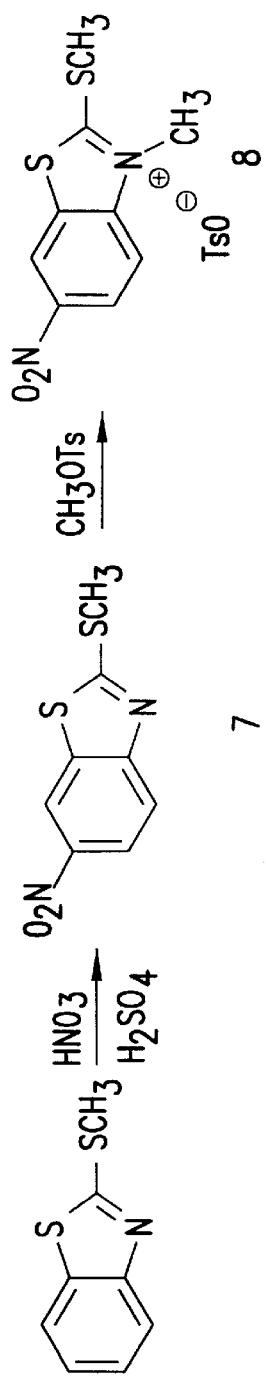
FIGS. 4A–4B show a synthetic scheme for the synthesis a second preferred cyanine dye quencher of the present invention.
Figure 4B:
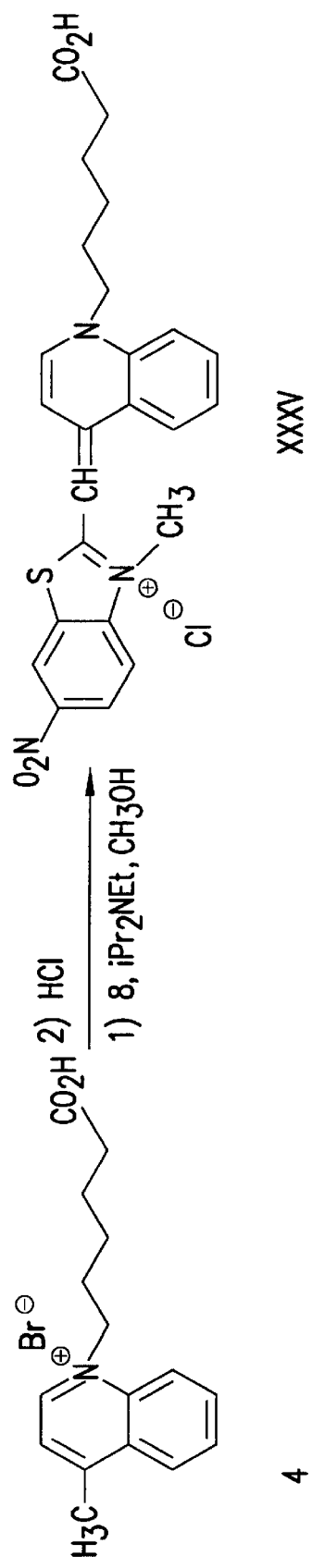

The syntheses of nitrothiazole blue 5 and nitrothiazole orange 9 are outlined in FIGS. 3 and 4.

Preparation of 6-nitrobenzothiazole (1). See FIG. 3A

Nitration of 2-methylbenzothiazole was performed following the method of Mizuno (1952) *J. Pharm. Soc. Japan* 72:745. A mixture of fuming nitric acid (1.6 mL) and concentrated sulfuric acid (1.2 mL) was added to an ice-cooled solution of 2-methylbenzothiazole (2 g) in sulfuric acid (8 mL). The resulting solution was allowed to warm to room temperature for one hour, then poured onto 100 mL of ice. The resulting solid was filtered, washed with water, and recrystallized from ethanol (80 mL) to provide 2.5 g of 6-nitrobenzothiazole (1) in the form of yellowish needles.

Preparation of 3-methyl-6-nitrobenzothiazolium p-toluenesulfonate (2). See FIG. 3A A mixture of 1 g of 6-nitrobenzothiazole (1) and 1.2 g of methyl-p-toluenesulfonate was heated to 140° C. for 20 min.

The mixture was allowed to cool to room temperature, and the resulting solid was washed with acetone and filtered to provide 1.1 g of 2, as a bluish solid.

Preparation of 2-(2'-acetanilidovinyl)-3-methylbenzothiazolium p-toluenesulfonate (3). See FIG. 3A A mixture of 200 mg (0.52 mmol) 3-methyl-6-nitrobenzothiazolium p-toluenesulfonate (2), 160 mg (0.8 mmol) diphenylformamidine and 2 ml acetic anhydride was refluxed for 20 min. The cooled solution was triturated with ether to provide 3, as a dark brown solid (200 mg).

Preparation of 1-(5'-carboxypentyl)-lepidinium bromide (4). See FIG. 3B

A mixture of 5 g lepidine and 10 g 6-bromohexanoic acid was heated to 130° C. for 6 h. The mixture was allowed to cool to room temperature, and the resulting solid was washed with acetone and filtered to provide 10.5 g of 4, as an off-white solid.

Preparation of nitrothiazole blue (XXXIV). See FIG. 3C

A mixture of 65 mg (0.13 mmol) acetanilide 3, 66 mg (0.2 mmol) of lepidinium bromide 4 and 1 ml pyridine was combined and refluxed for 30 min. The resulting blue solution was allowed to cool to room temperature, concentrated to dryness, and washed with 5×1 ml 5% HCl. The resulting residue was dried to provide 67 mg of 5 as a blue solid.

Preparation of nitrothiazole blue succinimidyl ester

To a solution of 31 mg (0.056 mol) nitrothiazole blue (XXXIV) in 0.5 ml dimethylformamide and 0.05 ml diisopropylethylamine was added 34 mg (0.12 mmol) O-(N-succinimidyl)N,N,N',N'-tetramethyluronium tetrafluoroborate. The mixture was warmed to 70° C. for 10 min. Reaction progress was monitored by TLC on silica gel using 600:60:16 dichloromethane:methanol:acetic acid as the eluant. To the homogeneous solution was added 2 ml of 5% HCl. The result precipitate was washed with additional HCl and dried to provide 30 mg of nitrothiazole blue succinimidyl ester as a dark solid.

Preparation of 2-(methylthio)-6-nitrobenzothiazole (7). See FIG. 4A 1.93 g of fuming nitric acid was added dropwise to a solution of 5 g of 2-(methylthio)benzothiazole in 16.8 g concentrated sulfuric acid cooled in an ice bath. After stirring at 5° C. for 3 h, the solution was poured onto ice and filtered to provide 5.7 g (25 mmol, 91%) 7 as a yellow solid.

Preparation of 3-methyl-2-(methylthio)-benzothiazolium p-toluenesulfonate (8)

A mixture of 0.5 g (2.2 mmol) of 6-nitro-2-(methylthio) benzothiazole (7) and 3.7 g (20 mmol) methyl-p-toluensulfonate was heated from 120° C. to 145° C. over one hour. The solution was allowed to cool, and to it was added 30 ml of ether. The resulting amorphous solid was triturated with acetone to provide 0.57 g (1.4 mmol, 63%) of 8 as a pale, mauve solid.

Preparation of nitrothiazole orange (XXXV). See
FIG. 4B

To a solution of 50 mg (0.12 mmol) of 3-methyl-2-(methylthio)-benzothiolium p-toluenesulfonate (8) and 41 mg (0.12 mmol) of 1-(5'-carboxypentyl)-lepidinium bromide (4) in 5 ml methanol was added 0.2 ml diisopropylethylamine. The resulting solution was refluxed for 15 min. The solvent was evaporated, and the reaction residue was triturated with 2 ml of 5% HCl. The resulting solid was washed with additional 5% HCl and dried to provide 8 mg of 9 as an orange solid.

Preparation of nitrothiazole orange succinimidyl ester

To a solution of 8 mg nitrothiazole orange (XXXV) in 0.1 ml dimethylformamide and 0.01 ml diisopropylethylamine was added 10 mg O-(N-succinimidyl)-N,N,N',N'-tetramethyluronlum tetrafluoroborate. The reaction mixture was warmed to 70° C. for 10 minutes, and its progress was monitored by TLC on silica gel using 600:60:16 dichloromethane:methanol:acetic acid as the eluant. To the resulting homogeneous solution was added 1 ml of 5% HCl. The precipitate was washed with additional HCl and dried to provide 8 mg of nitrothiazole orange succinimidyl ester as an orange solid.

Example 2
Preparation of Doubly-Labeled Probe for Taqman Assay

Automated synthesis of oligonucleotide probes was performed using an Applied Biosystems Model 394 DNA/RNA synthesizer (The Perkin-Elmer Corporation, PE Applied Biosystems Division (ABD)) according to the general procedures described in the operator's manual. The oligonucleotides were synthesized in 0.2 $\mu$mol scale using dye-labeled CPG solid supports (Mullah & Andrus (1997) *Tetrahedron Letters*, 38(33):5751–5754), DNA FastPhosphoramidites (User Bulletin number 85, 1994, ABD), and FAM- and TET-labeled phosphoramidites (User Bulletin number 78, 1994, ABD). The standard 0.2 $\mu$mol synthesis cycle was slightly modified by extending the coupling time of FAM-labeled phosphoramidites by an additional 120 sec (User Bulletin number 78, 1994, ABD). Each probe included a reporter dye attached to the 5'-end, and a quencher dye located at the 3'-end.

After completion of the synthesis, oligonucleotides were autocleaved from the support of the DNA synthesizer by treating with a mixture of MeOH:t-BuNH$_2$:H$_2$O (1:1:2) (Woo et al., U.S. Pat. No. 5,231,191) using a 1 hr autocleavage procedure ("END CE" procedure) as described in the operator's manual for the Applied Biosystems Model 394 DNA/RNA synthesizer. Base protecting groups were removed by heating the mixture at 85° C. for 1 hr or at 65° C. for 3 h in the mixture of MeOH:t-BuNH$_2$:H$_2$O.

The crude oligonucleotides thus obtained were analyzed for purity and integrity using reverse phase high performance liquid chromatography ("HPLC") using the following equipment and conditions: Perkin Elmer Series 200 solvent delivery system equipped with ABI 783A programable detector; Perkin Elmer ISS200 autosampler; and PE Nelson 900 series data system; RP-18 reverse phase chromatography column (220×4.6 mm, ABD); solvent A: 0.1 M triethyammonium acetate; solvent B: CH$_3$CN; gradient 4–28% B in 35 min; flow rate: 1 ml/min; and detector wavelength: 260 nm.

Example 3
Taqman Assay for Human Beta Actin Gene

Human genomic DNA was prepared using conventional methods. The composition of the assay reagent was as follows (50 $\mu$l total volume):

| Component | Conc. | Volume ($\mu$l) |
|---|---|---|
| dNTPs (dATP, dCTP, dGTP, dUTP) | 10 mM ea | 4 |
| MgCl2 | 25 mM | 7 |
| [a]PCR Buffer, 10X | — | 5 |
| Uracil N-glycosylase (UNG) | 1 unit/ml | 0.5 |
| Forward PCR Primer | 3 $\mu$M | 5 |
| Reverse PCR Primer | 3 $\mu$M | 5 |
| AmpliTaq ™ Gold DNA Polymerase | 5 units/ml | 0.25 |
| Human Male DNA | 10 ng/ml | 2 |
| Taqman probe | 2 $\mu$M | 5 |
| Water | — | 16.3 |

[a]10 mM KCl, 100 mM TRIS-HCl, 0.1 M EDTA, 600 nm passive internal standard, pH 8.3.

The Taqman probe was synthesized with the reporter dye near the 5' end and the quencher molecule at the 3' end such that energy transfer and consequent quenching occurs when the probe is intact.

The assay reagents were combined in a 96-well microtiter tray and thermally cycled using the following protocol: 50° C. for 2 min; 95° C. for 10 min; 40 cycles of 95° C. for 15 sec followed by 60° C. for 1 min. Fluorescence was monitored during the amplification process using a Applied Biosystems Model 7700 Sequence Detection System (ABD).

The results of a Taqman experiment can be analyzed using two parameters: the Rn value and the Ct value. The Rn value is the ratio of the fluorescence of a reporter dye and the fluorescence of a passive reference at the end of a PCR experiment. The Ct value, also known as the threshold cycle number, is the PCR cycle number at which the fluorescence ratio, Rn, is distinguishable from the background. For a given reporter dye and a fixed concentration of target, both the Rn and Ct values reflect the efficiency of the quencher.

The efficiency of nitrothiazole blue (NTB) (5) was compared to that of TMR in quenching the reporters FAM and TET. The Rn and Ct values for NTB and TMR were indistinguishable for both reporter dyes. The quencher nitrothiazole orange (NTO) (9) was used to quench FAM fluorescence and was found to have equivalent quenching efficiency to both NTB and TMR. NTB was paired with the reporter, NED, to provide results that were similar to NTB quenching of fluorescence of other reporters. TMR could not be used as a quencher with the reporter dye NED because the fluorescence emissions of TMR and NED are at the same wavelength. This example shows that the quenching efficiency of non-fluorescent cyanine dyes is equivalent to the quenching efficiencies of traditionally used quenchers, such as TMR.

Example 4
Seven-Color, Homogeneous Detection of Six PCR Products

This example provides an extension of the fluorogenic PCR 5'-nuclease assay, or "Taqman" assay. Sequence-specific probes consisted of a novel non-fluorescent quencher, nitrothiazole blue (NTB), at the 3'-terminus, and six different reporter-dyes at the 5'-terminus. The six reporters were 6-FAM, dR110, dR6G, dTMR, DROX, and JAZ dyes. The seventh color was from aluminum phthalocyanine tetrasulfonate and was utilized as a "passive reference" to calibrate concentration variations. Our test system was a set of three single-nucleotide polymorphisms (SNPs). Each SNP system consisted of two primers and two sequence-specific probes, each labeled with a different reporter dye and NTB. Following PCR, the reactions were diluted with water and measured in a microcuvette on a luminescence spectrometer in synchronous scanning mode. In this method, both the excitation and emission wavelengths were scanned, with a fixed wavelength difference (A) between excitation and emission wavelengths. The spectral overlap in the set was evaluated by calculation of the condition number of the 7×7 matrix (dye fluorescence vs. wavelength). The small value of the condition number (1.5) proved that the crosstalk between the dyes was minimal. SNP analyses of known, synthetic target sequences and genomic DNA were plotted both as normalized, subtracted spectra and as data points in three separate dot plots.

Materials And Methods

Dye: Aluminum phthalocyanine tetrasulfonate was obtained from Porphyrin Products (Logan, Utah) and was utilized as a passive reference (Livak, K. J. and L. J. McBride. 1998. Passive Internal References for the Detection of Nucleic Acid Amplification Products. U.S. Pat. No. 5,736,333.). Reporter dyes were all obtained from PE Applied Biosystems. The four d-rhodamine dyes have been previously described as dyes for DNA sequencing (Lee, L. G., S. L. Spurgeon, C. R. Heiner, S. C. Benson, B. B. Rosenblum, S. M. Menchen, R. J. Graham, A. Constantinescu, K. G. Upadhya and J. M. Cassel. 1997. New Energy Transfer Dyes for DNA Sequencing. Nucleic Acids Res. 25: 2816–2822.). JAZ is a pentafluorophenyl-derivative of MR200-1 (14). Nitrothiazole blue (NTB) was prepared by the general method of Brooker, et al.(Brooker, L. G. S., G. H. Keyes and W. W. Williams. 1942. Color and Constitution. V. The Absorption of Unsymmetrical Cyanines. Resonance as a Basis for a Classification of Dyes. J. Am. Chem. Soc. 64: 199–210). The dye-carboxylic acids were converted to the succinimidyl esters via standard peptide chemistry.

Deoxyoligonucleotide synthesis: Primers were synthesized by standard phosphoramidite chemistry (ABI 394 DNA/RNA synthesizer). Probes with nitrothiazole blue (NTB) at the 3' terminus and reporter dyes at the 5' terminus were prepared by synthesis of the NTB-labeled support using a trifunctional linker (Mullah, B., K. Livak, A. Andrus and P. Kenney. 1998. Efficient Synthesis of Double Dye-Labeled Oliogonucleotide Probes and Their Application in a Real Time PCR Assay. Nucleic Acids Res. 26: 1026–1031), followed by standard phosphoramidite nucleotide coupling. After synthesis of the oligodeoxynucleotide sequence with a terminal MMT-protected aminohexylphosphoramidite, the MMT group was removed under standard acidic conditions (3% trichloroacetic acid in dichloromethane for 5 min) and a solution of 10–20 mg dye-succinimidyl ester in 5:1 DMF/acetonitrile (0.75 mL) and diisopropylethylamine (0.025 mL) was delivered to the support-bound oligonucleotide on the synthesizer. The coupling time for the dye reaction was 20 min. Deprotection and cleavage were accomplished by incubating the resin with 1:1:2 t-butylamine: methanol: water for 2 h at 65° C. (Woo, S. L., S. M. Menchen and S. Fung. 1993. Rhodamine Phosphoramidite Compounds. U.S. Pat. No. 5,231,191). Purification was accomplished by HPLC (Perkin Elmer Aquapore RP300, 220×4.6 mm C8 column, eluted with 0.1 M TEAA vs. acetonitrile) on a Waters HPLC equipped with a diode array detector. The NTB dye is not completely stable to the deprotection and cleavage conditions and yields of purified oligo were typically 50–70% of yields obtained when probes were synthesized with support-bound tetramethylrhodamine (a fluorescent quencher).

SNP primer sequences:
MPO-F: 5'-AAATCTTGGGCTGGTAGTGCTAAA (SEQ ID NO.: 1)
MPO-R: 5'-GGCCAGGCTGGTCTTGAAC (SEQ ID NO.: 2)
BAK-F: 5'-TGGGCCTGACCACTCCTTT (SEQ ID NO.: 3)
BAK-R: 5'-TGCGATCCCGCTTGTGAT (SEQ ID NO.: 4)
LIG-F: 5'-AGAGGAGACCCCGAAAGAAAG (SEQ ID NO.: 5)
LIG-R: 5'-GGCTGGTCCCCGTCTTCT (SEQ ID NO.: 6)
Probe sequences:
MPO/A:5'-dR6G-TGATCCACC TGCCTCAGCCTC-NTB-3' (SEQ ID NO.: 7)
MPO/G:5'-dR110-TGATCCACC CGCCTCAGCCT-NTB-3' (SEQ ID NO.: 8)
BAK/T:5'-dTMR-CTGCCCATCCCCAGCCCCT-NTB-3' (SEQ ID NO.: 9)
BAK/G:5'-dROX-CTGCCCAGCCCCAGCCC-NTB-3' (SEQ ID NO.: 10)
LIG/A:5'-6FAM-CCTTCTCTGT TGCCACTTCAGCCTCT-NTB-3' (SEQ ID NO.: 11)
LIG/C:5'-JAZ-CCTTCTCTGT GGCCACTTCAGCCT-NTB-3' (SEQ ID NO.: 12)

Synthetic targets: Synthetic targets containing priming sites and both possible alleles were constructed by synthesizing the forward and reverse 5'-ends of the target with a 10 bp complementary region at the 3' terminus. The oligodeoxynucleotides were combined and the ends filled in with Klenow DNA polymerase and 4 dNTPs (Maniatis, T., E. F. Fritsch, and J. Sambrook, J. 1982. Molecular Cloning. Cold Spring Harbor Laboratory, Cold Spring Harbor, N.Y.). The MPO and LIG target utilized one common forward primer for both alleles (the prefixes "F" and "R" describe forward and reverse primers, respectively), and the BAK target utilized a separate pair of primers for each allele.

Synthetic target oligonucleotides:
MPO:
F463: 5'-AGAAATCTTGGGCTGGTAGTGCTAAATT CAAAGGCTGGGGACAGGCTGGGGC-CAGTGGCTCATGCCTGTAATCCC (SEQ D NO.: 13)
R463G: 5'-TTGGCCAGGCTGGTCTTGAACTCCTGA CCTCAAGTGATCCACCCGCCTCAGCCTC-CCAAAGTGCTGGGATTACAG (SEQ ID NO.: 14)
R463A: 5'-TTGGCCAGGCTGGTCTTGAACTCCTGA CCTCAAGTGATCCACCTGCCTCAGCCTC-CCAAAGTGCTGGGATTACAG (SEQ ID NO.: 15)
BAK:
F2622T: 5'-CCTGGGCCTGACCACTCCTTTGCCCCC CCAGGTGGACTGGGGGCTGCCCATCCCC (SEQ D NO.: 16)
R2622T: 5'-TCTGCGATCCCGCTTGTGATGGGCCGGGT GAATGGGGGAGGGGCTGGGGATGGGC (SEQ ID NO.: 17)

F2622G:
  5'-CCTGGGCCTGACCACTCCTTTGCCCCCC
  AGGTGGACTGGGGGCTGCCCAGCCCC (SEQ ID
  NO.: 18)
R2622G:
  5'-TCTGCGATCCCGCTTGTGATGGGCCGGGT
  GAATGGGGGAGGGGCTGGGGCTGGGC (SEQ ID
  NO.: 19)
LIG:
Fex6:5'-
  GAAGAGGAGACCCCGAAAGAAAGCCTCA-
  CAGAGGCTGAAGTGGC (SEQ ID NO.: 20)
Rex6A:5'-
  TGGGCTGGTCCCCGTCTTCTCCTTCCT-
  TCTCTGTTGCCACTTCAG (SEQ ID NO.: 21)
Rex6C:5'-
  TGGGCTGGTCCCCGTCTTCTCCTTCCT-
  TCTCTGTGGCCACTTCAG (SEQ ID NO.: 22)

Genomic targets: Genomic DNA was obtained from human blood samples and from cell culture ("Raji" cell line, ATCC Number: CCL-86 Organism: Homo sapiens (human) C, was obtained from American Type Cell Collection, Rockville, Md.)

PCR reactions: PCR reactions (25 µL) were carried out on a ABI PRISM 7700 Sequence Detector. (The 7700 instrument with its single line excitation source could be used to detect 6FAM, dR110 and dR6G but not dRM, DROX, JAZ or AlPcTS. In this experiment it was used for the thermal cycler component.) Each reaction contained Tris buffer, pH 8 (0.1 M), $MgCl_2$ (10 mM), dATP (0.4 mM), dCTP (0.4 mM), deaza dGTP (0.4 mM), dUTP (0.8 mM), AmpliTaq Gold®(2.5 U), AmpErase® uracil N-glycosylase (0.5 U), aluminum phthalocyanine tetrasulfonate (AlPcTS) passive reference (1500 nM), glycerol (16%), gelatin (0.1%), Tween 20 (0.02%), six primers (each at 0.3 µM), and six probes (each at 0.25 µM). Reactions with target contained either synthetic target (1,000–10,000 copies) or genomic DNA (20 ng). The thermal cycle was 2 min at 50° C., 10 min at 95° C., and 40 cycles of 15 s at 95° C. and 1 min at 60° C. When the reaction was complete 30 µL of water was added to each reaction, the solution transferred to a microcuvette and the fluorescence measured by synchronous scanning.

Multicolor analysis: Synchronous scanning spectra of the pure dyes (six reporters and one internal standard) and each of the multiplex PCR reactions were measured on a Perkin-Elmer LS50-B luminescence spectrometer. The instrument was set to synchronous scan mode with both excitation and emission slits at 10 nm and a fixed excitation and emission difference of 20 nm ($\Delta\lambda$=20 nm). Samples were measured in a 45 µL quartz microcuvette with a pathlength of 0.3 cm. Each of the seven pure dye spectra had a wavelength that exhibited a maximum signal (at excitation wavelengths of 497, 519, 547, 574, 601, 622 and 665 nm). A pure-spectra matrix was generated by recording the signal at each of these wavelengths for each of the pure spectra. The signal for one sample at each of these wavelengths was normalized to the internal standard signal (at 665 nm) then recorded as a column vector. When left multiplied by the inverse of the pure dye spectra matrix the resulting column vector was taken as the coordinates for one point on each of the three scatter plots (Pettofrezzo, A. J. 1978. Matrices and Transformations. Dover, Englewood Cliffs, N.J.). Calculations were performed using an application in LabVIEW (National Instruments, Austin Tex.).

Results and Discussion

Methods of analysis relying on homogeneous detection of multicolor fluorescent dyes and energy transfer must meet several criteria to be successful. The fluorescent dyes must be bright and spectrally well-resolved, and the energy-transfer must be efficient across the array of dyes. Two modes of fluorescent detection for multi-dye systems are commonly used: emission scanning with a fixed excitation wavelength and synchronous scanning in which both excitation and emission wavelengths are scanned simultaneously. The use of emission scanning allows very low amounts of analyte to be detected when the fixed excitation wavelength originates from a laser source, as in automated DNA sequencing instruments. Synchronous scanning, or use of multiple excitation wavelengths, allows efficient detection of multiple dyes with widely spaced excitation maxima and is especially useful in systems that do not require detection of low analyte concentrations.

Figure 6A:
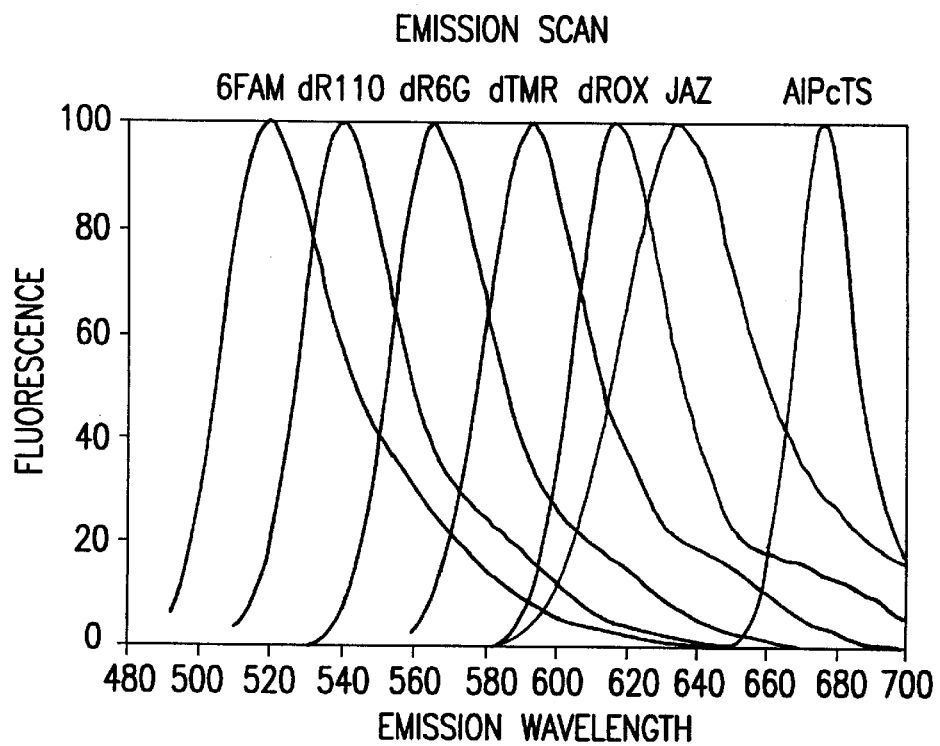
FIG. 6. depicts normalized fluorescence spectra of the six reporter dyes (6FAM, dR110, dR6G, dTMR, dROX, JAZ) and the passive reference (AlPcTS) in tris-EDTA (TE) buffer. a) Emission scans; b) Synchronous scans.
Figure 6B:
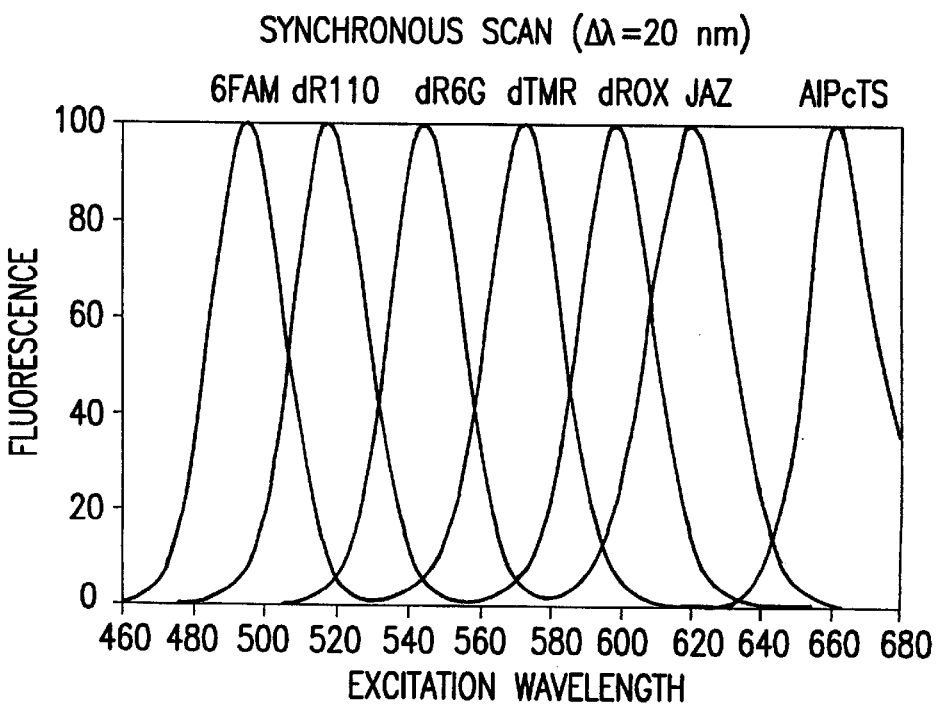

We chose a set of six reporter dyes and one passive reference that are spectrally well-resolved in fluorescence emission mode, in which the excitation wavelength is held constant and the emission wavelengths are scanned. These dyes would not perform well as a set with a single excitation wavelength since the excitation maxima of the set varies from 500 to 670 nm. To obtain equivalent brightness across the set of dyes, the dyes were measured in synchronous scanning mode in which both the excitation and emission wavelengths were scanned with a fixed wavelength difference of 20 nm. In this mode the dyes were both better resolved and were each equivalently excited. The emission and synchronous scans of the seven dyes, normalized to the peak maxima, are shown in FIG. 6.

In order to calculate concentrations of analytes in a multi-dye system, pure dye spectra are measured and a matrix is generated from the normalized spectra. The fluorescence of each dye at the wavelength of maximal signal for each of the dyes defines the matrix. The condition number is a convenient metric to compare matrices. The condition number can vary from one to infinity, where a condition number of one describes a set of dyes that are completely spectrally resolved: all off-diagonals are zero (Pettofrezzo, A. J. 1978. Matrices and Transformations. Dover, Englewood Cliffs, N.J.). For comparable systems, a smaller condition number produces data with less multicomponent noise (Kalivas, J. H. 1986. Determination of Optimal Parameters for Multicomponent Analysis Using the Calibration Matrix Condition Number. Anal. Chem. 58: 989–992). A comparison of the 7×7 matrices and condition numbers of the two types of scans shown in Table 1 illustrates that for this dye set the synchronous scan provides data with less multicomponent noise than the emission scan. Table 1. Comparison of the matrices and condition numbers of the normalized fluorescence spectra of the seven dyes measured as emission or synchronous scans. Fluorescence values were determined at the emission or synchronous scan maxima of each dye. (a) Emission discrimination only. The normalized emission spectra for each of the dyes listed in the top row for each of the discrete wavelengths listed in the left most column are tabulated. The condition number for this matrix is 4.05. (b) Synchronous scan discrimination only. The normalized synchronous scan response for the six dyes at the six excitation/emission respectively) settings is tabulated.

The condition number for this matrix is 1.46.

|  | 6FAM | dR110 | dR6G | dTMR | dROX | JAZ | AlPcTS |
|---|---|---|---|---|---|---|---|
| a) | | | | | | | |
| 519 | 1 | 0.21 | 0 | 0 | 0 | 0 | 0 |
| 540 | 0.56 | 1 | 0.085 | 0 | 0 | 0 | 0 |
| 567 | 0.25 | 0.37 | 1 | 0.12 | 0 | 0 | 0 |
| 595 | 0.08 | 0.16 | 0.34 | 1 | 0.14 | 0.06 | 0 |
| 618 | 0.03 | 0.05 | 0.17 | 0.39 | 1 | 0.56 | 0 |
| 637 | 0.01 | 0.02 | 0.08 | 0.18 | 0.52 | 1 | 0 |
| 679 | 0 | 0 | 0.01 | 0.03 | 0.11 | 0.23 | 1 |
| b) | | | | | | | |
| 497/517 | 1 | 0.10 | 0 | 0.01 | 0 | 0 | 0 |
| 519/539 | 0.09 | 1 | 0.04 | 0.01 | 0 | 0 | 0 |
| 547/567 | 0 | 0.05 | 1 | 0.07 | 0.01 | 0 | 0 |
| 575/595 | 0 | 0 | 0.04 | 1 | 0.06 | 0.01 | 0 |
| 601/621 | 0 | 0 | 0 | 0.06 | 1 | 0.21 | 0 |
| 622/642 | 0 | 0 | 0 | 0 | 0.14 | 1 | 0 |
| 665/685 | 0 | 0 | 0 | 0 | 0 | 0 | 1 |

Figure 7:
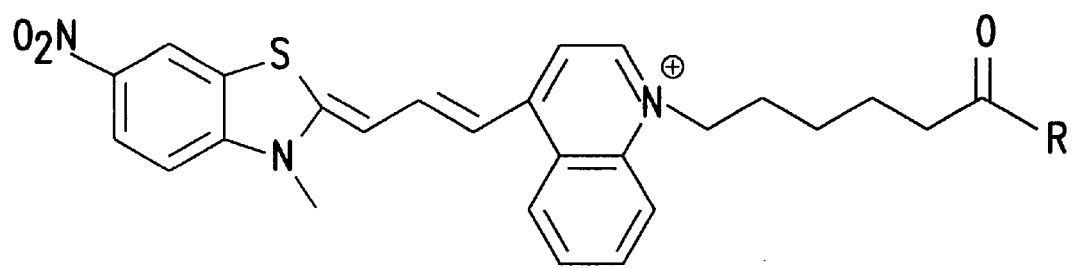
FIG. 7. shows the structure of an NTB quencher.
Figure 8A:
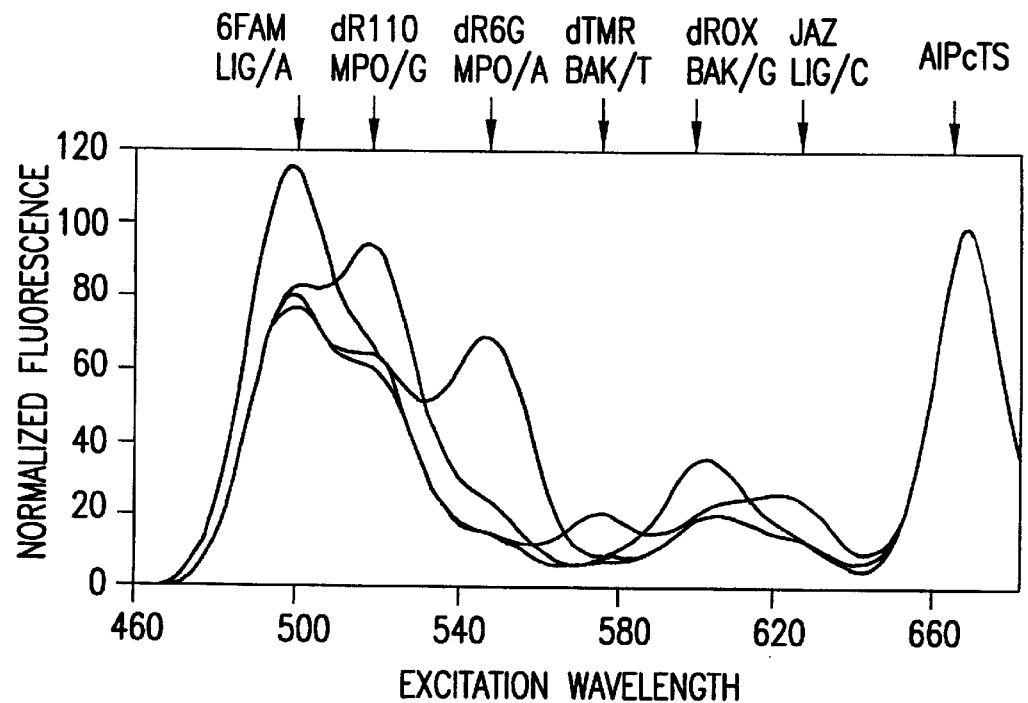
FIG. 8. is an overlay of seven synchronous scans of post-PCR reactions. Each reaction contained six probes and six primers. To each of six tubes was added one synthetic target. The seventh tube contained no target and was used as the no-target-control (NTC). a) Spectra normalized to AlPcTS; b) Spectra normalized to AlPcTS with NTC subtracted.

In order to utilize reporter dyes spanning the spectrum from 500 to 640 nm a nonfluorescent quencher, nitrothiazole blue (NTB) was developed. The structure of NTB is shown in FIG. 7. NTB has an absorbance maximum of 636 nm and an extinction coefficient of 60,000 $cm^{-1}$ $M^{-1}$. Several dye candidates were investigated, including DABSYL, nitrated xanthene dyes, and reactive azo dyes. NTB provided the most efficient quenching for the greatest range of reporter dyes. The quenching efficiency of NTB is illustrated in FIG. 8A where the ratio of post-PCR fluorescence to initial fluorescence in each PCR reaction ranged from 0.5 to 2.5-fold. This range is similar to the ratio using the standard TMR quencher with FAM reporter dye (Livak, K. J., S. J. A. Flood, J. Marmaro, W. Giusti, and K. Deetz. 1995. Oligonucleotides with Fluorescent Dyes at Opposite Ends Provide a Quenched Probe System Useful for Detecting PCR Product and Nucleic Acid Hybridization. PCR Methods Applicat. 4: 357–362).

We chose to use a set of three SNPs as our model system. Methods of analysis of SNPs have been recently reviewed (Landegren, U., M. Nilsson and P.-Y. Kwok. 1998. Reading Bits of Genetic Information: Methods for Single-Nucleotide Polymorphism Analysis. Genome Res. 8: 769–776). SNPs are an example of a simplified multiplex PCR target because genomic DNA provides equimolar target copes for the different SNP loci. Use of equimolar target copies avoids the problem of unequal target copies in the PCR reaction that can allow one PCR product in the multiplex to dominate the resources of the reaction mixture. We selected an SNP set with sufficient GC content to allow fairly short probes (17 to 26 bp). In general, shorter probes (<30 bp) with $T_m$ values of approximately 65° C. provide satisfactory discrimination between single nucleotide mismatches. We also chose to use a luminescence spectrometer as our detector for endpoint analysis, because it provided the flexibility to vary the reporter dyes and excitation and emission detection wavelengths. The luminescence spectrometer is not a convenient instrument for real-time detection, but can provide a model for end-point, multiplex systems. The synchronous scan system could be translated into a real-time instrument with a white light source and an excitation and an emission filter wheel (Taylor, T. B., E. S. Winn-Deen, E. Picozza, T. M. Woudenberg and M. Albin. 1997. Optimization of the Performance of the Polymerase Chain Reaction in Silicon-Based Microstructures. Nucleic Acids Res. 25: 3164–3168).

Figure 8B:
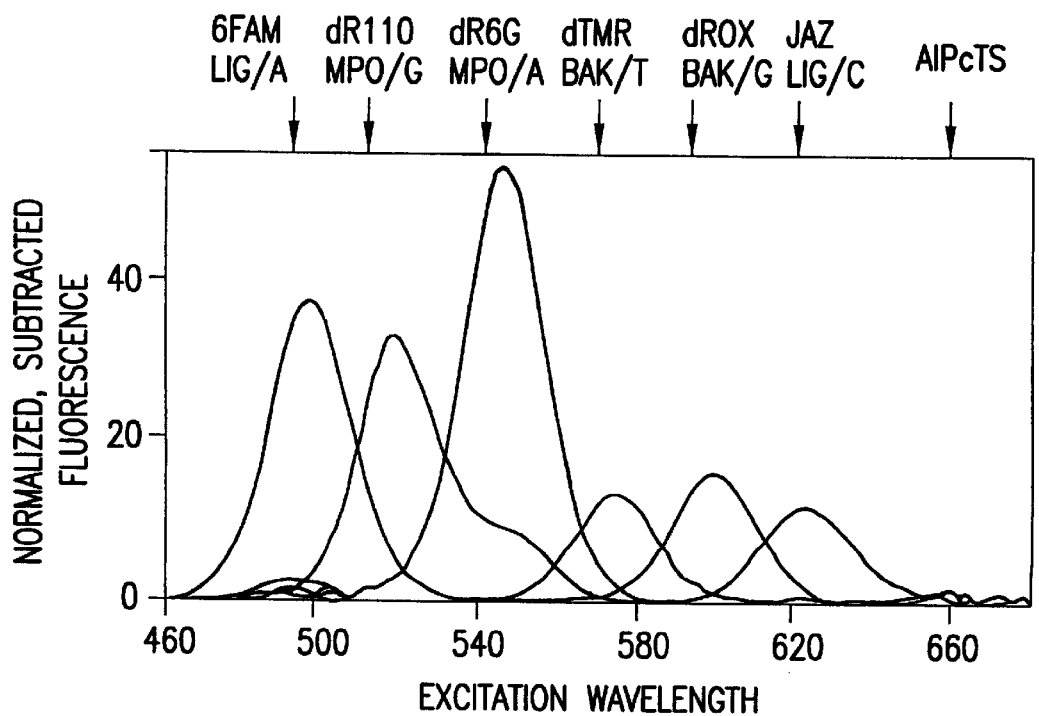
Figure 9A:
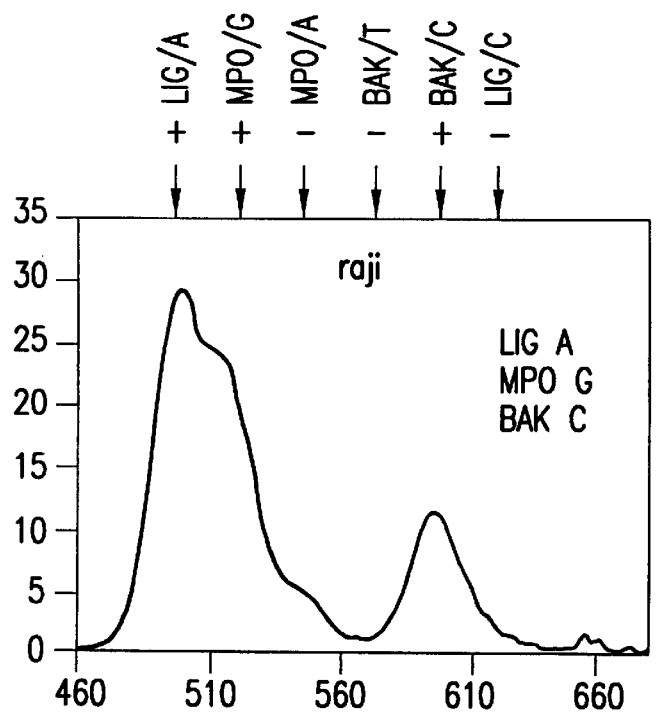
FIG. 9. shows synchronous scans of post-PCR reactions with genomic DNA. Each tube contained 6 probes and 6 primers. The spectra were normalized to AlPcTS and the NTC spectra were subtracted. Normalized, subtracted fluorescence is plotted on the y-axis and excitation wavelength on the x-axis.
Figure 9B:
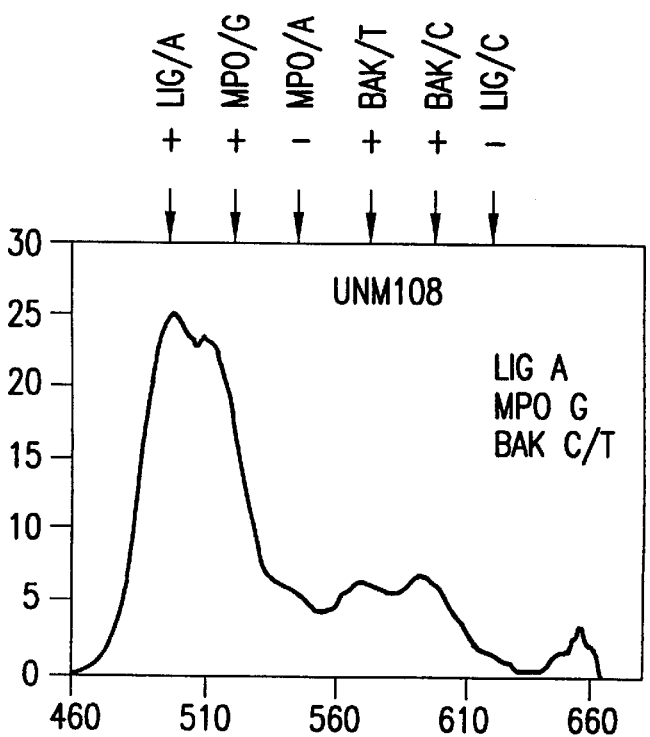
Figure 9C:
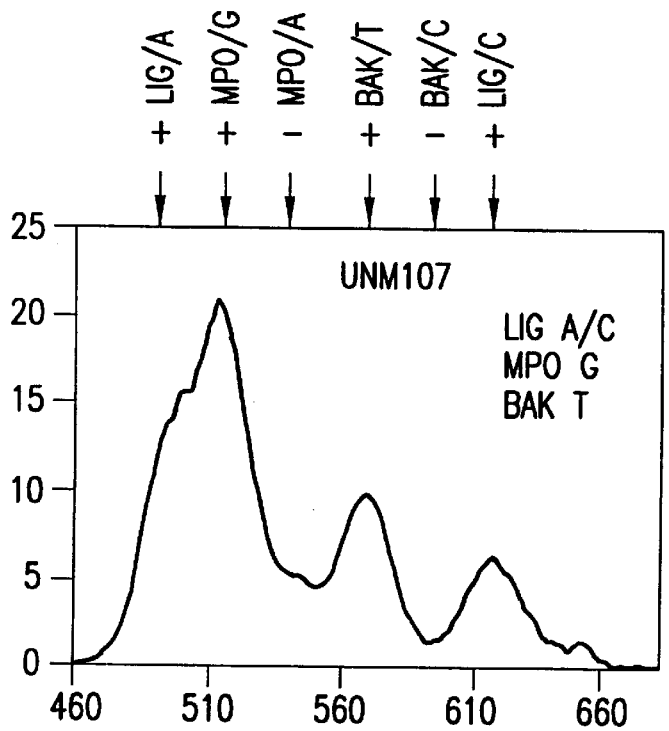
Figure 9D:
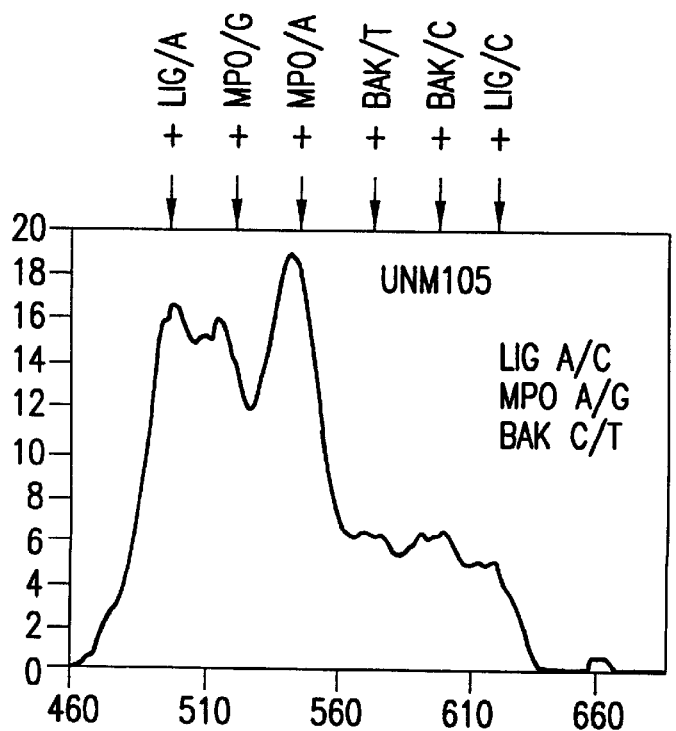
Figure 9E:
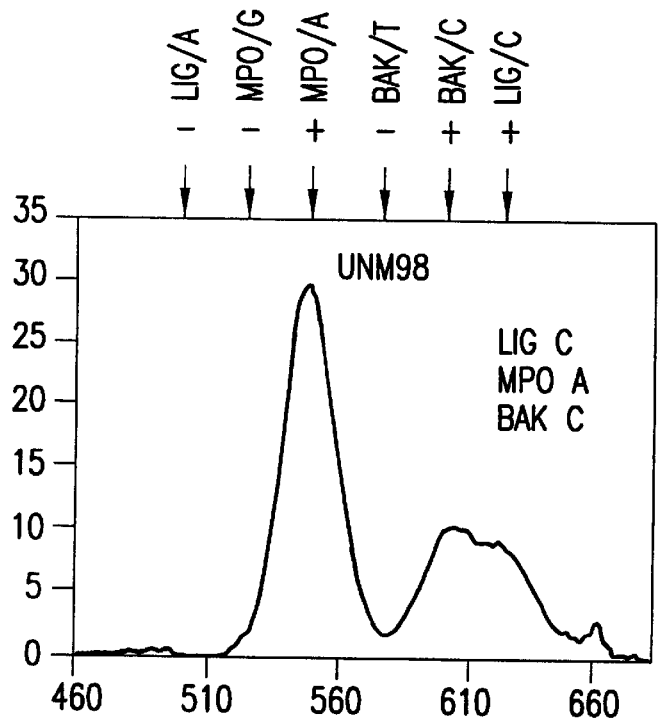
Figure 9F:
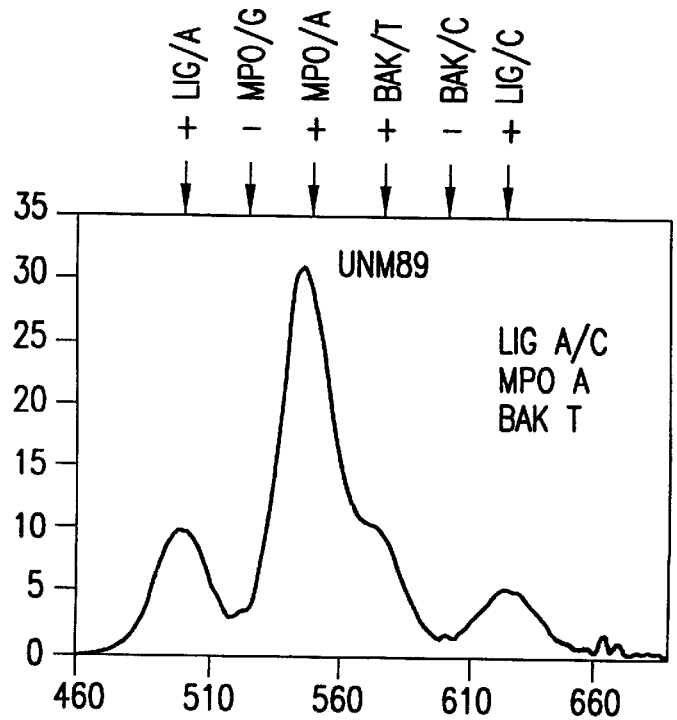
Figure 10A:
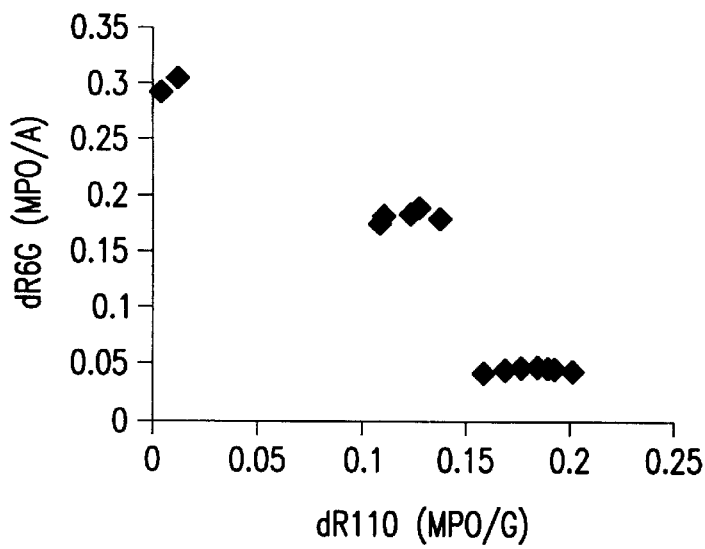
FIG. 10. shows three dot plots of 15 genomic DNA samples after normalization, subtraction of NTC spectra and multicomponent analysis.
Figure 10B:
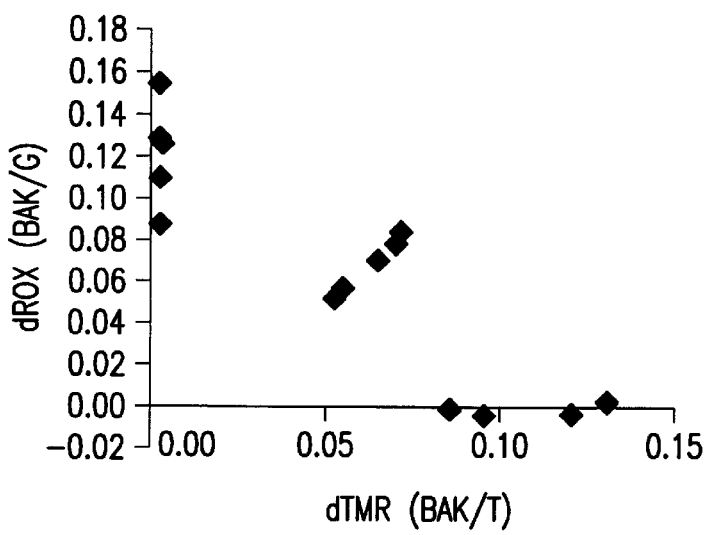
Figure 10C:
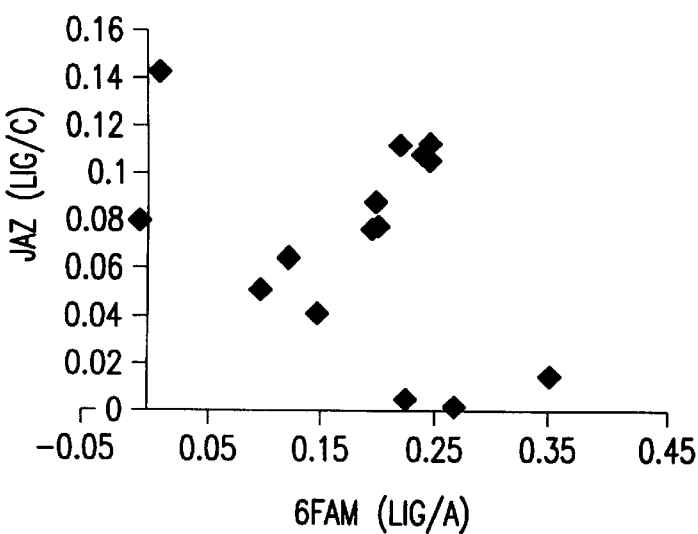

In our initial experiment we added one of each of the six synthetic targets, homo and heterozygous for each SNP loci, to each of six separate reaction mixtures containing all the primers and probes. The synchronous scans were normalized to the aluminum phthalocyanine tetrasulfonate (AlPcTS) peak and overlaid as shown in FIG. 8. Each reaction showed an increase in signal in the appropriate color. A small amount of non-specific cleavage of the dR110-MPO/G probe is apparent. Next, we used samples of genomic DNA in the multiplex reaction. The synchronous scans were normalized to the AlPcTS peak and the no-target-control spectrum was subtracted. The normalized, substracted synchronous scans of 6 examples are shown in FIG. 9. Each reaction provided a different "fingerprint" that can be correlated to the correct genotype. A more typical method of analysis are dot plots. Results from 15 different genomic samples after normalization, subtraction and multicomponent analysis are shown in FIG. 10. Each sample is displayed as a data point in all three plots. The 90° distribution of the homozygous samples illustrates the excellent spectral discrimination of the dyes. The heterozygous alleles are distinguable as a population with a 45° distribution.

Conclusions

A multiplex PCR system has the advantages of increased sample throughput and potential cost savings. Our example provides good results for a multiplex endpoint SNP analysis. The excellent spectral discrimination suggests that additional reporter dyes could be added at shorter wavelengths without loss in spectral resolution. The use of the spectrally well-resolved passive reference, aluminum phthalocyanine tetrasulfonate, was essential for signal normalization. Evaporation during thermal cycling results in a higher probe concentration that in turn results in an increase in fluorescence. The non-fluorescent quencher, NTB, is shown here to quench a good range of reporter dyes without implementing a hairpin probe structure. Although the non-fluorescent quencher, DABCYL, also quenches a wide range of reporter dyes when utilized in probes with complementary ends (the so-called "molecular beacons" (9,22,23)), these probes exhibit temperature-dependent fluorescence and are not designed for use as 5'-exonuclease probes. We also wished to avoid the use of hairpin structures in order to simplify probe design.

Variations in signal among the probes as shown in FIG. 8 may be a function of the PCR efficiency, reporter fluorescence intensity or both. The data may potentially be improved by eliminating the signal variation and modifying the probes to improve discrimination between single-nucleotide mismatches. Extending the multicolor, multiplex PCR system to real-time, quantitative PCR is a possible next step but would require a new instrument capable of measuring the sample in real time at multiple excitation and emission wavelengths. Multiple colors allow for internal amplification standards that may aid in quantitation and may also be desirable for use with samples in which the target is available in limited quantities.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

What is claimed is:

1. A compound of formula (I):

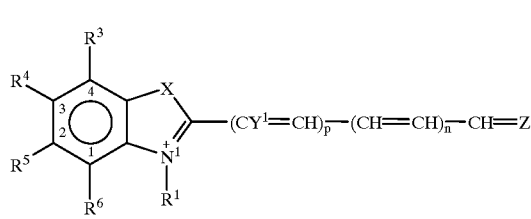

alone or in combination with a counterion thereof, wherein:

p is 0 or 1;

n is 0 or 1;

X is S, Se or O;

$N^1$ is nitrogen;

Z is selected from the group consisting of:

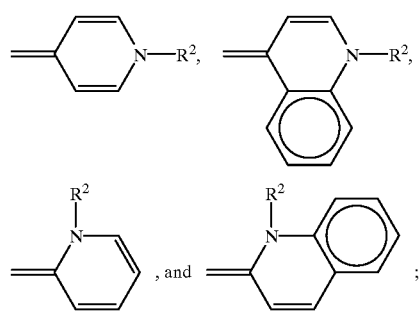

either:

(a) $R^2$ is A, $Y^1$ is H, and $R^1$ is —L—$R_x$, or (b) $R^2$ is —L—$R_x$, and:

(i) $R^1$ is A, or p3 (ii) p is 1, and $R^1$ and $Y^1$ taken together are $(CH_2)_q$;

A is selected from the group consisting of alkyl, aryl, —CH$_2$aryl, and —(CH$_2$)$_m$N$^+$(CH$_3$)$_3$;

L is selected from the group consisting of a bond, alkyldiyl, substituted alkyldiyl, alkyleno, substituted alkyleno, heteroalkyldiyl, substituted heteroalkyldiyl, heteroalkyleno, substituted heteroalkyleno, acyclic heteroatomic bridge, aryldiyl, substituted aryldiyl, arylaryldiyl, substituted arylaryldiyl, arylalkyldiyl, substituted arylalkyldiyl, heteroaryldiyl, substituted heteroaryldiyl, heteroaryl-heteroaryldiyl, substituted heteroaryl-heteroaryldiyl, heteroarylalkyldiyl, substituted heteroarylalkyldiyl, heteroaryl-heteroalkyldiyl, and substituted heteroaryl-heteroalkyldiyls;

said heteroalkyldiyl being an alkyldiyl group containing one or more —O—, —O—O—, —S—, —S—S—, —O—S—, —O—NR'—, —NR'—, NR'—NR'—, =N=N=, —N=N—, —N—O—N—, —NR'—N=N—, —PH—, —SH$_2$—, or —S(O)$_2$— groups, said R' being independently hydrogen or (C$_1$–C$_6$) alkyl;

said heteroalkyleno being an alkyleno group containing one or more —O—, —O—O—, —S—, —S—S—, —O—S—, —O—NR'—, —NR'—, NR'—NR'—, =N=N=, —N=N—, —N—O—N—, —NR'—N=N—, —PH—, —SH$_2$—, or —S(O)$_2$— groups, said R' being independently hydrogen or (C$_1$–C$_6$) alkyl;

said acyclic heteroatomic bridge being selected from the group consisting of —O—, —O—O—, —S—, —S—S—, —O—S—, —O—NR'—, —NR'—, NR'—NR'—, =N=N=, —N=N—, —N—O—N—, —NR'—N=N—, —PH—, —SH$_2$—, and —S(O)$_2$—, wherein R' is independently hydrogen or (C$_1$–C$_6$ alkyl);

said heteroaryldiyl being a divalent radical derived from a compound selected from the group consisting of acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole and xanthene;

said heteroaryl being a monovalent radical derived from a compound selected from the group consisting of acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole and xanthene;

R$_x$ is selected from the group consisting of acrylamide, acyl azide, acyl nitrile, acyl halide, aldehyde, alkyl halide, amine, anhydride, aniline, aryl halide, azide, aziridine, boronate, carboxylic acid, —COO$^-$M$^+$ wherein M$^+$ is a counterion, diazoalkane, haloacetamide, halotriazine, hydrazine, —CO(oxysuccinimidyl), —CO(oxysulfosuccinimidyl), —CO(oxybenzotriazoyl), isocyanate, isothiocyanate, maleimide, phosphoramidite, sulfonyl halide, thiol, and azidoperfluorobenzamido;

q is an integer ranging from 2 to 4;

each m is independently an integer ranging from 2 to 12;

A or (CH$_2$)$_q$ is unsubstituted or independently substituted with one or more of the same or different —NO$_2$, —OH, alkoxy, —COOH, —COOC$_1$–C$_4$ alkyl, —NHCHO, —NHCOC$_1$–C$_4$alkyl, —NHCOCH$_3$, —NHCOCH$_2$Cl, —NHCOCHCl$_2$, —NHCOCCl$_3$, —NHCOCF$_3$, —NHCOCH$_2$C$_6$H$_4$-o-NO$_2$, —NHCOCH$_2$OC$_6$H$_4$-o-NO$_2$, —NHCOCH$_2$COCH$_3$, —NHCOCH$_2$—N$^+$C$_5$H$_5$Cl$^-$, —NHCOCH$_2$NHCS$_2$CH$_2$C$_6$H$_5$, —NHCOCH$_2$CH$_2$C$_6$H$_5$, —NHCOCH$_2$CH$_2$C$_6$H$_4$-p-OH, —NHCOCH$_2$CH$_2$C$_6$H$_4$—o—NO$_2$, —NHCOC(CH$_3$)$_2$OC$_6$H$_4$-o-NO$_2$, —NHCOC(CH$_3$)$_2$OC$_6$H$_4$-o-N=NC$_6$H$_5$, —NHCO(CH$_2$)$_3$Cl, —NHCOCH(CH$_3$)$_2$, —NHCOCH=CHC$_6$H$_4$-o-NO$_2$, or —NHCO-2-pyridyl groups; either:

(a) R$^3$, R$^5$ and R$^6$ are H and R$^4$ is —NO$_2$; or (b) R$^3$ and R$^4$ taken together form a benzo group substituted with one or two —NO$_2$ groups and R$^5$ and R$^6$ are hydrogen; or (c) R$^4$ and R$^5$ taken together form a benzo group substituted with one or two —NO$_2$ groups and R$^3$ and R$^6$ are hydrogen; or (d) R$^5$ and R$^6$ taken together form a benzo group substituted with one or two —NO$_2$ groups and R$^3$ and R$^4$ are hydrogen; and with the proviso that when R$^1$ in the compounds of formula (I) has an sp$^3$ hybridized carbon atom that is covalently attached to N$^1$, then that carbon atom is methyl or, when substituted, primary, or to which is attached one or more hydroxyl, phenol, catechol, carbonyl, carboxyl, thiol or amino protecting groups.

2. The compound of claim 1, to which is attached one or more hydroxyl, phenol, catechol, carbonyl, carboxyl, thiol or amino protecting groups.

3. The compound of claim 1, wherein the compound is of the formula (XI):

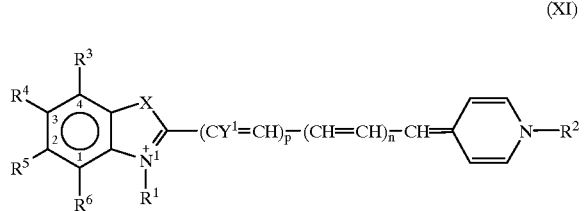

(XI)

alone or in combination with a counterion thereof, or to which is attached one or more hydroxyl, phenol, catechol, carbonyl, carboxyl, thiol or amino protecting groups.

4. The compound of claim 1, wherein the compound is of the formula (XII):

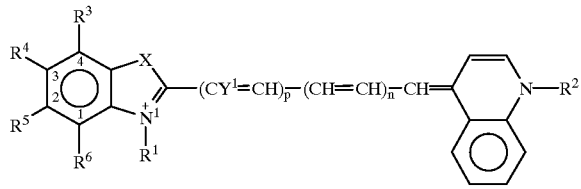
(XII)

alone or in combination with a counterion thereof, or to which is attached one or more hydroxyl, phenol, catechol, carbonyl, carboxyl, thiol or amino protecting groups.

5. The compound of claim 4, wherein the compound is of the formula (XIII):

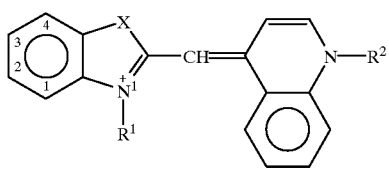
(XIII)

alone or in combination with a counterion thereof, or to which is attached one or more hydroxyl, phenol, catechol, carbonyl, carboxyl, thiol or amino protecting groups.

6. The compound of claim 4, wherein the compound is of the formula (XIV):

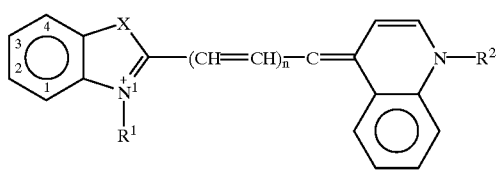
(XIV)

alone or in combination with a counterion thereof, or to which is attached one or more hydroxyl, phenol, catechol, carbonyl, carboxyl, thiol or amino protecting groups.

7. The compound of claim 1, wherein the compound is of the formula (XV):

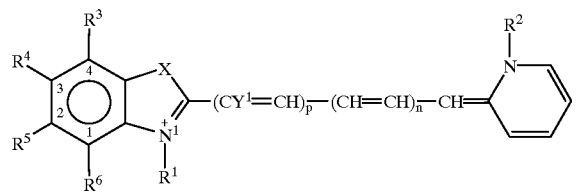
(XV)

alone or in combination with a counterion thereof, or to which is attached one or more hydroxyl, phenol, catechol, carbonyl, carboxyl, thiol or amino protecting groups.

8. The compound of claim 1, wherein the compound is of the formula (XVI):

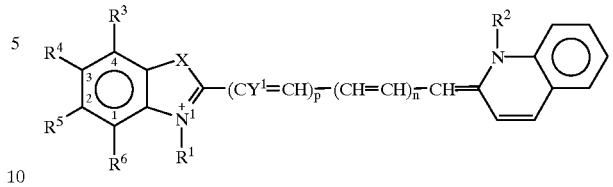
(XVI)

alone or in combination with a counterion thereof, or to which is attached one or more hydroxyl, phenol, catechol, carbonyl, carboxyl, thiol or amino protecting groups.

9. The compound of claim 1, wherein the compound is of the formula (XVII):

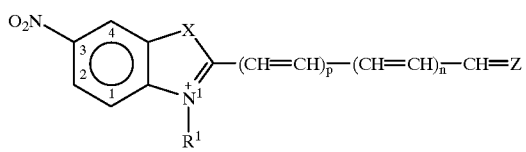
(XVII)

alone or in combination with a counterion thereof, or to which is attached one or more hydroxyl, phenol, catechol, carbonyl, carboxyl, thiol or amino protecting groups.

10. The compound of claim 1, wherein the compound is of the formula

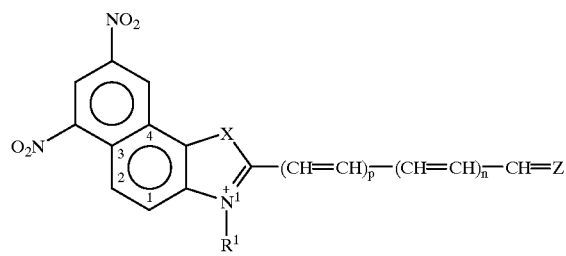
(XVIII)

alone or in combination with a counterion thereof, or to which is attached one or more hydroxyl, phenol, catechol, carbonyl, carboxyl, thiol or amino protecting groups.

11. The compound of claim 1, wherein the compound is of the formula (XIX):

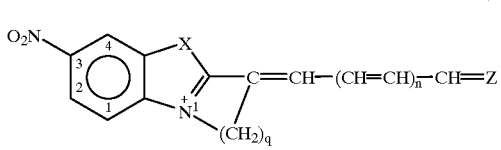
(XIX)

alone or in combination with a counterion thereof, or to which is attached one or more hydroxyl, phenol, catechol, carbonyl, carboxyl, thiol or amino protecting groups.

12. The compound of claim 1, wherein the compound is of the formula (XX):

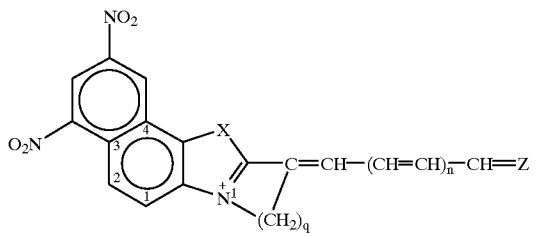

(XX)

alone or in combination with a counterion thereof, or to which is attached one or more hydroxyl, phenol, catechol, carbonyl, carboxyl, thiol or amino protecting groups.

13. The compound of claim 1, wherein —L—$R_x$ is amine or lower alkylcarboxy.

14. The compound of claim 1, wherein one of $R^1$ and $R^2$ is —$(CH_2)_m N^+(CH_3)_3$ and the other of $R^1$ and $R^2$ is —L—$R_x$.

15. The compound of claim 1, wherein —L—$R_x$ is —$(CH_2)_m N^+(CH_3)_2(CH_2)_m CO_2 H$.

16. The compound of claim 1, wherein X is sulfur.

17. The compound of claim 1, wherein q is 2.

18. The compound of claim 4 having the structure:

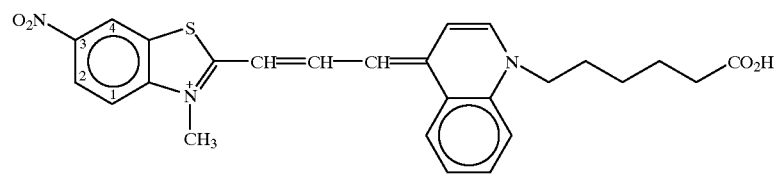

alone or in combination with a counterion thereof, or to which is attached one or more hydroxyl, phenol, catechol, carbonyl, carboxyl, thiol or amino protecting groups.

19. The compound of claim 4 having the structure:

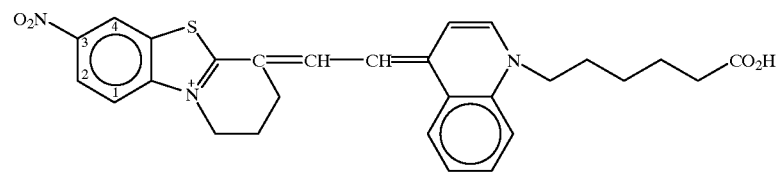

alone or in combination with a counterion thereof, or to which is attached one or more hydroxyl, phenol, catechol, carbonyl, carboxyl, thiol or amino protecting groups.

20. The compound of claim 4 having the structure:

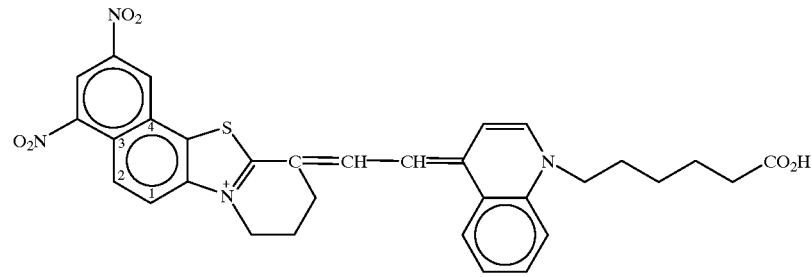

alone or in combination with a counterion thereof, or to which is attached one or more hydroxyl, phenol, catechol, carbonyl, carboxyl, thiol or amino protecting groups.

21. The compound of claim 4 having the structure:

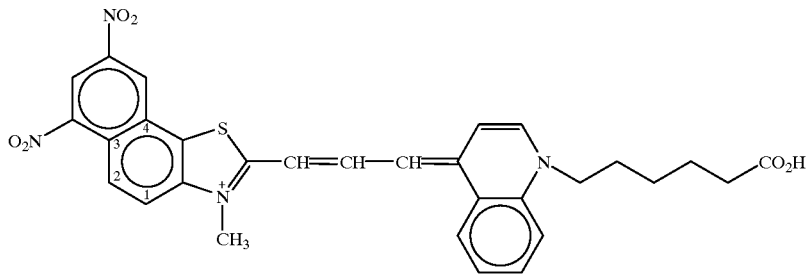

alone or in combination with a counterion thereof, or to which is attached one or more hydroxyl, phenol, catechol, carbonyl, carboxyl, thiol or amino protecting groups.

22. The compound of claim 4 having the structure:

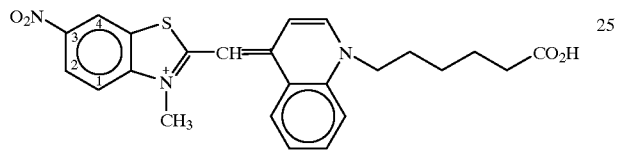

alone or in combination with a counterion thereof, or to which is attached one or more hydroxyl, phenol, catechol, carbonyl, carboxyl, thiol or amino protecting groups.

23. The compound of claim 4 having the structure:

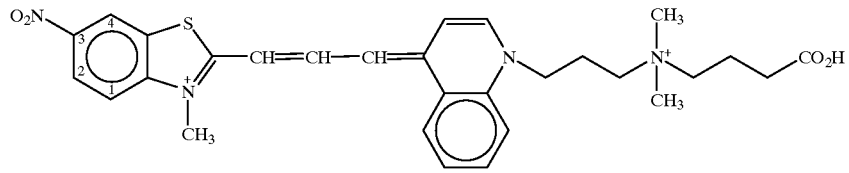

alone or in combination with a counterion thereof, or to which is attached one or more hydroxyl, phenol, catechol, carbonyl, carboxyl, thiol or amino protecting groups.

24. A composition comprising a reporter dye having a chromophore that, when exposed to radiation, emits radiation detectable by spectroscopic means, and a compound according to claim 1.

25. The composition according to claim 24, wherein the reporter dye is selected from the group consisting of xanthene, coumarin, napthylamine, cyanine, and BODIPY™ dyes.

26. The composition according to claim 25, wherein the reporter dye is a xanthene dye.

27. The composition according to claim 26, wherein the xanthene dye is selected from the group consisting of a fluorescein dye and a rhodamine dye.

28. The composition according to claim 24, wherein the chromophore is selected from the group consisting of

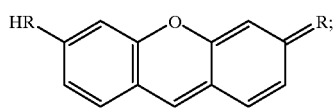

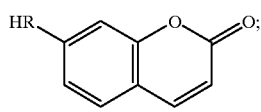

-continued

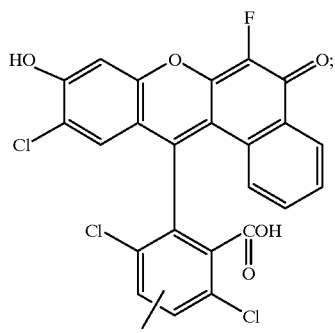

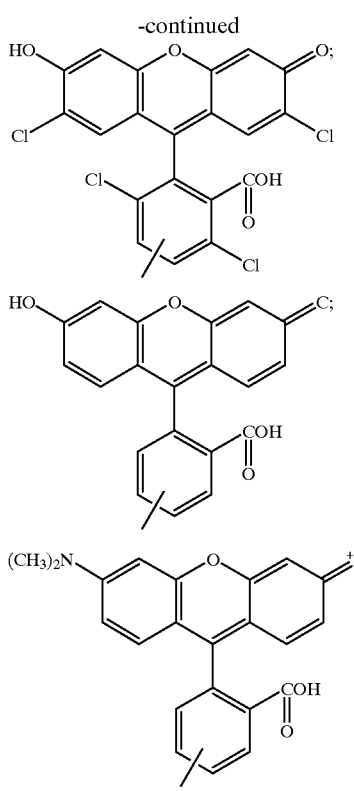
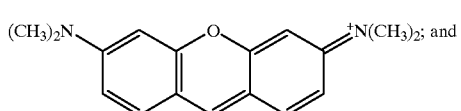
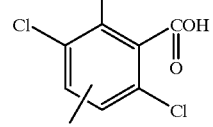
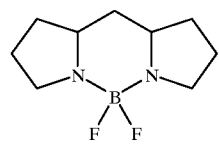
wherein R is N or O.
* * * * *

UNITED STATES PATENT AND TRADEMARK OFFICE
CERTIFICATE OF CORRECTION

PATENT NO. : 6,348,596 B1
DATED : February 19, 2002
INVENTOR(S) : Lee et al.

It is certified that error appears in the above-identified patent and that said Letters Patent is hereby corrected as shown below:

<u>Column 78,</u>
Line 66, thereof, delete the term "p3".

Signed and Sealed this

Twenty-third Day of April, 2002

Attest:

JAMES E. ROGAN
*Attesting Officer*     *Director of the United States Patent and Trademark Office*

```
                          SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
aaatcttggg ctggtagtgc taaa                                          24

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
ggccaggctg gtcttgaac                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
tgggcctgac cactcctttt                                               19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
tgcgatcccg cttgtgat                                                 18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5
agaggagacc ccgaaagaaa g                                             21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
```
ggctggtccc cgtcttct                                        18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Probe

<400> SEQUENCE: 7
tgatccacct gcctcagcct c                                    21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 8
tgatccaccc gcctcagcct                                      20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 9
ctgcccatcc ccagcccct                                       19

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 10
ctgcccagcc ccagccc                                         17

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 11
ccttctctgt tgccacttca gcctct                               26

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 12
ccttctctgt ggccacttca gcct                                 24

<210> SEQ ID NO 13
<211> LENGTH: 75
<212> TYPE: DNA
<213> ORGANISM: Artificial Sequence

```
<220> FEATURE:
<223> OTHER INFORMATION: Description of Artificial Sequence:
      Oligonucleotide

<400> SEQUENCE: 13
agaaatcttg gctggtagt gctaaattca aaggctgggg acaggctggg gccagtggct    60
catgcctgta atccc                                                   75

<210> SEQ ID NO 14
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
ttggccaggc tggtcttgaa ctcctgacct caagtgatcc acccgcctca gcctcccaaa    60
gtgctgggat tacag                                                    75

<210> SEQ ID NO 15
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
ttggccaggc tggtcttgaa ctcctgacct caagtgatcc acctgcctca gcctcccaaa    60
gtgctgggat tacag                                                    75

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
cctgggcctg accactcctt tgcccccca ggtggactgg gggctgccca tcccc          55

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
tctgcgatcc cgcttgtgat gggccgggtg aatgggggag gggctgggga tgggc          55

<210> SEQ ID NO 18
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
cctgggcctg accactcctt tgcccccca ggtggactgg gggctgccca gcccc           55
```

```
<210> SEQ ID NO 19
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
tctgcgatcc cgcttgtgat gggccgggtg aatgggggag gggctggggc tgggc        55

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gaagaggaga ccccgaaaga aagcctcaca gaggctgaag tggc                   44

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
tgggctggtc cccgtcttct ccttccttct ctgttgccac ttcag                  45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
tgggctggtc cccgtcttct ccttccttct ctgtggccac ttcag                  45
```